United States Patent
MacKinnon

(10) Patent No.: US 6,641,997 B1
(45) Date of Patent: Nov. 4, 2003

(54) ASSAYS FOR SCREENING COMPOUNDS WHICH INTERACT WITH CATION CHANNEL PROTEINS, MUTANT PROKARYOTIC CATION CHANNEL PROTEINS, AND USES THEREOF

(75) Inventor: Roderick MacKinnon, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 09/275,252

(22) Filed: Mar. 24, 1999

Related U.S. Application Data

(63) Continuation-in-part of application No. 09/054,347, filed on Apr. 2, 1998, now abandoned, which is a continuation-in-part of application No. 09/045,529, filed on Mar. 20, 1998, now abandoned.

(51) Int. Cl.[7] ............... C12Q 1/68; G01N 33/53; G01N 33/566

(52) U.S. Cl. ............... 435/6; 435/7.1; 435/7.2; 436/501

(58) Field of Search ............... 435/6, 7.1, 7.2; 436/501

(56) References Cited

U.S. PATENT DOCUMENTS

| | | | |
|---|---|---|---|
| 4,313,734 A | 2/1982 | Leuvering | 436/525 |
| 4,373,932 A | 2/1983 | Gribnau et al. | 436/501 |
| 4,703,017 A | 10/1987 | Campbell et al. | 436/501 |
| 4,857,453 A | 8/1989 | Ullman et al. | 435/7.92 |
| 5,010,175 A | 4/1991 | Rutter et al. | 530/334 |
| 5,288,514 A | 2/1994 | Ellman | 435/4 |
| 5,368,712 A | 11/1994 | Tomich et al. | 204/403 |
| 5,506,337 A | 4/1996 | Summerton et al. | 528/391 |
| 5,519,134 A | 5/1996 | Acevedo et al. | 544/243 |
| 5,525,735 A | 6/1996 | Gallop et al. | 548/533 |
| 5,539,083 A | 7/1996 | Cook et al. | 530/333 |
| 5,549,974 A | 8/1996 | Holmes | 428/403 |
| 5,593,853 A | 1/1997 | Chen et al. | 435/29 |
| 5,593,862 A | 1/1997 | Hall et al. | 435/69.1 |

FOREIGN PATENT DOCUMENTS

| | | |
|---|---|---|
| EP | 0280559 | 8/1988 |
| EP | 0281327 | 9/1998 |
| WO | WO 88/08534 | 11/1988 |
| WO | WO 90/02545 | 3/1990 |
| WO | WO 91/19735 | 12/1991 |
| WO | WO 92/00091 | 1/1992 |
| WO | WO 93/20242 | 10/1993 |
| WO | WO 95/16206 | 6/1995 |
| WO | WO 96/14860 | 5/1996 |
| WO | PCT/US96/10287 | 1/1997 |

OTHER PUBLICATIONS

Koyama et al., *FEBS Lett*, 341:303–7 (1994).
Morishige et al., *FEBS Lett*, 346:251–6 (1994).
Inagaki et al., *J Biol Chem*, 270:5691–4 (1995).
Ferrer et al., *J Biol Chem*, 270:26086–91 (1995).
Liman et al., *Nature*, 353:752–6 (1991).
Miller et al., *Neuron*, 16:853–8 (1996).
Tang et al., *J Gen Physiol*, 109:301–11 (1997).
Collioud et al., *Bioconjugate Chem*, 4:528–536 (1993).
Schuhmann et al., *Adv. Mater.*, 3:388–391 (1991).
Lu et al., *Anal. Chem.*, 67:83–87 (1995).
Iwane et al., *Biophys. Biochem. Res. Comm.*, 230:76–80 (1997).
Ng et al., *Langmuir*, 11:4048–55 (1995).
Schmitt et al., *Angew. Chem. Int. Ed. Engl.*, 35:317–20 (1996).
Frey et al., *Proc. Natl. Acad. Sci. USA*, 93:4937–41 (1996).
Kubalek et al., *J. Struct. Biol.*, 113:117–123 (1994)).
Sigal et al., *Anal. Chem.*, 68:490–497 (1996).
Gascoigne et al., *Proc. Natl. Acad. Sci. USA*, 84:2936–2940 (1987).
Capon et al., *Nature*, 377:525–531 (1989).
Traunecker et al., *Nature*, 339:68–70 (1989).
Heginbotham et al., *J Gen Physiol*, 111(6):741–9 (Jun. 1998).
Cuello et al., *Biochemistry* Mar 10, 37(10):3229–36. (1998).
Shin et al., *FEBS Lett* Oct 6, 415(3):299–302 (1997).
Santacruz–Toloza et al., *Biochemistry*, 33(6):1295–9. (Feb. 1994).
Furka et al., *Int. J. Pept. Prot. Res.*, 37:487–493 (1991).
Houghten et al., *Nature*, 354:84–88) (1991).
Hobbs et al., *Proc. Nat. Acad. Sci. USA*, 90:6909–6913 (Aug. 1993).
Hagihara et al., *J. Amer. Chem. Soc.*, 114:6568 (1992).
Hirschmann et al., *J. Amer. Chem. Soc.*, 114:9217–9218 (1992).
Chen et al., *J. Amer. Chem. Soc.*, 116:2661 (1994).
Cho, et al., *Science*, 261:1303 (1993).
Campbell et al., *J. Org. Chem*, 59:658 (1994).
Gordon et al., *J. Med. Chem.*, 37:1385 (1994).
Vaughan et al., *Nature Biotechnology*, 14(3):309–314 (1996).
Liang et al., *Science*, 274:1520–1522 (1996).
Ackerman et al., *New Engl. J. Med.*, 336:1575–1595 (1997).
Hamil et al., *PFlugers. Archiv.*, 391:85 (1981).
Vestergaard–Bogind et al., *J. Membrane Biol.*, 88:67–75 (1985).

(List continued on next page.)

*Primary Examiner*—Gabrielle Bugaisky
(74) *Attorney, Agent, or Firm*—Klauber & Jackson

(57) ABSTRACT

Assays for screening potential drugs or agents that can interact and potentially bind to cation channel proteins, and potentially have uses in treating conditions related to the function of cation channel proteins is provided, along with prokaryotic cation channel proteins mutated to mimic eukaryotic cation channels, which can then be used in assays of the present invention.

19 Claims, 13 Drawing Sheets

OTHER PUBLICATIONS

Daniel et al., *J. Pharmacol. Meth.*, 25:185–193 (1991).
Holevinsky et al., *J. Membrane Biology*, 137:59–70 (1994).
Blatz et al., *Nature*, 323:718–720 (1986).
Park, *J. Physiol.*, 481:555–570 (1994).
Kohler et al., *Nature*, 256:495–497 (1975).
Kozbor et al., *Immunology Today*, 4:72 (1983).
Cote et al., *Proc. Natl. Acad. Sci. U.S.A.*, 80:2026–2030 (1983).
Cole et al., in *Monoclonal Antibodies and Cancer Therapy*, Alan R. Liss, Inc., pp. 77–96 (1985).
Morrison et al., *J. Bacteriol.*, 159:870 (1984).
Neuberger et al., *Nature*, 312:604–608 (1984).
Takeda et al., *Nature*, 314:452–454 (1985).
Huse et al., *Science*, 246:1275–1281 (1989).
Engvall, *Methods in Enzymology*, 70:419–439 (1980).
Benoist et al., *Nature*, 290:304–310 (1981).
Yamamoto, et al., *Cell*, 22:787–797 (1980).
Wagner et al., *Proc. Natl. Acad. Sci. U.S.A.*, 78:1441–1445 (1981).
Brinster et al., *Nature*, 296:39–42 (1982).
Villa–Komaroff, et al., *Proc. Natl. Acad. Sci. U.S.A.*, 75:3727–3731 (1978).
DeBoer et al., *Proc. Natl. Acad. Sci. U.S.A.*, 80:21–25 (1983).
Gilbert et al., *Scientific American*, 242:74–94 (1980).
Swift et al., *Cell*, 38:639–646 (1984).
Ornitz et al., *Cold Spring Harbor Symp. Quant. Biol.*, 50:399–409 (1986).
MacDonald, *Hepatology*, 7:42S–51S (1987).
Hanahan, *Nature*, 315:115–122 (1985).
Grosschedl et al., *Cell*, 38:647–658 (1984).
Adams et al., *Nature*, 318:533–538 (1985).
Alexander et al., *Mol. Cell. Biol.*, 7:1436–1444 (1987).
Leder et al., *Cell*, 45:485–495 (1986).
Pinkert et al., *Genes and Devel.*, 1:268–276 (1987).
Krumlauf et al., *Mol. Cell. Biol.*, 5:1639–1648 (1985).
Hammer et al., *Science*, 235:53–58 (1987).
Kelsey et al., *Genes and Devel.*, 1:161–171 (1987).
Magram et al., *Nature*, 315:338–340 (1985).
Kollias et al., *Cell*, 46:89–94 (1986).
Readhead et al., *Cell*, 48:703–712 (1987).
Shani, *Nature*, 314:283–286 (1985).
Mason et al., *Science*, 234:1372–1378 (1986).
Bugg et al., *Scientific American*, 12:92–98 (1993).
West et al., *TIPS*, 16:67–74 (1995).
Lam et al., *Science*, 263:380–384 (1994).
Wlodawer et al., *Ann. Rev. Biochem.*, 62:543–585 (1993).
Appelt, *Perspectives in Drug Discovery and Design*, 1:23–48 (1993).
Erickson, *Perspectives in Drug Discovery and Design*, 1:109–128 (1993).
Scott et al., *Science*, 249:386–390 (1990).
Cwirla et al., *Proc. Natl. Acad.Sci.*, 87:6378–6382 (1990).
Devlin et al., *Science*, 249:404–406 (1990).
Navaza, *Acta Crystallographics A50*, 157–163 (1994).
Hodgkin et al., *J. Physiol.* (Lond.), 128:61 (1955).
Hagiwara et al., *J. Gen. Physiol.*, 70:269 (1977).
Hille et al., *J. Gen. Physiol.*, 72:409 (1978).
Neyton et al., *J. Gen. Physiol.*, 92:549 (1988).
Armstrong et al., *J. Gen. Physiol.*, 48:859 (1965).
Armstrong, *J. Gen. Physiol.*, 50:491 (1966).
Armstrong, *J. Gen. Physiol.*, 54:553 (1969).
Armstrong, *J. Gen. Physiol.*, 58:413 (1971).
Heginbotham et al., *Science*, 258:1152 (1992).
Heginbotham et al., *J. Biophys.*, 66:1061 (1994).
Heginbotham et al., *Biochemistry*, 36:10335 (1997).
Cortes et al., *Biochemistry*, 36:10343 (1997).
MacKinnon, *Nature*, 350:232 (1991).
Ketchum et al., *Nature*, 376:690 (1995).
Doyle et al., *Science*, 280:69–77 (1998).
Kleywegt et al., *Structure*, 5:1557 (1997).
Deisenhofer et al., *Nature*, 318:618 (1985).
Cowan et al., *Nature*, 358:727 (1992).
Kreusch et al., *J. Mol. Biol.*, 243:891 (1994).
MacKinnon et al., *Science*, 245:1382 (1989).
MacKinnon et al., *Neuron*, 5:767 (1990).
Stocker et al., *Proc. Natl. Acad. Sci. U.S.A.*, 91:9509 (1994).
Goldstein et al., *Neuron*, 12:1377 (1994).
Hidalgo et al., *Science*, 268:307 (1995).
Aiyar et al., *Neuron*, 15:1169 (1995).
Naranjo et al., *Neuron*, 16:123 (1996).
Ranganathan et al., *Neuron*, 16:131 (1996).
Gross et al., *Neuron*, 16:399 (1996).
Armstrong et al., *J. Gen. Physiol.*, 59:388 (1972).
MacKinnon et al., *Science*, 250:276 (1990).
Yellen et al., *Science*, 251:939 (1991).
Liu et al., *Neuron*, 19:175 (1997).
Parsegian, *Annals NY Acad. Sciences*, 264:161 (1975).
Sali et al., *Nature*, 335:740 (1988).
Aqvist et al., *Proc. Natl. Acad. Sci. U.S.A.*, 88:2026 (1991).
Lockhart et al., *Science*, 257:947 (1992).
Lockhart et al., *Science*, 260:198–199 (1993).
Bezanilla et al., *J. Gen. Physiol.*, 60:588 (1972).
Hille, *J. Gen. Physiol.*, 61:669 (1973).
Almers et al., *J. Physiol.* (Lond.), 353:585 (1984).
Hess et al., *Nature*, 309:453 (1984).
Neyton et al., *J. Gen. Physiol.*, 92:569 (1988).
Tate et al., *J. Appl. Crys.*, 28:196 (1995).
Thiel, et al., *Rev. Sci. Instrum.*, 67:3361 (1996).
Otwinowski et al., *Science and Engineering Research Council*, Daresbury Laboratory, Daresbury, UK, (1993), pp. 56–62.
Collaborative Computational Project 4 (CCP4), *Acta Cryst.*, D50:760 (1994).
Sheldrick, *Acta Cryst.*, 46:467 (1990).
Jones et al., *Acta Cryst.*, A47:110 (1991).
Gamblin et al., *Proceedings of the CCP4 Study weekend*, Daresbury Laboratory, pp. 163–169 (1996).
Zhang et al., *Acta Cryst.*, A46:377 (1990).
Kraulis, *J. Appl. Crys.*, 24:946 (1991).
Smart et al., *J. Mol. Graphics*, 14:354 (1996).
Garcia et al., *J. Bioenerg. Biomem.*, 23:615 (1991).
Miller, *Neuron*, 15:5 (1995).
MacKinnon et al., *J. Gen. Physiol.*, 91:335 (1998).
Park et al., *Neuron*, 9:307 (1992).
DeBin et al. *Am. J. Physiol. Soc.*, 264:C369 (1993).
Lippens et al., *Biochemistry*, 34:13 (1995).
Aggarwal et al., *Neuron*, 16:1169 (1996).
Cohen et al., *Anal. Chem.*, 68:31 (1996).
Krezel et al., *Prot. Sci.*, 4:1478 (1995).
Nicholls et al., *Proteins*, 11:281 (1991).
Gross et al., Neuron, 13: 961–66, 1994.
Hanner et al., *J.. Biol. Chem.*, 273: 16289–96, 1998.
Ishii et al, J. Biol. Chem., 272: 23195–23200, 1997.
MacKinnon et al., Science, 280: 106–9, 1998.
Pongs et al., The EMBO J, 7: 1087–96, 1988.
Schrempf et al., The EMBO J,147:5170–78, 1995.
Wang et al, PNAS USA, 95: 2653–58, 1998.
Garcia et al., Biochemistry 33: 6834–6839, 1994.

FIG. 8A  FIG. 8B
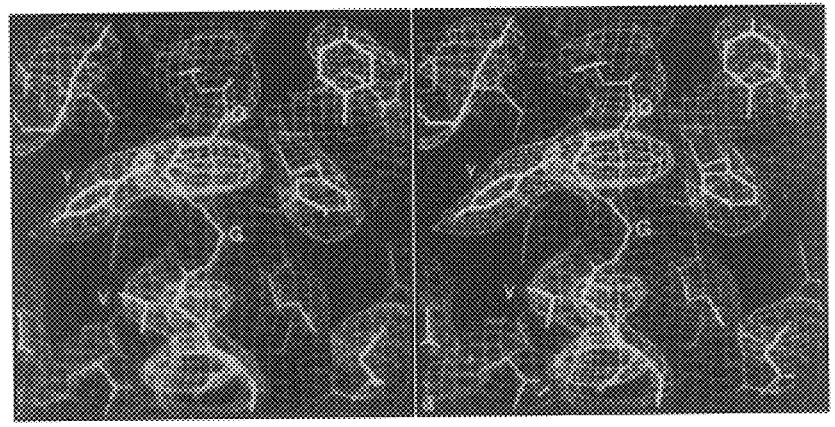
FIG. 8C  FIG. 8D
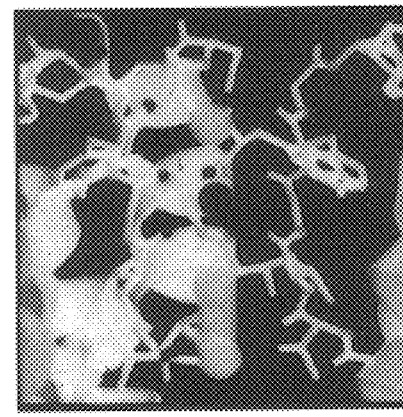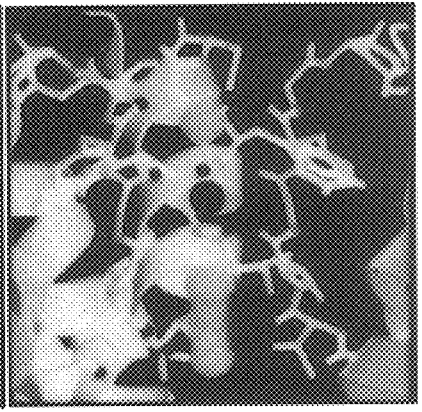
FIG. 8E
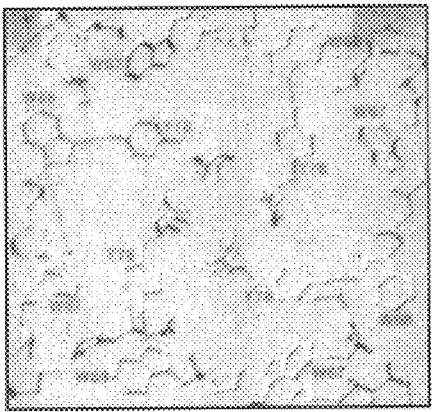

FIG. 10A  Chlorotoxin   Whole Venom

FIG. 10B   (-) Channel

FIG. 10C   (+) Channel

| Toxin | Mass (Da) Measured | Calculated |
|---|---|---|
| Chlorotoxin | 3996.4 | 3996.7 |
| Agitoxin 2 | 4090.8 | 4090.9 |
| * | 4113.5 | -------- |
| Charybdotoxin | 4295.9 | 4296.0 |
| Lq2 | 4336.1 | 4336.0 |

SEQUENCE LISTING

<160> NUMBER OF SEQ ID NOS: 42

<210> SEQ ID NO 1
<211> LENGTH: 160
<212> TYPE: PRT
<213> ORGANISM: Streptomyces lividans

<400> SEQUENCE: 1

```
Met Pro Pro Met Leu Ser Gly Leu Leu Ala Arg Leu Val Lys Leu Leu
 1               5                  10                  15

Leu Gly Arg His Gly Ser Ala Leu His Trp Arg Ala Ala Gly Ala Ala
            20                  25                  30

Thr Val Leu Leu Val Ile Val Leu Leu Ala Gly Ser Tyr Leu Ala Val
        35                  40                  45

Leu Ala Glu Arg Gly Ala Pro Gly Ala Gln Leu Ile Thr Tyr Pro Arg
    50                  55                  60

Ala Leu Trp Trp Ser Val Glu Thr Ala Thr Thr Val Gly Tyr Gly Asp
65                  70                  75                  80

Leu Tyr Pro Val Thr Leu Trp Gly Arg Leu Val Ala Val Val Val Met
                85                  90                  95

Val Ala Gly Ile Thr Ser Phe Gly Leu Val Thr Ala Ala Leu Ala Thr
            100                 105                 110

Trp Phe Val Gly Arg Glu Gln Glu Arg Gly His Phe Val Arg His
            115                 120                 125

Ser Glu Lys Ala Ala Glu Ala Tyr Thr Arg Thr Thr Arg Ala Leu
    130                 135                 140

His Glu Arg Phe Asp Arg Leu Glu Arg Met Leu Asp Asp Asn Arg Arg
145                 150                 155                 160
```

<210> SEQ ID NO 2
<211> LENGTH: 417
<212> TYPE: PRT
<213> ORGANISM: Escherichia coli

<400> SEQUENCE: 2

```
Met Ser His Trp Thr Thr Phe Lys Gln Thr Ala Thr Lys Leu Trp Val
 1               5                  10                  15

Thr Leu Arg His Asp Ile Leu Ala Leu Ala Val Phe Leu Asn Gly Leu
            20                  25                  30

Leu Ile Phe Lys Thr Ile Tyr Gly Met Ser Val Asn Leu Leu Asp Ile
        35                  40                  45

Phe His Ile Lys Ala Phe Ser Glu Leu Asp Leu Ser Leu Leu Ala Asn
    50                  55                  60

Ala Pro Leu Phe Met Leu Gly Val Phe Leu Val Leu Asn Ser Ile Gly
65                  70                  75                  80

Leu Leu Phe Arg Ala Lys Leu Ala Trp Ala Ile Ser Ile Leu Leu
                85                  90                  95

Leu Ile Ala Leu Ile Tyr Thr Leu His Phe Tyr Pro Trp Leu Lys Phe
            100                 105                 110

Ser Ile Gly Phe Cys Ile Phe Thr Leu Val Phe Leu Ile Leu Arg
            115                 120                 125

Lys Asp Phe Ser His Ser Ser Ala Ala Gly Thr Ile Phe Ala Phe
    130                 135                 140

Ile Ser Phe Thr Thr Leu Leu Phe Tyr Ser Thr Tyr Gly Ala Leu Tyr
145                 150                 155                 160
```

```
Leu Ser Glu Gly Phe Asn Pro Arg Ile Glu Ser Leu Met Thr Ala Phe
                165                 170                 175
Tyr Phe Ser Ile Glu Thr Met Ser Thr Val Gly Tyr Gly Asp Ile Val
            180                 185                 190
Pro Val Ser Glu Ser Ala Arg Leu Phe Thr Ile Ser Val Ile Ile Ser
        195                 200                 205
Gly Ile Thr Val Phe Ala Thr Ser Met Thr Ser Ile Phe Gly Pro Leu
    210                 215                 220
Ile Arg Gly Gly Phe Asn Lys Leu Val Lys Gly Asn Asn His Thr Met
225                 230                 235                 240
His Arg Lys Asp His Phe Ile Val Cys Gly His Ser Ile Leu Ala Ile
                245                 250                 255
Asn Thr Ile Leu Gln Leu Asn Gln Arg Gly Gln Asn Val Thr Val Ile
            260                 265                 270
Ser Asn Leu Pro Glu Asp Ile Lys Gln Leu Glu Gln Arg Leu Gly
        275                 280                 285
Asp Asn Ala Asp Val Ile Pro Gly Asp Ser Asn Asp Ser Ser Val Leu
    290                 295                 300
Lys Lys Ala Gly Ile Asp Arg Cys Arg Ala Ile Leu Ala Leu Ser Asp
305                 310                 315                 320
Asn Asp Ala Asp Asn Ala Phe Val Val Leu Ser Ala Lys Asp Met Ser
                325                 330                 335
Ser Asp Val Lys Thr Val Leu Ala Val Ser Asp Ser Lys Asn Leu Asn
            340                 345                 350
Lys Ile Lys Met Val His Pro Asp Ile Ile Leu Ser Pro Gln Leu Phe
        355                 360                 365
Gly Ser Glu Ile Leu Ala Arg Val Leu Asn Gly Glu Glu Ile Asn Asn
    370                 375                 380
Asp Met Leu Val Ser Met Leu Leu Asn Ser Gly His Gly Ile Phe Ser
385                 390                 395                 400
Asp Asn Asp Glu Gln Glu Thr Lys Ala Asp Ser Lys Glu Ser Ala Gln
                405                 410                 415
Lys

<210> SEQ ID NO 3
<211> LENGTH: 58
<212> TYPE: PRT
<213> ORGANISM: Clostridium acetobutylicum

<400> SEQUENCE: 3

Ser Leu Gly Asn Ala Leu Trp Trp Ser Phe Val Thr Ile Thr Thr Val
 1               5                  10                  15
Gly Tyr Gly Asp Ile Ser Pro Ser Thr Pro Phe Gly Arg Val Ile Ala
            20                  25                  30
Ser Ile Leu Met Leu Ile Gly Ile Gly Phe Leu Ser Met Leu Thr Gly
        35                  40                  45
Thr Ile Ser Thr Phe Phe Ile Ser Lys Lys
    50                  55

<210> SEQ ID NO 4
<211> LENGTH: 616
<212> TYPE: PRT
<213> ORGANISM: Drosophila melanogaster

<400> SEQUENCE: 4
```

-continued

```
Met Ala Ala Val Ala Gly Leu Tyr Gly Leu Gly Glu Asp Arg Gln His
 1               5                  10                  15

Arg Lys Lys Gln Gln Gln Gln Gln His Gln Lys Glu Gln Leu Glu
            20                  25                  30

Gln Lys Glu Glu Gln Lys Lys Ile Ala Glu Arg Lys Leu Gln Leu Arg
            35                  40                  45

Glu Gln Gln Leu Gln Arg Asn Ser Leu Asp Gly Tyr Gly Ser Leu Pro
        50                  55                  60

Lys Leu Ser Ser Gln Asp Glu Glu Gly Ala Gly His Gly Phe Gly
 65                  70                  75                  80

Gly Gly Pro Gln His Phe Glu Pro Ile Pro His Asp His Asp Phe Cys
                85                  90                  95

Glu Arg Val Val Ile Asn Val Ser Gly Leu Arg Phe Glu Thr Gln Leu
                100                 105                 110

Arg Thr Leu Asn Gln Phe Pro Asp Thr Leu Leu Gly Asp Pro Ala Arg
            115                 120                 125

Arg Leu Arg Tyr Phe Asp Pro Leu Arg Asn Glu Tyr Phe Phe Asp Arg
        130                 135                 140

Ser Arg Pro Ser Phe Asp Ala Ile Leu Tyr Tyr Tyr Gln Ser Gly Gly
145                 150                 155                 160

Arg Leu Arg Arg Pro Val Asn Val Pro Leu Asp Val Phe Ser Glu Glu
                165                 170                 175

Ile Lys Phe Tyr Glu Leu Gly Asp Gln Ala Ile Asn Lys Phe Arg Glu
                180                 185                 190

Asp Glu Gly Phe Ile Lys Glu Glu Arg Pro Leu Pro Asp Asn Glu
            195                 200                 205

Lys Gln Arg Lys Val Trp Leu Leu Phe Glu Tyr Pro Glu Ser Ser Gln
        210                 215                 220

Ala Ala Arg Val Val Ala Ile Ser Val Phe Val Ile Leu Leu Ser
225                 230                 235                 240

Ile Val Ile Phe Cys Leu Glu Thr Leu Pro Glu Phe Lys His Tyr Lys
                245                 250                 255

Val Phe Asn Thr Thr Thr Asn Gly Thr Lys Ile Glu Glu Asp Glu Val
                260                 265                 270

Pro Asp Ile Thr Asp Pro Phe Phe Leu Ile Glu Thr Leu Cys Ile Ile
            275                 280                 285

Trp Phe Thr Phe Glu Leu Thr Val Arg Phe Leu Ala Cys Pro Asn Lys
        290                 295                 300

Leu Asn Phe Cys Arg Asp Val Met Asn Val Ile Asp Ile Ile Ala Ile
305                 310                 315                 320

Ile Pro Tyr Phe Ile Thr Leu Ala Thr Val Val Ala Glu Glu Asp
                325                 330                 335

Thr Leu Asn Leu Pro Lys Ala Pro Val Ser Pro Gln Asp Lys Ser Ser
            340                 345                 350

Asn Gln Ala Met Ser Leu Ala Ile Leu Arg Val Ile Arg Leu Val Arg
        355                 360                 365

Val Phe Arg Ile Phe Lys Leu Ser Arg His Ser Lys Gly Leu Gln Ile
    370                 375                 380

Leu Gly Arg Thr Leu Lys Ala Ser Met Arg Glu Leu Gly Leu Leu Ile
385                 390                 395                 400

Phe Phe Leu Phe Ile Gly Val Val Leu Phe Ser Ser Ala Val Tyr Phe
                405                 410                 415

Ala Glu Ala Gly Ser Glu Asn Ser Phe Phe Lys Ser Ile Pro Asp Ala
```

```
                    420              425              430
Phe Trp Trp Ala Val Val Thr Met Thr Thr Val Gly Tyr Gly Asp Met
            435              440              445
Thr Pro Val Gly Phe Trp Gly Lys Ile Val Gly Ser Leu Cys Val Ile
450              455              460
Ala Gly Val Leu Thr Ile Ala Leu Pro Val Pro Val Ile Val Ser Asn
465              470              475              480
Phe Asn Tyr Phe Tyr His Arg Glu Ala Asp Arg Glu Met Gln Ser
            485              490              495
Gln Asn Phe Asn His Val Thr Ser Cys Ser Tyr Leu Pro Gly Ala Leu
                500              505              510
Gly Gln His Leu Lys Lys Ser Ser Leu Ser Glu Ser Ser Ser Asp Ile
            515              520              525
Met Asp Leu Asp Asp Gly Ile Asp Ala Thr Thr Pro Gly Leu Thr Asp
530              535              540
His Thr Gly Arg His Met Val Pro Phe Leu Arg Thr Gln Gln Ser Phe
545              550              555              560
Glu Lys Gln Gln Leu Gln Leu Gln Leu Gln Leu Gln Gln Ser Gln
                565              570              575
Ser Pro His Gly Gln Gln Met Thr Gln Gln Gln Leu Gly Gln Asn
            580              585              590
Gly Leu Arg Ser Thr Asn Ser Leu Gln Leu Arg His Asn Asn Ala Met
            595              600              605
Ala Val Ser Ile Glu Thr Asp Val
            610              615

<210> SEQ ID NO 5
<211> LENGTH: 495
<212> TYPE: PRT
<213> ORGANISM: Homo sapiens

<400> SEQUENCE: 5

Met Thr Val Met Ser Gly Glu Asn Val Asp Glu Ala Ser Ala Ala Pro
 1               5                10                  15
Gly His Pro Gln Asp Gly Ser Tyr Pro Arg Gln Ala Asp His Asp Asp
                20              25                  30
His Glu Cys Cys Glu Arg Val Val Ile Asn Ile Ser Gly Leu Arg Phe
            35              40              45
Glu Thr Gln Leu Lys Thr Leu Ala Gln Phe Pro Asn Thr Leu Leu Gly
        50              55              60
Asn Pro Lys Lys Arg Met Arg Tyr Phe Asp Pro Leu Arg Asn Glu Tyr
65              70              75              80
Phe Phe Asp Arg Asn Arg Pro Ser Phe Asp Ala Ile Leu Tyr Tyr Tyr
                85              90                  95
Gln Ser Gly Gly Arg Leu Arg Arg Pro Val Asn Val Pro Leu Asp Met
                100             105             110
Phe Ser Glu Glu Ile Lys Phe Tyr Glu Leu Gly Glu Glu Ala Met Glu
            115             120             125
Lys Phe Arg Glu Asp Glu Gly Phe Ile Lys Glu Glu Arg Pro Leu
130             135             140
Pro Glu Lys Glu Tyr Gln Arg Gln Val Trp Leu Leu Phe Glu Tyr Pro
145             150             155             160
Glu Ser Ser Gly Pro Ala Arg Val Ile Ala Ile Val Ser Val Met Val
                165             170             175
```

```
Ile Leu Ile Ser Ile Val Ile Phe Cys Leu Glu Thr Leu Pro Glu Leu
                180                 185                 190

Lys Asp Asp Lys Asp Phe Thr Gly Thr Val His Arg Ile Asp Asn Thr
            195                 200                 205

Thr Val Ile Tyr Asn Ser Asn Ile Phe Thr Asp Pro Phe Phe Ile Val
        210                 215                 220

Glu Thr Leu Cys Ile Ile Trp Phe Ser Phe Leu Val Val Arg Phe
225                 230                 235                 240

Phe Ala Cys Pro Ser Lys Thr Asp Phe Phe Lys Asn Ile Met Asn Phe
                245                 250                 255

Ile Asp Ile Val Ala Ile Ile Pro Tyr Phe Ile Thr Leu Gly Thr Glu
                260                 265                 270

Ile Ala Glu Gln Glu Gly Asn Gln Lys Gly Glu Gln Ala Thr Ser Leu
                275                 280                 285

Ala Ile Leu Arg Val Ile Arg Leu Val Arg Val Phe Arg Ile Phe Lys
            290                 295                 300

Leu Ser Arg His Ser Lys Gly Leu Gln Ile Leu Gly Gln Thr Leu Lys
305                 310                 315                 320

Ala Ser Met Arg Glu Leu Gly Leu Leu Ile Phe Phe Leu Phe Ile Gly
                325                 330                 335

Val Ile Leu Phe Ser Ser Ala Val Tyr Phe Ala Glu Ala Glu Glu Ala
                340                 345                 350

Glu Ser His Phe Ser Ser Ile Pro Asp Ala Phe Trp Trp Ala Val Val
                355                 360                 365

Ser Met Thr Thr Val Gly Tyr Gly Asp Met Tyr Pro Val Thr Ile Gly
        370                 375                 380

Gly Lys Ile Val Gly Ser Leu Cys Ala Ile Ala Gly Val Leu Thr Ile
385                 390                 395                 400

Ala Leu Pro Val Pro Val Ile Val Ser Asn Phe Asn Tyr Phe Tyr His
                405                 410                 415

Arg Glu Thr Glu Gly Glu Glu Gln Ala Gln Leu Leu His Val Ser Ser
                420                 425                 430

Pro Asn Leu Ala Ser Asp Ser Asp Leu Ser Arg Arg Ser Ser Ser Thr
            435                 440                 445

Met Ser Lys Tyr Glu Tyr Met Glu Ile Glu Glu Asp Met Asn Asn Ser
        450                 455                 460

Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
                485                 490                 495

<210> SEQ ID NO 6
<211> LENGTH: 858
<212> TYPE: PRT
<213> ORGANISM: Homo sapiens

<400> SEQUENCE: 6

Met Pro Ala Gly Met Thr Lys His Gly Ser Arg Ser Thr Ser Ser Leu
  1               5                  10                  15

Pro Pro Glu Pro Met Glu Ile Val Arg Ser Lys Ala Cys Ser Arg Arg
                20                  25                  30

Val Arg Leu Asn Val Gly Gly Leu Ala His Glu Val Leu Trp Arg Thr
            35                  40                  45

Leu Asp Arg Leu Pro Arg Thr Arg Leu Gly Lys Leu Arg Asp Cys Asn
        50                  55                  60
```

```
Thr His Asp Ser Leu Leu Glu Val Cys Asp Asp Tyr Ser Leu Asp Asp
 65                  70                  75                  80

Asn Glu Tyr Phe Phe Asp Arg His Pro Gly Ala Phe Thr Ser Ile Leu
                 85                  90                  95

Asn Phe Tyr Arg Thr Gly Arg Leu His Met Met Glu Glu Met Cys Ala
                100                 105                 110

Leu Ser Phe Ser Gln Glu Leu Asp Tyr Trp Gly Ile Asp Glu Ile Tyr
                115                 120                 125

Leu Glu Ser Cys Cys Gln Ala Arg Tyr His Gln Lys Lys Glu Gln Met
130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Ala Lys Ile Leu Ala
                180                 185                 190

Ile Ile Ser Ile Met Phe Ile Val Leu Ser Thr Ile Ala Leu Ser Leu
            195                 200                 205

Asn Thr Leu Pro Glu Leu Gln Ser Leu Asp Glu Phe Gly Gln Ser Thr
210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
                260                 265                 270

Tyr Tyr Val Thr Ile Phe Leu Thr Glu Ser Asn Lys Ser Val Leu Gln
                275                 280                 285

Phe Gln Asn Val Arg Arg Val Val Gln Ile Phe Arg Ile Met Arg Ile
                290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

Phe Leu Ala Met Gly Ile Met Ile Phe Ser Ser Leu Val Phe Phe Ala
                340                 345                 350

Glu Lys Asp Glu Asp Asp Thr Lys Phe Lys Ser Ile Pro Ala Ser Phe
                355                 360                 365

Trp Trp Ala Thr Ile Thr Met Thr Thr Val Gly Tyr Gly Asp Ile Tyr
370                 375                 380

Pro Lys Thr Leu Leu Gly Lys Ile Val Gly Gly Leu Cys Cys Ile Ala
385                 390                 395                 400

Gly Val Leu Val Ile Ala Leu Pro Ile Pro Ile Ile Val Asn Asn Phe
                405                 410                 415

Ser Glu Phe Tyr Lys Glu Gln Lys Arg Gln Glu Lys Ala Ile Lys Arg
                420                 425                 430

Arg Glu Ala Leu Glu Arg Ala Lys Arg Asn Gly Ser Ile Val Ser Met
                435                 440                 445

Asn Met Lys Asp Ala Phe Ala Arg Ser Ile Glu Met Met Asp Ile Val
                450                 455                 460

Val Glu Lys Asn Gly Glu Asn Met Gly Lys Asp Lys Val Gln Asp
465                 470                 475                 480
```

```
Asn His Leu Ser Pro Asn Lys Trp Lys Trp Thr Lys Arg Thr Leu Ser
                485                 490                 495

Glu Thr Ser Ser Ser Lys Ser Phe Glu Thr Lys Glu Gln Gly Ser Pro
            500                 505                 510

Glu Lys Ala Arg Ser Ser Ser Pro Gln His Leu Asn Val Gln Gln
        515                 520                 525

Leu Glu Asp Met Tyr Asn Lys Met Ala Lys Thr Gln Ser Gln Pro Ile
    530                 535                 540

Leu Asn Thr Lys Glu Ser Ala Ala Gln Ser Lys Pro Lys Glu Leu
545                 550                 555                 560

Glu Met Glu Ser Ile Pro Ser Pro Val Ala Pro Leu Pro Thr Arg Thr
                565                 570                 575

Glu Gly Val Ile Asp Met Arg Ser Met Ser Ser Ile Asp Ser Phe Ile
                580                 585                 590

Ser Cys Ala Thr Asp Phe Pro Glu Ala Thr Arg Phe Ser His Ser Pro
            595                 600                 605

Leu Thr Ser Leu Pro Ser Lys Thr Gly Gly Ser Thr Ala Pro Glu Val
        610                 615                 620

Gly Trp Arg Gly Ala Leu Gly Ala Ser Gly Gly Arg Phe Val Glu Ala
625                 630                 635                 640

Asn Pro Ser Pro Asp Ala Ser Gln His Ser Ser Phe Phe Ile Glu Ser
                645                 650                 655

Pro Lys Ser Ser Met Lys Thr Asn Asn Pro Leu Lys Leu Arg Ala Leu
            660                 665                 670

Lys Val Asn Phe Met Glu Gly Asp Pro Ser Pro Leu Leu Pro Val Leu
        675                 680                 685

Gly Met Tyr His Asp Pro Leu Arg Asn Arg Gly Ser Ala Ala Ala
    690                 695                 700

Val Ala Gly Leu Glu Cys Ala Thr Leu Leu Asp Lys Ala Val Leu Ser
705                 710                 715                 720

Pro Glu Ser Ser Ile Tyr Thr Thr Ala Ser Ala Lys Thr Pro Pro Arg
                725                 730                 735

Ser Pro Glu Lys His Thr Ala Ile Ala Phe Asn Phe Glu Ala Gly Val
            740                 745                 750

His Gln Tyr Ile Asp Ala Asp Thr Asp Asp Glu Gly Gln Leu Leu Tyr
        755                 760                 765

Ser Val Asp Ser Ser Pro Pro Lys Ser Leu Pro Gly Ser Thr Ser Pro
    770                 775                 780

Lys Phe Ser Thr Gly Thr Arg Ser Glu Lys Asn His Phe Glu Ser Ser
785                 790                 795                 800

Pro Leu Pro Thr Ser Pro Lys Phe Leu Arg Gln Asn Cys Ile Tyr Ser
                805                 810                 815

Thr Glu Ala Leu Thr Gly Lys Gly Pro Ser Gly Gln Glu Lys Cys Lys
            820                 825                 830

Leu Glu Asn His Ile Ser Pro Asp Val Arg Val Leu Pro Gly Gly Gly
        835                 840                 845

Ala His Gly Ser Thr Arg Asp Gln Ser Ile
    850                 855

<210> SEQ ID NO 7
<211> LENGTH: 597
<212> TYPE: PRT
<213> ORGANISM: Paramecium tetraurelia

<400> SEQUENCE: 7
```

-continued

```
Met Gly Pro Lys Ile Arg Ala Ile Ser Phe Gln Ser Asn Lys Pro Met
 1               5                  10                  15

Met Asn Leu Lys Glu Asp Ser Pro Val Phe Ile Asp Ser His Thr Asp
             20                  25                  30

His Val Gly Phe Ser Asn Lys Ile Trp Arg Thr Lys Ala Leu Glu Ile
         35                  40                  45

Leu Met Ile Thr Leu Arg Phe Ile Ser Phe Ile Thr Lys Ser Asn Phe
     50                  55                  60

Ala Thr Ser Phe Lys Leu Ile Asn Lys Asn Val Phe Glu Ile Ile Gly
 65                  70                  75                  80

Asp Val Ser Ala Asp Phe Thr Tyr Tyr Leu Leu Lys Asn Phe Phe Lys
                 85                  90                  95

Tyr Glu Lys Pro Thr Gly Phe Gln Lys Gly Gln His Phe Leu Asn Gln
                100                 105                 110

Thr Leu Leu Ile Pro Leu Arg Lys Thr Lys Leu Leu Lys Ile Tyr Cys
            115                 120                 125

Gly Asn Gln Lys Leu Ile Met Arg Pro Glu Ser Leu Ala Ser Ile Trp
130                 135                 140

Trp Asn Ile Tyr Ile Leu Thr Ile Leu Asn Ile Asn Val Leu Tyr Val
145                 150                 155                 160

Ser Ile Lys Ile Ala Phe Lys Phe Asp Glu Gln Ser Gln Asp Asp Phe
                165                 170                 175

Tyr Gln Ala Arg Gln Ile Ile Phe Asp Val Leu Pro Ser Tyr Ser Phe
            180                 185                 190

Met Leu Glu Ile Leu Leu Lys Phe Asn Thr Cys Tyr Tyr Tyr Lys Gly
            195                 200                 205

Ala Val Ile Glu Asn Arg Tyr Gln Ile Ala Lys Asn Tyr Leu Arg Ser
210                 215                 220

Ser Phe Phe Asp Ile Phe Val Val Ile Pro Tyr Phe Ile Ser Leu
225                 230                 235                 240

Arg Phe Asp Leu Gln Tyr Leu Asp Leu Val Ile Ile Leu Lys Val Phe
            245                 250                 255

Gln Ile Thr Lys Phe Ser Arg Asn Leu Phe Asp Arg Leu Glu Leu Thr
            260                 265                 270

Ala Ile Gln Ile Val Ile Val Asp Leu Val Lys Leu Gly Tyr Thr Ile
            275                 280                 285

Leu Ala Ala His Phe Ser Ala Cys Ile Trp Phe Leu Val Gly Ser
            290                 295                 300

Thr Gly Asn Pro Asn Asp Thr Ser Trp Ile Lys Ala Gln Asn Ile Glu
305                 310                 315                 320

Asn Glu Gln Trp Phe Asn Gln Tyr Leu His Ser Leu Tyr Trp Ser Ile
                325                 330                 335

Ile Thr Met Thr Thr Ile Gly Tyr Gly Asp Ile Thr Pro Gln Asn Leu
            340                 345                 350

Arg Glu Arg Val Phe Ala Val Gly Met Ala Leu Ser Ala Val Gly Val
            355                 360                 365

Phe Gly Tyr Ser Ile Gly Asn Ile Asn Ser Ile Tyr Ala Glu Trp Ser
    370                 375                 380

Arg Gln Ser Phe Gln Ile Arg Thr Asp Met Asn Asn Leu Lys Lys Phe
385                 390                 395                 400

Ile Arg Ile Lys Gly Ile Asn Lys His Leu Ala Glu Lys Ile Arg Lys
                405                 410                 415
```

-continued

```
Tyr Phe Glu Tyr Val Trp Ser Asp Gln Met Glu Asp Asn Asp Arg Glu
            420                 425                 430

Val Tyr Lys Phe Ser Glu Met Ile Pro Lys Gln Leu Ala Glu Glu Met
            435                 440                 445

Lys Ile Asp Thr Asn Met Lys Leu Ile Gln Lys Asn Ser Phe Leu Val
            450                 455                 460

Asn Asn Phe Ser Glu Gln Phe Leu Ile Ser Leu Ser Lys Val Leu Ile
465                 470                 475                 480

Glu Glu Lys Tyr Val Pro Glu Ser Thr Ile Tyr Leu Val Lys Leu Ile
                    485                 490                 495

Asn Ile Leu Gln Gln Asn Asp Pro Ser Asn Tyr Leu Tyr Ile Leu Ser
            500                 505                 510

Asn Gly Ser Leu Ser Phe Tyr Ile Thr Leu Asn Asn Lys Gln Gln Thr
            515                 520                 525

Ile Lys Val Leu Glu Thr Ile Lys Asn Glu Gly Gln Ala Phe Gly Val
            530                 535                 540

Leu Glu Phe Phe Gln Ser Gln Ala Tyr Gln Val Ser Cys Lys Ser Asn
545                 550                 555                 560

Gln Phe Ser Tyr Val Leu Lys Ile Asp Lys Ser Gln Phe Met Glu Ile
                    565                 570                 575

Ile Ser Gln His Lys Asn Asp Tyr Val Thr Gln Ile Ile Tyr Leu Ile
            580                 585                 590

Leu Val Gln Ile Leu
            595

<210> SEQ ID NO 8
<211> LENGTH: 556

<212> TYPE: PRT
<213> ORGANISM: Caenorhabditis elegans

<400> SEQUENCE: 8

Asp Ala Cys Ser Phe Asn Arg Phe Asp Ser Asn Arg Ser Ser Ala Arg
1               5                   10                  15

Arg Phe Ser Arg Arg Gly Ser Asp Tyr Phe Gly Asp Lys Gly Ile Ser
                20                  25                  30

Met Asp Glu Arg Ile Val Leu Asn Val Gly Gly Val Arg His Glu Thr
            35                  40                  45

Tyr Gln Ala Thr Leu Lys Lys Ile Pro Ala Thr Arg Leu Ser Arg Leu
        50                  55                  60

Thr Pro Ser Leu Ala Asn Phe Asp Pro Leu Leu Asn Glu Tyr Phe Phe
65                  70                  75                  80

Asp Arg His Pro Ala Val Phe Ala Met Ile Leu Asn Tyr Tyr Arg Thr
                    85                  90                  95

Gly Lys Leu His Tyr Pro Thr Asp Val Cys Gly Pro Leu Phe Glu Glu
                100                 105                 110

Glu Leu Gln Tyr Trp Gly Leu Asp Ala Ser Asp Thr Glu Pro Cys Cys
            115                 120                 125

Trp Met Gln Leu Leu His Ala Lys Asp Thr Gln Glu Thr Leu Ala Val
        130                 135                 140

Leu Asp Arg Met Asp Ala Asp His Glu Asp Pro Gln Leu Arg Gln Glu
145                 150                 155                 160

Gln Asp Thr Met Lys Lys Phe Gly Trp Glu Glu Asp Tyr Phe Gln Gly
                    165                 170                 175

Lys Arg Thr Arg Trp Met Lys Leu Lys Pro Gln Met Trp Ser Leu Phe
```

-continued

```
                180                 185                 190
Asp Glu Pro Tyr Ser Ser Gln Ala Ala Lys Leu Ile Ala Gly Ile Ser
            195                 200                 205

Val Leu Phe Ile Phe Ile Ser Ile Phe Ser Phe Cys Leu Lys Thr His
        210                 215                 220

Gln Ser Phe Arg Leu Pro Val Leu Ile Gly Gln Asn Ile Thr Met Pro
225                 230                 235                 240

Gly Gly Val Val Gln Pro Ser Ile Glu Arg Val Ser Thr Glu Pro Leu
                245                 250                 255

Pro Ile Phe Gly Gln Ile Glu Met Leu Cys Asn Ile Trp Phe Thr Leu
            260                 265                 270

Glu Leu Ile Ile Arg Phe Val Phe Cys Pro Ser Lys Ile Arg Phe Phe
        275                 280                 285

Lys Ser Pro Leu Asn Met Ile Asp Leu Val Ala Thr Leu Ser Phe Tyr
        290                 295                 300

Ala Asp Ala Met Met Val Arg Val Val Glu Asp Glu Pro Lys Asp Val
305                 310                 315                 320

Val Glu Phe Leu Ser Met Ile Arg Ile Phe Arg Leu Phe Lys Leu Thr
                325                 330                 335

Gln His His Gln Gly Leu Gln Ile Leu Ile His Thr Phe Arg Ala Ser
            340                 345                 350

Ala Lys Glu Leu Ile Leu Leu Val Phe Phe Leu Ile Leu Gly Ile Val
        355                 360                 365

Ile Phe Ala Ala Leu Val Tyr Tyr Ala Glu Lys Met Glu Ala Asn Pro
        370                 375                 380

Asn Asn Gln Phe Gln Ser Ile Pro Leu Gly Leu Trp Trp Ala Ile Cys
385                 390                 395                 400

Thr Met Thr Thr Val Gly Tyr Gly Asp Met Thr Pro His Thr Ser Phe
                405                 410                 415

Gly Arg Leu Val Gly Ser Leu Cys Ala Val Met Gly Val Leu Thr Ile
            420                 425                 430

Ala Leu Pro Val Pro Val Ile Val Ser Asn Phe Ala Met Phe Tyr Ser
        435                 440                 445

His Asn Gln Ala Arg Asp Lys Leu Pro Lys Arg Arg Arg Val Leu
        450                 455                 460

Pro Val Glu Gln Ile Arg Leu Gln Ala Arg His Ala Ala Val Leu
465                 470                 475                 480

Glu Pro Ser Ala Ser Gln Gly Leu Gly Gly Gln Ala Ile Arg
                485                 490                 495

Arg Arg Asn Met Pro Ile Leu Ile Asp Gln Asn Cys Cys Asp Glu Glu
            500                 505                 510

Asn His Asn His Lys Asp Arg Glu Lys Ser Glu Asn Ser Asp Glu Gly
        515                 520                 525

Thr Asn Ser Ser Ser Thr Thr Gly Val Asp Thr Val Val Lys Leu Gly
        530                 535                 540

Pro Ser Glu Thr Ala Ile Thr Thr Thr Ile Ile Ser
545                 550                 555
```

<210> SEQ ID NO 9
<211> LENGTH: 1196
<212> TYPE: PRT
<213> ORGANISM: Mus musculus

<400> SEQUENCE: 9

-continued

```
Met Glu Leu Glu His Pro Lys Ser Pro Pro Tyr Pro Ser Ser Ser Ser
 1               5                  10                  15

Ser Ser Ser Ser Ser Ser Val His Glu Pro Lys Met Asp Ala Leu Ile
                20                  25                  30

Ile Pro Val Thr Met Glu Val Pro Cys Asp Ser Arg Gly Gln Arg Met
            35                  40                  45

Trp Trp Ala Phe Leu Ala Ser Ser Met Val Thr Phe Phe Gly Gly Leu
         50                  55                  60

Phe Ile Ile Leu Leu Trp Arg Thr Leu Lys Tyr Leu Trp Thr Val Cys
 65                  70                  75                  80

Cys His Cys Gly Gly Lys Thr Lys Glu Ala Gln Lys Ile Asn Asn Gly
                 85                  90                  95

Ser Ser Gln Ala Asp Gly Thr Leu Lys Pro Val Asp Glu Lys Glu Glu
                100                 105                 110

Val Val Ala Ala Glu Val Gly Trp Met Thr Ser Val Lys Asp Trp Ala
                115                 120                 125

Gly Val Met Ile Ser Ala Gln Thr Leu Thr Gly Arg Val Leu Val Val
        130                 135                 140

Leu Val Phe Ala Leu Ser Ile Gly Ala Leu Val Ile Tyr Phe Ile Asp
145                 150                 155                 160

Ser Ser Asn Pro Ile Glu Ser Cys Gln Asn Phe Tyr Lys Asp Phe Thr
                165                 170                 175

Leu Gln Ile Asp Met Ala Phe Asn Val Phe Phe Leu Leu Tyr Phe Gly
            180                 185                 190

Leu Arg Phe Ile Ala Ala Asn Asp Lys Leu Trp Phe Trp Leu Glu Val
        195                 200                 205

Asn Ser Val Val Asp Phe Phe Thr Val Pro Pro Val Phe Val Ser Val
210                 215                 220

Tyr Leu Asn Arg Ser Trp Leu Gly Leu Arg Phe Leu Arg Ala Leu Arg
225                 230                 235                 240

Leu Ile Gln Phe Ser Glu Ile Leu Gln Phe Leu Asn Ile Leu Lys Thr
                245                 250                 255

Ser Asn Ser Ile Lys Leu Val Asn Leu Leu Ser Ile Phe Ile Ser Thr
                260                 265                 270

Trp Leu Thr Ala Ala Gly Phe Ile His Leu Val Glu Asn Ser Gly Asp
        275                 280                 285

Pro Trp Glu Asn Phe Gln Asn Asn Gln Ala Leu Thr Tyr Trp Glu Cys
        290                 295                 300

Val Tyr Leu Leu Met Val Thr Met Ser Thr Val Gly Tyr Gly Asp Val
305                 310                 315                 320

Tyr Ala Lys Thr Thr Leu Gly Arg Leu Phe Met Val Phe Phe Ile Leu
                325                 330                 335

Gly Gly Leu Ala Met Phe Ala Ser Tyr Val Pro Glu Ile Ile Glu Leu
            340                 345                 350

Ile Gly Asn Arg Lys Lys Tyr Gly Gly Ser Tyr Ser Ala Val Ser Gly
            355                 360                 365

Arg Lys His Ile Val Val Cys Gly His Ile Thr Leu Glu Ser Val Ser
370                 375                 380

Asn Phe Leu Lys Asp Phe Leu His Lys Asp Arg Asp Asp Val Asn Val
385                 390                 395                 400

Glu Ile Val Phe Leu His Asn Ile Ser Pro Asn Leu Glu Leu Glu Ala
            405                 410                 415
```

-continued

```
Leu Phe Lys Arg His Phe Thr Gln Val Glu Phe Tyr Gln Gly Ser Val
        420                 425                 430

Leu Asn Pro His Asp Leu Ala Arg Val Lys Ile Glu Ser Ala Asp Ala
        435                 440                 445

Cys Leu Ile Leu Ala Asn Lys Tyr Cys Ala Asp Pro Asp Ala Glu Asp
        450                 455                 460

Ala Ser Asn Ile Met Arg Val Ile Ser Ile Lys Asn Tyr His Pro Lys
465                 470                 475                 480

Ile Arg Ile Ile Thr Gln Met Leu Gln Tyr His Asn Lys Ala His Leu
                485                 490                 495

Leu Asn Ile Pro Ser Trp Asn Trp Lys Glu Gly Asp Ala Ile Cys
                500                 505                 510

Leu Ala Glu Leu Lys Leu Gly Phe Ile Ala Gln Ser Cys Leu Ala Gln
        515                 520                 525

Gly Leu Ser Thr Met Leu Ala Asn Leu Phe Ser Met Arg Ser Phe Ile
        530                 535                 540

Lys Ile Glu Glu Asp Thr Trp Gln Lys Tyr Tyr Leu Glu Gly Val Ser
545                 550                 555                 560

Asn Glu Met Tyr Thr Glu Tyr Leu Ser Ser Ala Phe Val Gly Leu Ser
                565                 570                 575

Phe Pro Thr Val Cys Glu Leu Cys Phe Val Lys Leu Lys Leu Leu Met
                580                 585                 590

Ile Ala Ile Glu Tyr Lys Ser Ala Asn Arg Glu Ser Arg Ile Leu Ile
        595                 600                 605

Asn Pro Gly Asn His Leu Lys Ile Gln Glu Gly Thr Leu Gly Phe Phe
        610                 615                 620

Ile Ala Ser Asp Ala Lys Glu Val Lys Arg Ala Phe Phe Tyr Cys Lys
625                 630                 635                 640

Ala Cys His Asp Asp Val Thr Asp Pro Lys Arg Ile Lys Lys Cys Gly
                645                 650                 655

Cys Arg Arg Leu Ile Tyr Phe Glu Asp Glu Gln Pro Pro Thr Leu Ser
                660                 665                 670

Pro Lys Lys Lys Gln Arg Asn Gly Gly Met Arg Asn Ser Pro Asn Thr
        675                 680                 685

Ser Pro Lys Leu Met Arg His Asp Pro Leu Leu Ile Pro Gly Asn Asp
        690                 695                 700

Gln Ile Asp Asn Met Asp Ser Asn Val Lys Lys Tyr Asp Ser Thr Gly
705                 710                 715                 720

Met Phe His Trp Cys Ala Pro Lys Glu Ile Glu Lys Val Ile Leu Thr
                725                 730                 735

Arg Ser Glu Ala Ala Met Thr Val Leu Ser Gly His Val Val Val Cys
                740                 745                 750

Ile Phe Gly Asp Val Ser Ser Ala Leu Ile Gly Leu Arg Asn Leu Val
        755                 760                 765

Met Pro Leu Arg Ala Ser Asn Phe His Tyr His Glu Leu Lys His Ile
        770                 775                 780

Val Phe Val Gly Ser Ile Glu Tyr Leu Lys Arg Glu Trp Glu Thr Leu
785                 790                 795                 800

His Asn Phe Pro Lys Val Ser Ile Leu Pro Gly Thr Pro Leu Ser Arg
                805                 810                 815

Ala Asp Leu Arg Ala Val Asn Ile Asn Leu Cys Asp Met Cys Val Ile
        820                 825                 830

Leu Ser Ala Asn Gln Asn Asn Ile Asp Asp Thr Ser Leu Gln Asp Lys
```

```
                835                 840                 845
Glu Cys Ile Leu Ala Ser Leu Asn Ile Lys Ser Met Gln Phe Asp Asp
            850                 855                 860
Ser Ile Gly Val Leu Gln Ala Asn Ser Gln Gly Phe Thr Pro Pro Gly
865                 870                 875                 880
Met Asp Arg Ser Ser Pro Asp Asn Ser Pro Val His Gly Met Leu Arg
                885                 890                 895
Gln Pro Ser Ile Thr Thr Gly Val Asn Ile Pro Ile Thr Glu Leu
            900                 905                 910
Val Asn Asp Thr Asn Val Gln Phe Leu Asp Gln Asp Asp Asp Asp
            915                 920                 925
Pro Asp Thr Glu Leu Tyr Leu Thr Gln Pro Phe Ala Cys Gly Thr Ala
    930                 935                 940
Phe Ala Val Ser Val Leu Asp Ser Leu Met Ser Ala Thr Tyr Phe Asn
945                 950                 955                 960
Asp Asn Ile Leu Thr Leu Ile Arg Thr Leu Val Thr Gly Gly Ala Thr
                965                 970                 975
Pro Glu Leu Glu Ala Leu Ile Ala Glu Glu Asn Ala Leu Arg Gly Gly
            980                 985                 990
Tyr Ser Thr Pro Gln Thr Leu Ala Asn Arg Asp Arg Cys Arg Val Ala
            995                 1000                1005
Gln Leu Ala Leu Leu Asp Gly Pro Phe Ala Asp Leu Gly Asp Gly Gly
    1010                1015                1020
Cys Tyr Gly Asp Leu Phe Cys Lys Ala Leu Lys Thr Tyr Asn Met Leu
1025                1030                1035                1040
Cys Phe Gly Ile Tyr Arg Leu Arg Asp Ala His Leu Ser Thr Pro Ser
                1045                1050                1055
Gln Cys Thr Lys Arg Tyr Val Ile Thr Asn Pro Pro Tyr Glu Phe Glu
            1060                1065                1070
Leu Val Pro Thr Asp Leu Ile Phe Cys Leu Met Gln Phe Asp His Asn
        1075                1080                1085
Ala Gly Gln Ser Arg Ala Ser Leu Ser His Ser Ser His Ser Ser Gln
    1090                1095                1100
Ser Ser Ser Lys Lys Ser Ser Ser Val His Ser Ile Pro Ser Thr Ala
1105                1110                1115                1120
Asn Arg Pro Asn Arg Pro Lys Ser Arg Glu Ser Arg Asp Lys Gln Asn
            1125                1130                1135
Ala Thr Arg Met Thr Arg Met Gly Gln Ala Glu Lys Lys Trp Phe Thr
                1140                1145                1150
Asp Glu Pro Asp Asn Ala Tyr Pro Arg Asn Ile Gln Ile Lys Pro Met
        1155                1160                1165
Ser Thr His Met Ala Asn Gln Ile Asn Gln Tyr Lys Ser Thr Ser Ser
    1170                1175                1180
Leu Ile Pro Pro Ile Arg Glu Val Glu Asp Glu Cys
1185                1190                1195

<210> SEQ ID NO 10
<211> LENGTH: 731
<212> TYPE: PRT
<213> ORGANISM: Homo sapiens

<400> SEQUENCE: 10

Met Asp Thr Ser Gly His Phe Asp Ser Gly Val Gly Asp Leu Asp
 1               5                  10                  15
```

-continued

```
Glu Asp Pro Lys Cys Pro Cys Pro Ser Ser Gly Asp Glu Gln Gln Gln
         20                  25                  30
Gln Gln Gln Gln Gln Gln Gln Gln Pro Pro Pro Ala Ser Pro
     35                  40                  45
Ala Ala Pro Gln Gln Pro Leu Gly Pro Ser Leu Gln Pro Gln Pro Pro
         50                  55                  60
Gln Leu Gln Gln Gln Gln Gln Gln Gln Gln Gln Gln Gln Gln Gln
 65                  70                  75                  80
Ser Pro His Pro Leu Ser Gln Leu Ala Gln Leu Gln Ser Gln Pro Val
             85                  90                  95
His Pro Gly Leu Leu His Ser Ser Pro Thr Ala Phe Arg Ala Pro Pro
             100                 105                 110
Ser Ser Asn Ser Thr Ala Ile Leu His Pro Ser Ser Arg Gln Gly Ser
             115                 120                 125
Gln Leu Asn Leu Asn Asp His Leu Leu Gly His Ser Pro Ser Ser Thr
             130                 135                 140
Ala Thr Ser Gly Pro Gly Gly Ser Arg His Arg Gln Ala Ser Pro
145                 150                 155                 160
Leu Val His Arg Arg Asp Ser Asn Pro Phe Thr Glu Ile Ala Met Ser
                 165                 170                 175
Ser Cys Lys Tyr Ser Gly Gly Val Met Lys Pro Leu Ser Arg Phe Ser
             180                 185                 190
Ala Ser Arg Arg Asn Leu Ile Glu Ala Glu Thr Glu Gly Gln Pro Leu
             195                 200                 205
Gln Leu Phe Ser Pro Ser Asn Pro Pro Glu Ile Val Ile Ser Ser Arg
         210                 215                 220
Glu Asp Asn His Ala His Gln Thr Leu Leu His His Pro Asn Ala Thr
225                 230                 235                 240
His Asn His Gln His Ala Gly Thr Thr Ala Ser Ser Thr Thr Phe Pro
                 245                 250                 255
Lys Ala Asn Lys Arg Lys Asn Gln Asn Ile Gly Tyr Lys Leu Gly His
             260                 265                 270
Arg Arg Ala Leu Phe Glu Lys Arg Lys Arg Leu Ser Asp Tyr Ala Leu
         275                 280                 285
Ile Phe Gly Met Phe Gly Ile Val Val Met Val Ile Glu Thr Glu Leu
     290                 295                 300
Ser Trp Gly Leu Tyr Ser Lys Asp Ser Met Phe Ser Leu Ala Leu Lys
305                 310                 315                 320
Cys Arg Ile Ser Leu Ser Thr Ile Ile Leu Leu Gly Leu Ile Ile Ala
                 325                 330                 335
Tyr His Thr Arg Gly Val Gln Leu Phe Val Ile Asp Asn Asp Ala Asp
             340                 345                 350
Asp Trp Arg Ile Ala Met Thr Tyr Glu Arg Ile Leu Tyr Ile Ser Leu
             355                 360                 365
Glu Met Leu Val Tyr Thr Asn His Thr Ile Pro Gly Glu Tyr Lys Phe
         370                 375                 380
Phe Trp Ala Ala Arg Leu Ala Phe Ser Tyr Thr Pro Ser Arg Ala Glu
385                 390                 395                 400
Ala Asp Val Asp Ile Ile Leu Ser Ile Pro Met Phe Leu Arg Leu Tyr
                 405                 410                 415
Leu Ile Ala Arg Val Met Leu Leu His Ser Lys Leu Phe Thr Asp Ala
             420                 425                 430
Ser Ser Arg Ser Ile Gly Ala Leu Asn Lys Ile Asn Phe Asn Thr Arg
```

-continued

```
                435                 440                 445
Phe Val Met Lys Thr Leu Met Thr Ile Cys Pro Gly Thr Val Leu Leu
    450                 455                 460

Val Phe Ser Ile Ser Leu Trp Ile Ile Ala Ala Trp Thr Val Arg Val
465                 470                 475                 480

Cys Glu Arg Tyr His Asp Gln Gln Asp Val Thr Ser Asn Phe Leu Gly
                485                 490                 495

Ala Met Trp Leu Ile Ser Ile Thr Phe Leu Ser Ile Gly Tyr Gly Asp
            500                 505                 510

Met Val Pro His Thr Tyr Cys Gly Lys Gly Val Cys Leu Leu Thr Gly
            515                 520                 525

Ile Met Gly Ala Gly Cys Thr Ala Leu Val Val Ala Val Val Ala Arg
    530                 535                 540

Lys Leu Glu Leu Thr Lys Ala Glu Lys His Val Asp Asn Phe Met Met
545                 550                 555                 560

Asp Thr Gln Leu Thr Lys Arg Ile Lys Asn Ala Ala Asn Val Leu
                565                 570                 575

Arg Glu Thr Trp Leu Ile Tyr Lys His Thr Lys Leu Leu Lys Lys Ile
            580                 585                 590

Asp His Ala Lys Val Arg Lys His Gln Arg Lys Phe Leu Gln Ala Ile
    595                 600                 605

His Gln Leu Arg Ser Val Lys Met Glu Gln Arg Lys Leu Ser Asp Gln
    610                 615                 620

Ala Asn Thr Leu Val Asp Leu Ser Lys Met Gln Asn Val Met Tyr Asp
625                 630                 635                 640

Leu Ile Thr Glu Leu Asn Asp Arg Ser Glu Asp Leu Glu Lys Gln Ile
                645                 650                 655

Gly Ser Leu Glu Ser Lys Leu Glu His Leu Thr Ala Ser Phe Asn Ser
            660                 665                 670

Leu Pro Leu Leu Ile Ala Asp Thr Leu Arg Gln Gln Gln Gln Leu
        675                 680                 685

Leu Ser Ala Ile Ile Glu Ala Arg Gly Val Ser Val Gly Thr
    690                 695                 700

Thr His Thr Pro Ile Ser Asp Thr Pro Ile Gly Val Ser Ser Thr Ser
705                 710                 715                 720

Phe Pro Thr Pro Tyr Thr Ser Ser Ser Cys
                725                 730
```

<210> SEQ ID NO 11
<211> LENGTH: 857
<212> TYPE: PRT
<213> ORGANISM: Arabidopsis thaliana

<400> SEQUENCE: 11

```
Met Arg Gly Gly Ala Leu Leu Cys Gly Gln Val Gln Asp Glu Ile Glu
1               5                   10                  15

Gln Leu Ser Arg Glu Ser Ser His Phe Ser Leu Ser Thr Gly Ile Leu
            20                  25                  30

Pro Ser Leu Gly Ala Arg Ser Asn Arg Arg Val Lys Leu Arg Arg Phe
        35                  40                  45

Val Val Ser Pro Tyr Asp His Lys Tyr Arg Ile Trp Glu Ala Phe Leu
    50                  55                  60

Val Val Leu Val Val Tyr Thr Ala Trp Val Ser Pro Phe Glu Phe Gly
65                  70                  75                  80
```

-continued

```
Phe Leu Arg Lys Pro Arg Pro Leu Ser Ile Thr Asp Asn Ile Val
             85                  90                  95

Asn Ala Phe Phe Ala Ile Asp Ile Ile Met Thr Phe Val Gly Tyr
            100                 105                 110

Leu Asp Lys Ser Thr Tyr Leu Ile Val Asp Asp Arg Lys Gln Ile Ala
            115                 120                 125

Phe Lys Tyr Leu Arg Ser Trp Phe Leu Leu Asp Leu Val Ser Thr Ile
130                 135                 140

Pro Ser Glu Ala Ala Met Arg Ile Ser Ser Gln Ser Tyr Gly Leu Phe
145                 150                 155                 160

Asn Met Leu Arg Leu Trp Arg Leu Arg Arg Val Gly Ala Leu Phe Ala
                165                 170                 175

Arg Leu Glu Lys Asp Arg Asn Phe Asn Tyr Phe Trp Val Arg Cys Ala
                180                 185                 190

Lys Leu Val Cys Val Thr Leu Phe Ala Val His Cys Ala Ala Cys Phe
                195                 200                 205

Tyr Tyr Leu Ile Ala Ala Arg Asn Ser Asn Pro Ala Lys Thr Trp Ile
                210                 215                 220

Gly Ala Asn Val Ala Asn Phe Leu Glu Glu Ser Leu Trp Met Arg Tyr
225                 230                 235                 240

Val Thr Ser Met Tyr Trp Ser Ile Thr Thr Leu Thr Thr Val Gly Tyr
                245                 250                 255

Gly Asp Leu His Pro Val Asn Thr Lys Glu Met Ile Phe Asp Ile Phe
                260                 265                 270

Tyr Met Leu Phe Asn Leu Gly Leu Thr Ala Tyr Leu Ile Gly Asn Met
                275                 280                 285

Thr Asn Leu Val Val His Gly Thr Ser Arg Thr Arg Asn Phe Arg Asp
290                 295                 300

Thr Ile Gln Ala Ala Ser Asn Phe Ala His Arg Asn His Leu Pro Pro
305                 310                 315                 320

Arg Leu Gln Asp Gln Met Leu Ala His Leu Cys Leu Lys Tyr Arg Thr
                325                 330                 335

Asp Ser Glu Gly Leu Gln Gln Gln Glu Thr Leu Asp Ala Leu Pro Lys
                340                 345                 350

Ala Ile Arg Ser Ser Ile Ser His Phe Leu Phe Tyr Ser Leu Met Asp
                355                 360                 365

Lys Val Tyr Leu Phe Arg Gly Val Ser Asn Asp Leu Leu Phe Gln Leu
                370                 375                 380

Val Ser Glu Met Lys Ala Glu Tyr Phe Pro Pro Lys Glu Asp Val Ile
385                 390                 395                 400

Leu Gln Asn Glu Ala Pro Thr Asp Phe Tyr Ile Leu Val Asn Gly Thr
                405                 410                 415

Ala Asp Leu Val Asp Val Asp Thr Gly Thr Glu Ser Ile Val Arg Glu
                420                 425                 430

Val Lys Ala Gly Asp Ile Ile Gly Glu Ile Gly Val Leu Cys Tyr Arg
                435                 440                 445

Pro Gln Leu Phe Thr Val Arg Thr Lys Arg Leu Cys Gln Leu Leu Arg
                450                 455                 460

Met Asn Arg Thr Thr Phe Leu Asn Ile Ile Gln Ala Asn Val Gly Asp
465                 470                 475                 480

Gly Thr Ile Ile Met Asn Asn Leu Leu Gln His Leu Lys Glu Met Asn
                485                 490                 495

Asp Pro Val Met Thr Asn Val Leu Leu Glu Ile Glu Asn Met Leu Ala
```

```
                    500                 505                 510
Arg Gly Lys Met Asp Leu Pro Leu Asn Leu Cys Phe Ala Ala Ile Arg
            515                 520                 525

Glu Asp Asp Leu Leu His Gln Leu Leu Lys Arg Gly Leu Asp Pro
    530                 535                 540

Asn Glu Ser Asp Asn Asn Gly Arg Thr Pro Leu His Ile Ala Ala Ser
545                 550                 555                 560

Lys Gly Thr Leu Asn Cys Val Leu Leu Leu Glu Tyr His Ala Asp
                565                 570                 575

Pro Asn Cys Arg Asp Ala Glu Gly Ser Val Pro Leu Trp Glu Ala Met
            580                 585                 590

Val Glu Gly His Glu Lys Val Val Lys Val Leu Leu Glu His Gly Ser
            595                 600                 605

Thr Ile Asp Ala Gly Asp Val Gly His Phe Ala Cys Thr Ala Ala Glu
            610                 615                 620

Gln Gly Asn Leu Lys Leu Leu Lys Glu Ile Val Leu His Gly Gly Asp
625                 630                 635                 640

Val Thr Arg Pro Arg Ala Thr Gly Thr Ser Ala Leu His Thr Ala Val
                645                 650                 655

Cys Glu Glu Asn Ile Glu Met Val Lys Tyr Leu Leu Glu Gln Gly Ala
            660                 665                 670

Asp Val Asn Lys Gln Asp Met His Gly Trp Thr Pro Arg Asp Leu Ala
            675                 680                 685

Glu Gln Gln Gly His Glu Asp Ile Lys Ala Leu Phe Arg Glu Lys Leu
            690                 695                 700

His Glu Arg Arg Val His Ile Glu Thr Ser Ser Val Pro Ile Leu
705                 710                 715                 720

Lys Thr Gly Ile Arg Phe Leu Gly Arg Phe Thr Ser Glu Pro Asn Ile
                725                 730                 735

Arg Pro Ala Ser Arg Glu Val Ser Phe Arg Ile Arg Glu Thr Arg Ala
            740                 745                 750

Arg Arg Lys Thr Asn Asn Phe Asp Asn Ser Leu Phe Gly Ile Leu Ala
            755                 760                 765

Asn Gln Ser Val Pro Lys Asn Gly Leu Ala Thr Val Asp Glu Gly Arg
            770                 775                 780

Thr Gly Asn Pro Val Arg Val Thr Ile Ser Cys Ala Glu Lys Asp Asp
785                 790                 795                 800

Ile Ala Gly Lys Leu Val Leu Leu Pro Gly Ser Phe Lys Glu Leu Leu
                805                 810                 815

Glu Leu Gly Ser Asn Lys Phe Gly Ile Val Ala Thr Lys Val Met Asn
            820                 825                 830

Lys Asp Asn Asn Ala Glu Ile Asp Asp Val Asp Val Ile Arg Asp Gly
            835                 840                 845

Asp His Leu Ile Phe Ala Thr Asp Ser
850                 855

<210> SEQ ID NO 12
<211> LENGTH: 1159
<212> TYPE: PRT
<213> ORGANISM: Homo sapiens

<400> SEQUENCE: 12

Met Pro Val Arg Arg Gly His Val Ala Pro Gln Asn Thr Phe Leu Asp
1               5                   10                  15
```

-continued

```
Thr Ile Ile Arg Lys Phe Glu Gly Gln Ser Lys Phe Ile Ile Ala
         20                  25                  30

Asn Ala Arg Val Glu Asn Cys Ala Val Ile Tyr Cys Asn Asp Gly Phe
         35                  40                  45

Cys Glu Leu Cys Gly Tyr Ser Arg Ala Glu Val Met Gln Arg Pro Cys
     50                  55                  60

Thr Cys Asp Phe Leu His Gly Pro Arg Thr Gln Arg Arg Ala Ala Ala
 65                  70                  75                  80

Gln Ile Ala Gln Ala Leu Leu Gly Ala Glu Arg Lys Val Glu Ile
                 85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
        130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Ala Gly Ala Pro Gly
            180                 185                 190

Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
```

```
                    435                 440                 445
Cys Gln Pro Leu Ala Val Val Asp Leu Ile Val Asp Ile Met Phe Ile
    450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
Trp Phe Leu Ile Asp Met Val Ala Ala Ile Pro Phe Asp Leu Leu Ile
                500                 505                 510
Phe Gly Ser Gly Ser Glu Glu Leu Ile Gly Leu Leu Lys Thr Ala Arg
            515                 520                 525
Leu Leu Arg Leu Val Arg Val Ala Arg Lys Leu Asp Arg Tyr Ser Glu
            530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
                580                 585                 590
Ile Gly Lys Pro Tyr Asn Ser Ser Gly Leu Gly Gly Pro Ser Ile Lys
            595                 600                 605
Asp Lys Tyr Val Thr Ala Leu Tyr Phe Thr Phe Ser Ser Leu Thr Ser
    610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
                660                 665                 670
Tyr His Thr Gln Met Leu Arg Val Arg Glu Phe Ile Arg Phe His Gln
            675                 680                 685
Ile Pro Asn Pro Leu Arg Gln Arg Leu Glu Glu Tyr Phe Gln His Ala
    690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
                740                 745                 750
Ala Leu Ala Met Lys Phe Lys Thr Thr His Ala Pro Pro Gly Asp Thr
            755                 760                 765
Leu Val His Ala Gly Asp Leu Leu Thr Ala Leu Tyr Phe Ile Ser Arg
    770                 775                 780
Gly Ser Ile Glu Ile Leu Arg Gly Asp Val Val Ala Ile Leu Gly
785                 790                 795                 800
Lys Asn Asp Ile Phe Gly Glu Pro Leu Asn Leu Tyr Ala Arg Pro Gly
                805                 810                 815
Lys Ser Asn Gly Asp Val Arg Ala Leu Thr Tyr Cys Asp Leu His Lys
                820                 825                 830
Ile His Arg Asp Asp Leu Leu Glu Val Leu Asp Met Tyr Pro Glu Phe
            835                 840                 845
Ser Asp His Phe Trp Ser Ser Leu Glu Ile Thr Phe Asn Leu Arg Asp
850                 855                 860
```

-continued

```
Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
            885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
            915                 920                 925

Glu Ser Pro Ser Gly Pro Ser Ser Pro Glu Ser Ser Glu Asp Glu
            930                 935                 940

Gly Pro Gly Arg Ser Ser Ser Pro Leu Arg Leu Val Pro Phe Ser Ser
945                 950                 955                 960

Pro Arg Pro Pro Gly Glu Pro Gly Gly Glu Pro Leu Met Glu Asp
            965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu Asn
    1010                1015                1020

Ile Pro Leu Ser Ser Pro Gly Arg Arg Pro Arg Gly Asp Val Glu Ser
1025                1030                1035                1040

Arg Leu Asp Ala Leu Gln Arg Gln Leu Asn Arg Leu Glu Thr Arg Leu
            1045                1050                1055

Ser Ala Asp Met Ala Thr Val Leu Gln Leu Leu Gln Arg Gln Met Thr
            1060                1065                1070

Leu Val Pro Pro Ala Tyr Ser Ala Val Thr Thr Pro Gly Pro Gly Pro
            1075                1080                1085

Thr Ser Thr Ser Pro Leu Leu Pro Val Ser Pro Leu Pro Thr Leu Thr
            1090                1095                1100

Leu Asp Ser Leu Ser Gln Val Ser Gln Phe Met Ala Cys Glu Glu Leu
1105                1110                1115                1120

Pro Pro Gly Ala Pro Glu Leu Pro Gln Glu Gly Pro Thr Arg Arg Leu
            1125                1130                1135

Ser Leu Pro Gly Gln Leu Gly Ala Leu Thr Ser Gln Pro Leu His Arg
            1140                1145                1150

His Gly Ser Asp Pro Gly Ser
        1155

<210> SEQ ID NO 13
<211> LENGTH: 391
<212> TYPE: PRT
<213> ORGANISM: Rattus norvegicus

<400> SEQUENCE: 13

Met Gly Ala Ser Glu Arg Ser Val Phe Arg Val Leu Ile Arg Ala Leu
  1               5                  10                  15

Thr Glu Arg Met Phe Lys His Leu Arg Arg Trp Phe Ile Thr His Ile
              20                  25                  30

Phe Gly Arg Ser Arg Gln Arg Ala Arg Leu Val Ser Lys Glu Gly Arg
          35                  40                  45

Cys Asn Ile Glu Phe Gly Asn Val Asp Ala Gln Ser Arg Phe Ile Phe
      50                  55                  60

Phe Val Asp Ile Trp Thr Thr Val Leu Asp Leu Lys Trp Arg Tyr Lys
```

```
              65                  70                  75                  80
Met Thr Val Phe Ile Thr Ala Phe Leu Gly Ser Trp Phe Leu Phe Gly
                         85                  90                  95
Leu Leu Trp Tyr Val Val Ala Tyr Val His Lys Asp Leu Pro Glu Phe
                100                 105                 110
Tyr Pro Pro Asp Asn Arg Thr Pro Cys Val Glu Asn Ile Asn Gly Met
                115                 120                 125
Thr Ser Ala Phe Leu Phe Ser Leu Glu Thr Gln Val Thr Ile Gly Tyr
        130                 135                 140
Gly Phe Arg Phe Val Thr Glu Gln Cys Ala Thr Ala Ile Phe Leu Leu
145                 150                 155                 160
Ile Phe Gln Ser Ile Leu Gly Val Ile Ile Asn Ser Phe Met Cys Gly
                165                 170                 175
Ala Ile Leu Ala Lys Ile Ser Arg Pro Lys Lys Arg Ala Lys Thr Ile
                180                 185                 190
Thr Phe Ser Lys Asn Ala Val Ile Ser Lys Arg Gly Gly Lys Leu Cys
            195                 200                 205
Leu Leu Ile Arg Val Ala Asn Leu Arg Lys Ser Leu Leu Ile Gly Ser
        210                 215                 220
His Ile Tyr Gly Lys Leu Leu Lys Thr Thr Ile Thr Pro Glu Gly Glu
225                 230                 235                 240
Thr Ile Ile Leu Asp Gln Thr Asn Ile Asn Phe Val Val Asp Ala Gly
                245                 250                 255
Asn Glu Asn Leu Phe Phe Ile Ser Pro Leu Thr Ile Tyr His Ile Ile
                260                 265                 270
Asp His Asn Ser Pro Phe Phe His Met Ala Ala Glu Thr Leu Ser Gln
            275                 280                 285
Gln Asp Phe Glu Leu Val Val Phe Leu Asp Gly Thr Val Glu Ser Thr
        290                 295                 300
Ser Ala Thr Cys Gln Val Arg Thr Ser Tyr Val Pro Glu Glu Val Leu
305                 310                 315                 320
Trp Gly Tyr Arg Phe Val Pro Ile Val Ser Lys Thr Lys Glu Gly Lys
                325                 330                 335
Tyr Arg Val Asp Phe His Asn Phe Gly Lys Thr Val Glu Val Glu Thr
                340                 345                 350
Pro His Cys Ala Met Cys Leu Tyr Asn Glu Lys Asp Ala Arg Ala Arg
            355                 360                 365
Met Lys Arg Gly Tyr Asp Asn Pro Asn Phe Val Leu Ser Glu Val Asp
        370                 375                 380
Glu Thr Asp Asp Thr Gln Met
385                 390

<210> SEQ ID NO 14
<211> LENGTH: 407
<212> TYPE: PRT
<213> ORGANISM: Homo sapiens

<400> SEQUENCE: 14

Met Asp Gln Asp Val Glu Ser Pro Val Ala Ile His Gln Pro Lys Leu
 1               5                  10                  15
Pro Lys Gln Ala Arg Asp Asp Leu Pro Arg His Ile Ser Arg Asp Arg
                20                  25                  30
Thr Lys Arg Lys Ile Gln Arg Tyr Val Arg Lys Asp Gly Lys Cys Asn
            35                  40                  45
```

```
Val His His Gly Asn Val Arg Glu Thr Tyr Arg Tyr Leu Thr Asp Ile
 50                  55                  60

Phe Thr Thr Leu Val Asp Leu Lys Trp Arg Phe Asn Leu Leu Ile Phe
 65                  70                  75                  80

Val Met Val Tyr Thr Val Thr Trp Leu Phe Phe Gly Met Ile Trp Trp
                 85                  90                  95

Leu Ile Ala Tyr Ile Arg Gly Asp Met Asp His Ile Glu Asp Ser Pro
                100                 105                 110

Trp Thr Pro Cys Val Thr Asn Leu Asn Gly Phe Val Ser Ala Phe Leu
                115                 120                 125

Phe Ser Ile Glu Thr Glu Thr Thr Ile Gly Tyr Gly Tyr Arg Val Ile
                130                 135                 140

Thr Asp Lys Cys Pro Glu Gly Ile Ile Leu Leu Leu Ile Gln Ser Val
145                 150                 155                 160

Leu Gly Ser Ile Val Asn Ala Phe Met Val Gly Cys Met Phe Val Lys
                165                 170                 175

Ile Ser Gln Pro Lys Lys Arg Ala Glu Thr Leu Val Phe Ser Thr His
                180                 185                 190

Ala Val Ile Ser Met Arg Asp Gly Lys Leu Cys Leu Met Phe Arg Val
                195                 200                 205

Gly Asp Leu Arg Asn Ser His Ile Val Glu Ala Ser Ile Arg Ala Lys
                210                 215                 220

Leu Ile Lys Ser Lys Gln Thr Ser Glu Gly Glu Phe Ile Pro Leu Asn
225                 230                 235                 240

Gln Thr Asp Ile Asn Val Gly Tyr Tyr Thr Gly Asp Asp Arg Leu Phe
                245                 250                 255

Leu Val Ser Pro Leu Ile Ile Ser His Glu Ile Asn Gln Gln Ser Pro
                260                 265                 270

Phe Trp Glu Ile Ser Lys Ala Gln Leu Pro Lys Glu Glu Leu Glu Ile
                275                 280                 285

Val Val Ile Leu Glu Gly Met Val Ala Thr Gly Met Thr Cys Gln
                290                 295                 300

Ala Arg Ser Ser Tyr Ile Thr Ser Glu Ile Leu Trp Gly Tyr Arg Phe
305                 310                 315                 320

Thr Pro Val Leu Thr Leu Glu Asp Gly Phe Tyr Glu Val Asp Tyr Asn
                325                 330                 335

Ser Phe His Glu Thr Tyr Glu Thr Ser Thr Pro Ser Leu Ser Ala Lys
                340                 345                 350

Glu Leu Ala Glu Leu Ala Ser Arg Ala Glu Leu Pro Leu Ser Trp Ser
                355                 360                 365

Val Ser Ser Lys Leu Asn Gln His Ala Glu Leu Glu Thr Glu Glu Glu
                370                 375                 380

Glu Lys Asn Leu Glu Glu Gln Thr Glu Arg Asn Gly Asp Val Ala Asn
385                 390                 395                 400

Leu Glu Asn Glu Ser Lys Val
                405

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:channel
      protein central pore signature sequence

<400> SEQUENCE: 15
```

Thr Val Gly Tyr Gly Asp
 1               5

<210> SEQ ID NO 16
<211> LENGTH: 160
<212> TYPE: PRT
<213> ORGANISM: Artificial Sequence
<220> FEATURE:
<223> OTHER INFORMATION: Description of Artificial Sequence:mutated
      prokaryotic kcsa potassium channel protein of
      Streptomyces lividans

<400> SEQUENCE: 16

Met Pro Pro Met Leu Ser Gly Leu Leu Ala Arg Leu Val Lys Leu Leu
 1               5                  10                  15

Leu Gly Arg His Gly Ser Ala Leu His Trp Arg Ala Ala Gly Ala Ala
            20                  25                  30

Thr Val Leu Leu Val Ile Val Leu Leu Ala Gly Ser Tyr Leu Ala Val
        35                  40                  45

Leu Ala Glu Arg Gly Ala Pro Gly Ala Ala Leu Ile Ser Tyr Pro Asp
    50                  55                  60

Ala Leu Trp Trp Ser Val Glu Thr Ala Thr Thr Val Gly Tyr Gly Asp
65                  70                  75                  80

Leu Tyr Pro Val Thr Leu Trp Gly Arg Leu Val Ala Val Val Val Met
                85                  90                  95

Val Ala Gly Ile Thr Ser Phe Gly Leu Val Thr Ala Ala Leu Ala Thr
            100                 105                 110

Trp Phe Val Gly Arg Glu Gln Glu Arg Arg Gly His Phe Val Arg His
        115                 120                 125

Ser Glu Lys Ala Ala Glu Glu Ala Tyr Thr Arg Thr Thr Arg Ala Leu
    130                 135                 140

His Glu Arg Phe Asp Arg Leu Glu Arg Met Leu Asp Asp Asn Arg Arg
145                 150                 155                 160

<210> SEQ ID NO 17
<211> LENGTH: 1161
<212> TYPE: DNA
<213> ORGANISM: Artificial Sequence
<220> FEATURE:
<223> OTHER INFORMATION: Description of Artificial Sequence:nuclec acid
      encoding mutated prokaryotic kcsa potassium
      channel protein of Streptomyces lividans

<400> SEQUENCE: 17
gcatgctggc tcctttggga tcgatccgtc cggttcttct ccggccggcc acctctcgaa     60
ggtgacgctg tcgccgacga gccaccgaca tccgaccgac agccccgac agcgctccta    120 cgcggtgccg acatgacacc gacaccgcag gtcggacgac gggggctcag gcgcgacggg    180
cgcggatcac gacggccgta ccgccgcgac ggcgagcacc gccgcgccgc cgaggagtgg    240
ccgaaggagt gaagatcggt tacgaccgt aaaggagtac ctggcgcacc ggcgcgttgt    300
cgcatcgtcg tcccggccgg tggcggagca tgccacccat gctgtccggt cttctggcca    360
gattggtcaa actgctgctc gggcgccacg gcagtgcgct gcactggagg gccgcgggtg    420
ccgcgacggt cctcctggtg atcgtcctcc tcgcgggctc gtacttggcc gtcctggctg    480
agcgcggcgc accgggcgcg gcgctgatct cgtatccgga cgcgctgtgg tggtccgtgg    540
agaccgcgac gaccgtcggc tacggcgacc tgtaccccgt gactctgtgg ggccggctcg    600
tggccgtggt ggtgatggtc gccgggatca cctccttcgg tctggtgacc gccgcgctgg    660

```
ccacctggtt cgtcggccgg gaacaagagc gccggggcca cttcgtgcgc cactccgaga    720
aggccgccga ggaggcgtac acgcggacga cccgggcgct gcacgagcgt ttcgaccgtt    780
tggagcgaat gctcgacgac aaccgccggt gactccgccg gtgaccgccc gagcgaggcc    840
gcaccgatga gtctgcggcg gttgtgcggt ctacccgtcg acgaagggag cgcaccatgc    900
gcaagatcat catttgcacg ttcctgacgc tggacggcgt catgcaggcg ccgggcggcc    960
cggacgagga cgccgagagc ggcttcgaac acggcggctg cagaagccg gtggacgacg   1020 acgaggtcgg cacggccatc gccggctggt acgaggactc cgacgccatg ctcctcggcc   1080
gcaagaccta cgacatcttc gcgtcgtact ggccgaccgc cgaccccgac aacccgttca   1140
cccatcggat gaacagcatg c                                             1161
```

<210> SEQ ID NO 18
<211> LENGTH: 261
<212> TYPE: PRT
<213> ORGANISM: Homo sapiens

<400> SEQUENCE: 18

```
Ile Tyr Tyr Ala Ile Ser Lys Ser Ile Gly Phe Gly Val Asp Thr Trp
  1               5                  10                  15

Val Tyr Pro Asn Ile Thr Asp Pro Glu Tyr Gly Tyr Leu Ala Arg Glu
             20                  25                  30

Tyr Ile Tyr Cys Leu Tyr Trp Ser Thr Leu Thr Leu Thr Thr Ile Gly
         35                  40                  45

Glu Thr Pro Pro Val Lys Asp Glu Glu Tyr Leu Phe Val Ile Phe
     50                  55                  60

Asp Phe Leu Ile Gly Val Leu Ile Phe Ala Thr Ile Val Gly Asn Val
 65                  70                  75                  80

Gly Ser Met Ile Ser Asn Met Asn Ala Thr Arg Ala Glu Phe Gln Ala
                 85                  90                  95

Lys Ile Asp Ala Val Lys His Tyr Met Gln Phe Arg Lys Val Ser Lys
            100                 105                 110

Gly Met Glu Ala Lys Val Ile Arg Trp Phe Asp Tyr Leu Trp Thr Asn
        115                 120                 125

Lys Lys Thr Val Asp Glu Arg Glu Ile Leu Lys Asn Leu Pro Ala Lys
    130                 135                 140

Leu Arg Ala Glu Ile Ala Ile Asn Val His Leu Ser Thr Leu Lys Lys
145                 150                 155                 160

Val Arg Ile Phe His Asp Cys Glu Ala Gly Leu Leu Val Glu Leu Val
                165                 170                 175

Leu Lys Leu Arg Pro Gln Val Phe Ser Pro Gly Asp Tyr Ile Cys Arg
            180                 185                 190

Lys Gly Asp Ile Gly Lys Glu Met Tyr Ile Ile Lys Glu Gly Lys Leu
        195                 200                 205

Ala Val Val Ala Asp Asp Gly Val Thr Gln Tyr Ala Leu Leu Ser Ala
    210                 215                 220

Gly Ser Cys Phe Gly Glu Ile Ser Ile Leu Asn Ile Lys Gly Ser Lys
225                 230                 235                 240

Met Gly Asn Arg Arg Thr Ala Asn Ile Arg Ser Leu Gly Tyr Ser Asp
                245                 250                 255

Leu Phe Cys Leu Ser
            260
```

<210> SEQ ID NO 19
<211> LENGTH: 690
<212> TYPE: PRT
<213> ORGANISM: Homo sapiens

<400> SEQUENCE: 19

```
Met Lys Leu Ser Met Lys Asn Ile Ile Asn Thr Gln Gln Ser Phe
 1               5                  10                  15

Val Thr Met Pro Asn Val Ile Val Pro Asp Ile Glu Lys Glu Ile Arg
                20                  25                  30

Arg Met Glu Asn Gly Ala Cys Ser Ser Phe Ser Glu Asp Asp Ser
            35                  40                  45

Ala Tyr Thr Ser Glu Glu Ser Glu Asn Glu Asn Pro His Ala Arg Gly
    50                  55                  60

Ser Phe Ser Tyr Lys Ser Leu Arg Lys Gly Gly Pro Ser Gln Arg Glu
65                  70                  75                  80

Gln Tyr Leu Pro Gly Ala Ile Ala Ile Phe Asn Val Asn Asn Ser Ser
                85                  90                  95

Asn Lys Asp Gln Glu Pro Glu Glu Lys Lys Lys Lys Lys Glu Lys
                100                 105                 110

Lys Ser Lys Ser Asp Asp Lys Asn Glu Asn Lys Asn Asp Pro Glu Lys
            115                 120                 125

Lys Lys Lys Lys Lys Asp Lys Glu Lys Lys Lys Glu Glu Lys Ser
130                 135                 140

Lys Asp Lys Lys Glu His His Lys Lys Glu Val Val Ile Asp Pro
145                 150                 155                 160

Ser Gly Asn Thr Tyr Tyr Asn Trp Leu Phe Cys Ile Thr Leu Pro Val
                165                 170                 175

Met Tyr Asn Trp Thr Met Val Ile Ala Arg Ala Cys Phe Asp Glu Leu
            180                 185                 190

Gln Ser Asp Tyr Leu Glu Tyr Trp Leu Ile Leu Asp Tyr Val Ser Asp
            195                 200                 205

Ile Val Tyr Leu Ile Asp Met Phe Val Arg Thr Arg Thr Gly Tyr Leu
210                 215                 220

Glu Gln Gly Leu Leu Val Lys Glu Glu Leu Lys Leu Ile Asn Lys Tyr
225                 230                 235                 240

Lys Ser Asn Leu Gln Phe Lys Leu Asp Val Leu Ser Leu Ile Pro Thr
                245                 250                 255

Asp Leu Leu Tyr Phe Lys Leu Gly Trp Asn Tyr Pro Glu Ile Arg Leu
            260                 265                 270

Asn Arg Leu Leu Arg Phe Ser Arg Met Phe Glu Phe Gln Arg Thr
            275                 280                 285

Glu Thr Arg Thr Asn Tyr Pro Asn Ile Phe Arg Ile Ser Asn Leu Val
290                 295                 300

Met Tyr Ile Val Ile Ile His Trp Asn Ala Cys Val Phe Tyr Ser
305                 310                 315                 320

Ile Ser Lys Ala Ile Gly Phe Gly Asn Asp Thr Trp Val Tyr Pro Asp
                325                 330                 335

Ile Asn Asp Pro Glu Phe Gly Arg Leu Ala Arg Lys Tyr Val Tyr Ser
            340                 345                 350

Leu Tyr Trp Ser Thr Leu Thr Leu Thr Thr Ile Gly Glu Thr Pro Pro
            355                 360                 365

Pro Val Arg Asp Ser Glu Tyr Val Phe Val Val Asp Phe Leu Ile
370                 375                 380
```

```
Gly Val Leu Ile Phe Ala Thr Ile Val Gly Asn Ile Gly Ser Met Ile
385                 390                 395                 400

Ser Asn Met Asn Ala Ala Arg Ala Glu Phe Gln Ala Arg Ile Asp Ala
                405                 410                 415

Ile Lys Gln Tyr Met His Phe Arg Asn Val Ser Lys Asp Met Glu Lys
                420                 425                 430

Arg Val Ile Lys Trp Phe Asp Tyr Leu Trp Thr Asn Lys Lys Thr Val
            435                 440                 445

Asp Glu Lys Glu Val Leu Lys Tyr Leu Pro Asp Lys Leu Arg Ala Glu
        450                 455                 460

Ile Ala Ile Asn Val His Leu Asp Thr Leu Lys Lys Val Arg Ile Phe
465                 470                 475                 480

Ala Asp Cys Glu Ala Gly Leu Leu Val Glu Leu Val Leu Lys Leu Gln
                485                 490                 495

Pro Gln Val Tyr Ser Pro Gly Asp Tyr Ile Cys Lys Lys Gly Asp Ile
                500                 505                 510

Gly Arg Glu Met Tyr Ile Ile Lys Glu Gly Lys Leu Ala Val Val Ala
            515                 520                 525

Asp Asp Gly Val Thr Gln Phe Val Val Leu Ser Asp Gly Ser Thr Phe
530                 535                 540

Gly Glu Ile Ser Ile Leu Asn Ile Lys Gly Ser Lys Ala Gly Asn Arg
545                 550                 555                 560

Arg Thr Ala Asn Ile Lys Ser Ile Gly Tyr Ser Asp Leu Phe Cys Leu
                565                 570                 575

Ser Lys Asp Asp Leu Met Glu Ala Leu Thr Glu Tyr Pro Asp Ala Lys
                580                 585                 590

Thr Met Leu Glu Glu Lys Gly Lys Gln Ile Leu Met Lys Asp Gly Leu
            595                 600                 605

Leu Asp Leu Asn Ile Ala Asn Ala Gly Ser Asp Pro Lys Asp Leu Glu
            610                 615                 620

Glu Lys Val Thr Arg Met Glu Gly Ser Val Asp Leu Leu Gln Thr Arg
625                 630                 635                 640

Phe Ala Arg Ile Leu Ala Glu Tyr Glu Ser Met Gln Gln Lys Leu Lys
                645                 650                 655

Gln Arg Leu Thr Lys Val Glu Lys Phe Leu Lys Pro Leu Ile Asp Thr
                660                 665                 670

Glu Phe Ser Ser Ile Glu Gly Pro Trp Ser Glu Ser Gly Pro Ile Asp
                675                 680                 685

Ser Thr
    690

<210> SEQ ID NO 20
<211> LENGTH: 40
<212> TYPE: PRT
<213> ORGANISM: Drosophila melanogaster

<400> SEQUENCE: 20

Ala Glu Ala Gly Ser Glu Asn Ser Phe Phe Lys Ser Ile Pro Asp Ala
1               5                   10                  15

Phe Trp Trp Ala Val Val Thr Met Thr Thr Val Gly Tyr Gly Asp Met
                20                  25                  30

Thr Pro Val Gly Phe Trp Gly Lys
            35                  40

<210> SEQ ID NO 21
```

```
<211> LENGTH: 40
<212> TYPE: PRT
<213> ORGANISM: Rattus norvegicus

<400> SEQUENCE: 21

Ala Asn His Thr Pro Cys Val Glu Asn Ile Asn Gly Met Thr Ser Ala
 1               5                  10                  15

Phe Leu Phe Ser Leu Glu Thr Gln Val Thr Ile Gly Tyr Gly Phe Arg
            20                  25                  30

Cys Val Thr Glu Gln Cys Ala Thr
        35                  40

<210> SEQ ID NO 22
<211> LENGTH: 42
<212> TYPE: PRT
<213> ORGANISM: Methanococcus jannaschii

<400> SEQUENCE: 22

Glu Ser Val Ile Leu Met Thr Val Glu Gly Trp Asp Phe Phe Thr Ala
 1               5                  10                  15

Phe Tyr Thr Ala Val Val Thr Ile Ser Thr Val Gly Tyr Gly Asp Tyr
            20                  25                  30

Thr Pro Gln Thr Phe Leu Gly Lys Leu Ser
        35                  40

<210> SEQ ID NO 23
<211> LENGTH: 40
<212> TYPE: PRT
<213> ORGANISM: Streptomyces lividans

<400> SEQUENCE: 23

Val Leu Ala Glu Arg Pro Gly Ala Gln Leu Ile Thr Tyr Pro Arg Ala
 1               5                  10                  15

Leu Trp Trp Ser Val Glu Thr Ala Thr Thr Val Gly Tyr Gly Asp Leu
            20                  25                  30

Tyr Pro Val Thr Leu Trp Gly Arg
        35                  40

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence:channel
      protein central pore signature sequence

<400> SEQUENCE: 24

Thr Val Gly Tyr Gly
 1               5

<210> SEQ ID NO 25
<211> LENGTH: 58
<212> TYPE: PRT
<213> ORGANISM: Streptomyces lividans

<400> SEQUENCE: 25

Thr Tyr Pro Arg Ala Leu Trp Trp Ser Val Glu Thr Ala Thr Thr Val
 1               5                  10                  15

Gly Tyr Gly Asp Leu Tyr Pro Val Thr Leu Trp Gly Arg Leu Val Ala
            20                  25                  30

Val Val Val Met Val Ala Gly Ile Thr Ser Phe Gly Leu Val Thr Ala
```

```
            35                  40                  45

Ala Leu Ala Thr Trp Phe Val Gly Arg Glu
        50                  55

<210> SEQ ID NO 26
<211> LENGTH: 58
<212> TYPE: PRT
<213> ORGANISM: Escherichia coli

<400> SEQUENCE: 26

Ser Leu Met Thr Ala Phe Tyr Phe Ser Ile Glu Thr Met Ser Thr Val
 1               5                  10                  15

Gly Tyr Gly Asp Ile Val Pro Val Ser Glu Ser Ala Arg Leu Phe Thr
            20                  25                  30

Ile Ser Val Ile Ile Ser Gly Ile Thr Val Phe Ala Thr Ser Met Thr
        35                  40                  45

Ser Ile Phe Gly Pro Leu Ile Arg Gly Gly
        50                  55

<210> SEQ ID NO 27
<211> LENGTH: 58
<212> TYPE: PRT
<213> ORGANISM: Drosophila melanogaster

<400> SEQUENCE: 27

Ser Ile Pro Asp Ala Phe Trp Trp Ala Val Val Thr Met Thr Thr Val
 1               5                  10                  15

Gly Tyr Gly Asp Met Thr Pro Val Gly Phe Trp Gly Lys Ile Val Gly
            20                  25                  30

Ser Leu Cys Val Ile Ala Gly Val Leu Thr Ile Ala Leu Pro Val Pro
        35                  40                  45

Val Ile Val Ser Asn Phe Asn Tyr Phe Tyr
        50                  55

<210> SEQ ID NO 28
<211> LENGTH: 58
<212> TYPE: PRT
<213> ORGANISM: Homo sapiens

<400> SEQUENCE: 28

Ser Ile Pro Asp Ala Phe Trp Trp Ala Val Val Ser Met Thr Thr Val
 1               5                  10                  15

Gly Tyr Gly Asp Met Tyr Pro Val Thr Ile Gly Gly Lys Ile Val Gly
            20                  25                  30

Ser Leu Cys Ala Ile Ala Gly Val Leu Thr Ile Ala Leu Pro Val Pro
        35                  40                  45

Val Ile Val Ser Asn Phe Asn Tyr Phe Tyr
        50                  55

<210> SEQ ID NO 29
<211> LENGTH: 58
<212> TYPE: PRT
<213> ORGANISM: Homo sapiens

<400> SEQUENCE: 29

Ser Ile Pro Ala Ser Phe Trp Trp Ala Thr Ile Thr Met Thr Thr Val
 1               5                  10                  15

Gly Tyr Gly Asp Ile Tyr Pro Lys Thr Leu Leu Gly Lys Ile Val Gly
            20                  25                  30
```

```
Gly Leu Cys Cys Ile Ala Gly Val Leu Val Ile Ala Leu Pro Ile Pro
            35                  40                  45

Ile Ile Val Asn Asn Phe Ser Glu Phe Tyr
        50                  55
```

<210> SEQ ID NO 30
<211> LENGTH: 58
<212> TYPE: PRT
<213> ORGANISM: Paramecium tetraurelia

<400> SEQUENCE: 30

```
Gln Tyr Leu His Ser Leu Tyr Trp Ser Ile Ile Thr Met Thr Thr Ile
 1               5                  10                  15

Gly Tyr Gly Asp Ile Thr Pro Gln Asn Leu Arg Glu Arg Val Phe Ala
            20                  25                  30

Val Gly Met Ala Leu Ser Ala Val Gly Val Phe Gly Tyr Ser Ile Gly
            35                  40                  45

Asn Ile Asn Ser Ile Tyr Ala Glu Trp Ser
        50                  55
```

<210> SEQ ID NO 31
<211> LENGTH: 58
<212> TYPE: PRT
<213> ORGANISM: Caenorhabditis elegans

<400> SEQUENCE: 31

```
Ser Ile Pro Leu Gly Leu Trp Trp Ala Ile Cys Thr Met Thr Thr Val
 1               5                  10                  15

Gly Tyr Gly Asp Met Thr Pro His Thr Ser Phe Gly Arg Leu Val Gly
            20                  25                  30

Ser Leu Cys Ala Val Met Gly Val Leu Thr Ile Ala Leu Pro Val Pro
            35                  40                  45

Val Ile Val Ser Asn Phe Ala Met Phe Tyr
        50                  55
```

<210> SEQ ID NO 32
<211> LENGTH: 58
<212> TYPE: PRT
<213> ORGANISM: Mus musculus

<400> SEQUENCE: 32

```
Thr Tyr Trp Glu Cys Val Tyr Leu Leu Met Val Thr Met Ser Thr Val
 1               5                  10                  15

Gly Tyr Gly Asp Val Tyr Ala Lys Thr Thr Leu Gly Arg Leu Phe Met
            20                  25                  30

Val Phe Phe Ile Leu Gly Gly Leu Ala Met Phe Ala Ser Tyr Val Pro
            35                  40                  45

Glu Ile Ile Glu Leu Ile Gly Asn Arg Lys
        50                  55
```

<210> SEQ ID NO 33
<211> LENGTH: 58
<212> TYPE: PRT
<213> ORGANISM: Homo sapiens

<400> SEQUENCE: 33

```
Asn Phe Leu Gly Ala Met Trp Leu Ile Ser Ile Thr Phe Leu Ser Ile
 1               5                  10                  15

Gly Tyr Gly Asp Met Val Pro His Thr Tyr Cys Gly Lys Gly Val Cys
```

```
                        20                  25                  30
Leu Leu Thr Gly Ile Met Gly Ala Gly Cys Thr Ala Leu Val Val Ala
            35                  40                  45
Val Val Ala Arg Lys Leu Glu Leu Thr Lys
        50                  55
```

<210> SEQ ID NO 34
<211> LENGTH: 58
<212> TYPE: PRT
<213> ORGANISM: Arabidopsis thaliana

<400> SEQUENCE: 34

```
Arg Tyr Val Thr Ser Met Tyr Trp Ser Ile Thr Thr Leu Thr Thr Val
 1               5                  10                  15
Gly Tyr Gly Asp Leu His Pro Val Asn Thr Lys Glu Met Ile Phe Asp
            20                  25                  30
Ile Phe Tyr Met Leu Phe Asn Leu Gly Leu Thr Ala Tyr Leu Ile Gly
            35                  40                  45
Asn Met Thr Asn Leu Val Val His Gly Thr
        50                  55
```

<210> SEQ ID NO 35
<211> LENGTH: 58
<212> TYPE: PRT
<213> ORGANISM: Homo sapiens

<400> SEQUENCE: 35

```
Lys Tyr Val Thr Ala Leu Tyr Phe Thr Phe Ser Ser Leu Thr Ser Val
 1               5                  10                  15
Gly Phe Gly Asn Val Ser Pro Asn Thr Asn Ser Glu Lys Ile Phe Ser
            20                  25                  30
Ile Cys Val Met Leu Ile Gly Ser Leu Met Tyr Ala Ser Ile Phe Gly
            35                  40                  45
Asn Val Ser Ala Ile Ile Gln Arg Leu Tyr
        50                  55
```

<210> SEQ ID NO 36
<211> LENGTH: 60
<212> TYPE: PRT
<213> ORGANISM: Rattus norvegicus

<400> SEQUENCE: 36

```
Gly Met Thr Ser Ala Phe Leu Phe Ser Leu Glu Thr Gln Val Thr Ile
 1               5                  10                  15
Gly Tyr Gly Phe Arg Phe Val Thr Glu Gln Cys Ala Thr Ala Ile Phe
            20                  25                  30
Leu Leu Ile Phe Gln Ser Ile Leu Gly Val Ile Ile Asn Ser Phe Met
            35                  40                  45
Cys Gly Ala Ile Leu Ala Lys Ile Ser Arg Pro Lys
        50                  55                  60
```

<210> SEQ ID NO 37
<211> LENGTH: 60
<212> TYPE: PRT
<213> ORGANISM: Homo sapiens

<400> SEQUENCE: 37

```
Gly Phe Val Ser Ala Phe Leu Phe Ser Ile Glu Thr Glu Thr Thr Ile
 1               5                  10                  15
```

-continued

```
Gly Tyr Gly Tyr Arg Val Ile Thr Asp Lys Cys Pro Glu Gly Ile Ile
             20                  25                  30

Leu Leu Leu Ile Gln Ser Val Leu Gly Ser Ile Val Asn Ala Phe Met
         35                  40                  45

Val Gly Cys Met Phe Val Lys Ile Ser Gln Pro Lys
     50                  55                  60
```

<210> SEQ ID NO 38
<211> LENGTH: 57
<212> TYPE: PRT
<213> ORGANISM: Homo sapiens

<400> SEQUENCE: 38

```
Glu Tyr Ile Tyr Cys Leu Tyr Trp Ser Thr Leu Thr Leu Thr Thr Ile
 1               5                  10                  15

Gly Glu Thr Pro Pro Val Lys Asp Glu Glu Tyr Leu Phe Val Ile
             20                  25                  30

Phe Asp Phe Leu Ile Gly Val Leu Ile Phe Ala Thr Ile Val Gly Asn
         35                  40                  45

Val Gly Ser Met Ile Ser Asn Met Asn
     50                  55
```

<210> SEQ ID NO 39
<211> LENGTH: 57
<212> TYPE: PRT
<213> ORGANISM: Homo sapiens

<400> SEQUENCE: 39

```
Lys Tyr Val Tyr Ser Leu Tyr Trp Ser Thr Leu Thr Leu Thr Thr Ile
 1               5                  10                  15

Gly Glu Thr Pro Pro Val Arg Asp Ser Glu Tyr Val Phe Val Val
             20                  25                  30

Val Asp Phe Leu Ile Gly Val Leu Ile Phe Ala Thr Ile Val Gly Asn
         35                  40                  45

Ile Gly Ser Met Ile Ser Asn Met Asn
     50                  55
```

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:selectivity
      filter sequence

<400> SEQUENCE: 40

```
Val Gly Tyr Gly
 1
```

<210> SEQ ID NO 41
<211> LENGTH: 36
<212> TYPE: PRT
<213> ORGANISM: Streptomyces lividans

<400> SEQUENCE: 41

```
Glu Arg Gly Ala Pro Gly Ala Gln Leu Ile Thr Tyr Pro Arg Ala Leu
 1               5                  10                  15

Trp Trp Ser Val Glu Thr Ala Thr Thr Val Gly Tyr Gly Asp Leu Tyr
             20                  25                  30

Pro Val Thr Leu
         35
```

```
<210> SEQ ID NO 42
<211> LENGTH: 36
<212> TYPE: PRT
<213> ORGANISM: Drosophila melanogaster

<400> SEQUENCE: 42

Glu Ala Gly Ser Glu Asn Ser Phe Phe Lys Ser Ile Pro Asp Ala Phe
 1               5                  10                  15

Trp Trp Ala Val Val Thr Met Thr Thr Val Gly Tyr Gly Asp Met Thr
            20                  25                  30

Pro Val Gly Phe
            35
```

US 6,641,997 B1

ASSAYS FOR SCREENING COMPOUNDS WHICH INTERACT WITH CATION CHANNEL PROTEINS, MUTANT PROKARYOTIC CATION CHANNEL PROTEINS, AND USES THEREOF

CROSS REFERENCE TO RELATED APPLICATIONS

This Application is a continuation in part of U.S. application Ser. No. 09/054,347 filed Apr. 2, 1998 now abandoned, which is a continuation in part of U.S. application Ser. No. 09/045,529 filed on Mar. 20, 1998 now abandoned, wherein both U.S. Ser. No. 09/054,347 and U.S. Ser. No. 09/045,529 are hereby incorporated by reference in their entireties.

GOVERNMENT RIGHTS CLAUSE

The research leading to the present invention was supported in part with National Institutes of Health Grant GM 43949. The government may have rights in the invention.

FIELD OF INVENTION

The present invention relates to a crystal of a cation channel protein, and methods of using such a crystal in screening potential drugs and therapeutic agents for use in treating conditions related to the function of such channels in vivo.

BACKGROUND OF INVENTION

Although numerous types of channel proteins are known, the main types of ion channel proteins are characterized by the method employed to open or close the channel protein to either permit or prevent specific ions from permeating the channel protein and crossing a lipid bilayer cellular membrane. One important type of channel protein is the voltage-gated channel protein, which is opened or closed (gated) in response to changes in electrical potential across the cell membrane. Another type of ion channel protein are celled mechanically gated channel proteins, for which a mechanical stress on the protein opens or closes the channel. Still another type is called a ligand-gated channel, which opens or closes depending on whether a particular ligand is bound the protein. The ligand can be either an extracellular moiety, such as a neurotransmitter, or an intracellular moiety, such as an ion or nucleotide.

Presently, over 100 types of ion channel proteins have been described, with additional ones being discovered. Basically, all ion channels have the same basic structure regarding the permeation of their specific ion, although different gating mechanisms (as described above) can be used. One of the most common types of channel proteins, found in the membrane of almost all animal cells, permits the specific permeation of potassium ions ($K^+$) across a cell membrane. In particular, potassium ions permeate rapidly across cell membranes through $K^+$ channel proteins (up to $10^8$ ions per second). Moreover, potassium channel proteins have the ability to distinguish among potassium ions, and other small alkali metal ions, such as $Li^+$ or $Na^+$ with great fidelity. In particular, potassium ions are at least ten thousand times more permanent than sodium ions. In light of the fact that both potassium and sodium ions are generally spherical in shape, with radii of about 1.33 Å and 0.95 Å respectively, such selectivity is remarkable.

Broadly, potassium channel proteins comprise four (usually identical) subunits. Presently two major types of subunits are known. One type of subunit contains six long hydrophobic segments (presumably membrane-spanning), while the other type contains two hydrophobic segments. Regardless of what type of subunits are used, potassium channel proteins are highly selective for potassium ions, as explained above.

Among their many functions, potassium channel proteins control the pace of the heart, regulate the secretion of hormones such as insulin into the blood stream, generate electrical impulses underlying information transfer in the nervous system, and control airway and vascular smooth muscle tone. Thus, potassium channels participate in cellular control processes that are abnormal, such as cardiac arrhythmia, diabetes mellitus, seizure disorder, asthma and hypertension, to name only a few.

Although potassium channel proteins are involved in such a wide variety of homeostatic functions, few drugs or therapeutic agents are available that act on potassium channel proteins to treat abnormal processes. A reason for a lack of presently available drugs that act on potassium channel proteins is that isolated potassium channel proteins are not available in great abundance, mainly because an animal cell requires only a very limited number of such channel proteins in order to function. Consequently, it has been very difficult to isolate and purify potassium channel proteins, reducing the amount of drug screening efforts in search of potassium channel protein acting drugs.

Hence, what is needed is accurate information regarding the structure of cation channel proteins so that drugs or therapeutic agents having an appropriate structure to potentially interact with a cation channel protein can be selected.

What is also needed is an ability to overcome the physical limitations regarding the isolation and purification of cation channel proteins, particularly potassium ion channel proteins.

What is also needed is a reliable method of utilizing cation channel proteins in screening potential drugs or agents for their possible use in treating conditions related to the function of cation channel proteins in vivo.

What is also needed are novel methods of using accurate information regarding the structure of cation channel proteins so that drugs or therapeutic agents can be screened for potential activity in treating abnormal control processes of the body.

The citation of any reference herein should not be construed as an admission that such reference is available as "Prior Art" to the instant application.

SUMMARY OF THE INVENTION

There is provided, in accordance with the present invention, a method of preparing a functional cation channel protein for use in an assay for screening potential drugs or other agents which interact with a cation channel protein, which permits the screening of potential drugs or agents that may be used as potential therapeutic agents in treating conditions related to the function of cation channel proteins in vivo.

More specifically, the method comprising the steps of providing a functional cation channel protein, conjugating the functional cation channel protein to a solid phase resin, contacting the potential drug or agent to the functional cation channel protein conjugated to the solid phase resin, removing the functional cation channel protein from the solid phase resin, and determining whether the potential drug or agent is bound to the cation channel protein.

In particular, the present invention extends to a method of preparing a functional cation channel protein for use in an assay as described above, wherein the providing step of the method comprises expressing an isolated nucleic acid molecule encoding the cation channel protein in a unicellular host, such that the cation channel protein is present in the cell membrane of the unicellular host, lysing the unicellular host in a solubilizing solution so that the cation channel protein is solubilized in the solution, and extracting the cation channel protein from the solubilizing solution with a detergent. In a preferred embodiment, the isolated nucleic acid molecule comprises a DNA sequence of SEQ ID NO:17, or degenerate variants thereof, or an isolated nucleic acid molecule hybridizable under standard hybridization conditions to an isolated nucleic acid molecule having a DNA sequence of SEQ ID NO:17, or degenerate variants thereof.

Numerous methods of lysing a unicellular host are known to the skilled artisan, and have applications in the present invention. In a preferred embodiment, lysing the unicellular host in a solubilizing solution comprises sonicating the unicellular host in a protein solubilizing solution comprising 50 mM Tris buffer, 100 mM KCl, 10 mM $MgSO_4$, 25 mg DNAse, 1, 250 mM sucrose, pepstatin, leupeptin, and PMSF, pH 7.5.

Furthermore, a skilled artisan is aware of numerous detergents that can be used to extract an integral membrane bound protein, such as a cation channel protein, from a solubilizing solution described above. Examples of such detergents include SDS, Triton-100, Tween 20, Tween 80, glycerol, or decylmaltoside, to name only a few. Preferably, 40 mM decylmaltoside is used to extract the cation channel protein from the solubilizing solution.

Moreover, numerous solid phase resins to which a functional cation channel protein can be conjugated have applications in a method of preparing a functional cation channel protein for use in an assay, as described above. For example, a solid phase resin comprising insoluble polystyrene beads, PVF, polyethylene glycol, or a cobalt resin, to namely only a few have application in the present invention. Preferably, a cation channel protein is conjugated to a cobalt resin at a protein to resin ratio that allows for saturation of the resin with the cation channel protein. Moreover, after conjugation, the cobalt resin is preferably used to line a column having a volume of about 1 ml.

After the cation channel protein is conjugated to a solid phase resin, it is contacted with a potential drug or agent, which is given an opportunity to bind to cation channel protein.

Subsequently, the cation channel protein is removed from the solid phase resin, and analyzed to determine whether the potential drug or agent is bound thereto. Numerous methods of removing the cation channel protein from the solid phase resin are known to those of ordinary skill in the art. In a preferred embodiment, wherein the solid phase resin is a cobalt resin, the removing step comprises contacting the cation channel protein conjugated to the solid phase resin with an imidazole solution. This solution readily cleaves any bonds conjugating the cation channel protein to the resin, so that the protein can removed from the resin, and collected for further analysis to determine whether the potential drug or agent is bound to the protein.

After the cation channel protein has been removed from the resin, it must be examined to determine whether the potential drug or agent is bound thereto. If bound, the drug or agent may have uses involved in modulation of the function of a cation channel protein in vivo, including uses as a therapeutic agent in treating conditions related to the function of cation channel proteins. Numerous analytical methods are presently available to the skilled artisan for determining whether the potential ligand is bound to the cation channel protein. Examples of such methods include molecular weight analysis with SDS-PAGE, immunoassays using an antibody to the drug or agent, HPLC, or mass spectrometry.

Furthermore, the present invention extends to a method of using a functional cation channel protein in an assay for screening potential drugs or agents which interact with the cation channel protein, wherein the potential drug or agent is a member of a library of compounds, which is contacted to the cation channel protein. Examples of libraries having applications in the present invention include, but are not limited to, a mixture of compounds, or a combinatorial library of compounds. Furthermore, examples of combinatorial compounds having applications in the present invention include, but are not limited to, a phage display library, or a synthetic peptide library, to name only a few.

In another embodiment, the present invention extends to a prokaryotic cation channel protein mutated to mimic a functional eukaryotic cation channel protein. More specifically, Applicant has discovered that all cation channel proteins from all organisms have a conserved structure. Hence, placing mutations in a potassium channel from a prokaryotic organism, for example, can permit the use of the prokaryotic cation channel protein in screening assays for drugs that may interact with specific eukaryotic cation channel proteins. For example, a prokaryotic potassium channel protein can be mutated to mimic a cardiac potassium channel protein, a venous potassium channel protein, or a neuro potassium channel of a human, to name only a few.

Hence, pursuant to the present invention, a prokaryotic potassium channel protein, a prokaroytic sodium channel protein, or a prokaryotic calcium channel protein can be mutated to mimic a eukaryotic cation channel protein.

Examples of prokaryotic organisms from which a prokaryotic cation channel protein can be taken and mutated to mimic a eukaryotic cation channel protein include *E. coli, Streptomyces lividans, Clostridium acetrobutylicum,* or *Staphylcoccus aureus,* to name only a few. Furthermore, such prokaryotic cation channel proteins can comprise an amino acid sequence of SEQ ID Nos: 1, 2, 3, or 7, or conserved variants thereof. In a preferred embodiment, the prokaryotic cation channel protein mutated to mimic a eukaryotic cation channel protein, wherein the prokaryotic cation channel protein in a potassium channel protein from *Streptomyces lividans.*

Furthermore, pursuant to the present invention, a prokaryotic cation channel protein can be mutated to mimic eukaryotic potassium channel protein, a eukaryotic sodium channel protein, or a eukaryotic calcium channel protein. Preferably, the eukaryotic cation channel protein is produced endogenously in a eukaryotic organism, such as an insect or a mammal, for example. More specifically, pursuant to the present invention, a prokaryotic cation channel protein is mutated to mimic a eukaryotic cation channel protein endogenously produced in a eukaryotic organism selected from the group consisting of *Drosophila melanogaster, Homo sapiens, C. elegans, Mus musculus, Arabidopsis thaliana, paramecium tetraaurelia* or *Rattus novegicus,* or having an amino acid sequence comprising SEQ ID Nos: 4, 5, 6, 8, 9, 10, 11, 12, 13, or 14, or conserved variants thereof.

In a preferred embodiment, the present invention extends to a prokaryotic cation channel protein mutated to mimic a functional eukaryotic channel protein, wherein the prokaryotic cation channel protein is a potassium channel protein from *Streptomyces lividans* comprising an amino acid sequence of SEQ ID NO:1 or degenerate variants thereof, and the eukaryotic cation channel is a potassium channel protein comprising an amino acid sequence of SEQ ID NO:4 or conserved variants thereof. As a result, the mutated prokaryotic channel protein comprises an amino acid sequence of SEQ ID NO:16, or conserved variants thereof, which is encoded by an isolated nucleic acid molecule comprising a DNA sequence of SEQ ID NO:17, or degenerate variants thereof.

In another embodiment, the present invention extends to a method of using a crystal of a cation channel protein, as described herein, in an assay system for screening drugs and other agents for their ability to modulate the function of a cation channel protein, comprising the steps of initially selecting a potential drug or agent by performing rational drug design with the three-dimensional structure determined for a crystal of the present invention, wherein the selecting is performed in conjunction with computer modeling. After potential drugs or agents have been selected, a cation channel protein is contacted with the potential drug or agent. If the drug or therapeutic agent has potential use for modulating the function of a cation channel protein, a change in the function of the cation channel after contact with the agent, relative to the function of a similar cation channel protein not contacted with the agent, or the function of the same cation channel protein prior to contact with the agent. Hence, the change in function is indicative of the ability of the drug or agent to modulate the function of a cation channel protein.

Furthermore, the present invention extends to extends to a method of using a crystal of a cation channel protein as described herein, in an assay system for screening drugs and other agents for their ability to modulate the function of a cation channel protein, wherein the crystal comprises a $Na^-$ channel protein, a $K^+$ channel protein, or a $Ca^{2+}$ channel protein.

The present invention further extends to a method of using a crystal of a cation channel protein in an assay for screening drugs other drugs for their ability to modulate the function of a cation channel protein, wherein the crystal of the cation channel protein comprises an amino acid sequence of:

residues 23 to 119 of SEQ ID NO:1 (*Streptomyces lividans*);
residues 61 to 119 of SEQ ID NO:2 (*E. coli*);
residues 61 to 119 of SEQ ID NO:3 (*Clostridium acetrobutylicum*);
residues 61 to 119 of SEQ ID NO:4 (*Drosophila melanogaster*);
residues 61 to 119 of SEQ ID NO:5 (*Homo sapiens*);
residues 61 to 119 of SEQ ID NO:6 (*Homo sapiens*);
residues 61 to 119 of SEQ ID NO:7 (*Paramecium tetraaurelia*);
residues 61 to 119 of SEQ ID NO:8 (*C. elegans*);
residues 61 to 119 of SEQ ID NO:9 (*Mus musculus*);
residues 61 to 119 of SEQ ID NO:10 (*Homo sapiens*);
residues 61 to 119 of SEQ ID NO:11 (*Arabidopsis thaliana*);
residues 61 to 119 of SEQ ID NO:12 (*Homo sapiens*);
residues 61 to 119 of SEQ ID NO:13 (*Rattus novegicus*); or
residues 61 to 119 of SEQ ID NO:14 (*Homo sapiens*); or conserved variants thereof.

In a preferred embodiment of a method of using a crystal of a cation channel protein in an assay for screening drugs or other agents for their ability to modulate the function of a cation channel protein, the crystal comprises a potassium channel protein, comprising amino acid residues 23 to 119 of SEQ ID NO:1, a space grouping of C2, and a unit cell of dimensions of a=128.8 Å, b=68.9 Å, c=112.0 Å, and β=124.6°.

Moreover, it is important to note that a drug's or agent's ability to modulate the function of a cation channel protein includes, but is not limited to, increasing or decreasing the cation channel protein's permeability to the specific cation relative to the permeability of the same or a similar not contacted with the drug or agent, or the same cation channel protein prior to contact with the drug or agent.

In a further embodiment, the present invention extends to a method of using a crystal of a cation channel protein, as set forth herein, in an assay system for screening drugs and other agents for their ability to treat conditions related to the function of cation channel proteins in vivo, and particularly in abnormal cellular control processes related to the functioning of cation channel protein. Such a method comprises the initial step of selecting a potential drug or other agent by performing rational drug design with the three-dimensional structure determined for a crystal of the invention, wherein the selecting is performed in conjunction with computer modeling. After potential drugs or therapeutic agents are selected, a cation channel protein is contacted with the potential drug or agent. If an interaction of the potential drug or other agent with the cation channel is detected, it is indicative of the potential use of the drug or agent to treat conditions related the function of cation channel proteins in vivo. Examples of such conditions include, but are not limited to, cardiac arrhythmia, diabetes mellitus, seizure disorder, asthma or hypertension, to name only a few.

Furthermore, a crystal of a cation channel protein used in the method for screening drugs or agents for their ability to interact with a cation channel comprises an $Na^+$ channel protein, $K^+$ channel protein, or $Ca^{2+}$ channel protein. Hence, the method of the present invention can be used to screen drugs or agents capable of treating conditions related to the function of such channels.

Moreover, the present invention extends to a crystal used in the method for screening drugs or agents for their ability to interact with a cation channel protein comprising an amino acid sequence of:

residues 23 to 119 of SEQ ID NO:1 (*Streptomyces lividans*);
residues 61 to 119 of SEQ ID NO:2 (*E. coli*);
residues 61 to 119 of SEQ ID NO:3 (*Clostridium acetrobutylicum*);
residues 61 to 119 of SEQ ID NO:4 (*Drosophila melanogaster*);
residues 61 to 119 of SEQ ID NO:5 (*Homo sapiens*);
residues 61 to 119 of SEQ ID NO:6 (*Homo sapiens*);
residues 61 to 119 of SEQ ID NO:7 (*Paramecium tetraaurelia*);
residues 61 to 119 of SEQ ID NO:8 (*C. elegans*);
residues 61 to 119 of SEQ ID NO:9 (*Mus musculus*);
residues 61 to 119 of SEQ ID NO:10 (*Homo sapiens*);
residues 61 to 119 of SEQ ID NO:11 (*Arabidopsis thaliana*);

residues 61 to 119 of SEQ ID NO:12 (*Homo sapiens*);
residues 61 to 119 of SEQ ID NO:13 (*Rattus novegicus*); or
residues 61 to 119 of SEQ ID NO:14 (*Homo sapiens*), or conserved variants thereof.

In a preferred embodiment, a crystal used in a method for screening drugs or agents for their ability to interact with a cation channel, comprises amino acid residues 23 to 119 of SEQ ID NO:1, has a space grouping of C2, and a unit cell of dimensions of a=128.8 Å, b=68.9 Å, c=112.0 Å, and β=124.6°.

In yet another embodiment, the present invention extends to a method of using a crystal of a cation channel protein described herein, in an assay system for screening drugs and other agents for their ability to permeate through a cation channel protein, comprising an initial step of selecting a potential drug or other agent by performing rational drug design with the three-dimensional structure determined for the crystal, wherein the selecting of the potential drug or agent is performed in conjunction with computer modeling. After a potential drug or agent has been selected, a cation channel protein can be prepared for use in the assay. For example, preparing the cation channel protein can include isolating the cation channel protein from the membrane of a cell, and then inserting the cation channel protein into a membrane having a first and second side which is impermeable to the potential drug or agent. As a result, the cation channel protein traverses the membrane, such that the extracellular portion of the cation channel protein is located on the firs side of the membrane, and the intracellular portion of the cation channel protein is located on the second side of the membrane. The extracellular portion of the cation channel membrane can then be contacted with the potential drug or agent. The presence of the drug or agent in the second side of the membrane is indicative of the drug's or agent's potential to permeate the cation channel protein, and the drug or agent is selected based on its ability to permeate the cation channel protein.

In addition, a crystal used in a method for screening drugs or agents for their ability to permeate a cation channel can comprise a Na$^+$ channel protein, a K$^+$ protein channel, or a Ca$^{2+}$ protein channel.

Furthermore, the present invention extends to the use of a crystal in an assay system for screening drugs and other agents for their ability to permeate through a cation channel protein, wherein the crystal comprises an amino acid sequence of:

residues 23 to 119 of SEQ ID NO:1 (*Streptomyces lividans*);
residues 61 to 119 of SEQ ID NO:2 (*E. coli*);
residues 61 to 119 of SEQ ID NO:3 (*Clostridium acetrobutylicum*);
residues 61 to 119 of SEQ ID NO:4 (*Drosophila melanogaster*);
residues 61 to 119 of SEQ ID NO:5 (*Homo sapiens*);
residues 61 to 119 of SEQ ID NO:6 (*Homo sapiens*);
residues 61 to 119 of SEQ ID NO:7 (*Paramecium tetraaurelia*);
residues 61 to 119 of SEQ ID NO:8 (*C. elegans*);
residues 61 to 119 of SEQ ID NO:9 (*Mus musculus*);
residues 61 to 119 of SEQ ID NO:10 (*Homo sapiens*);
residues 61 to 119 of SEQ ID NO:11 (*Arabidopsis thaliana*);
residues 61 to 119 of SEQ ID NO:12 (*Homo sapiens*);
residues 61 to 119 of SEQ ID NO:13 (*Rattus novegicus*); or
residues 61 to 119 of SEQ ID NO:14 (*Homo sapiens*); or conserved variants thereof.

In a preferred embodiment, the crystal used in an assay system of the present invention for screening drugs and other agents for their ability to permeate through a cation channel protein comprises amino acid residues 23 to 119 of SEQ ID NO:1, has a space grouping of C2, and a unit cell of dimensions of a=128.8 Å, b=68.9 Å, c=112.0 Å, and β=124.6°.

Naturally, the present invention extends to an isolated nucleic acid molecule encoding a mutant K$^+$ channel protein, comprising a DNA sequence of SEQ ID NO:17, or degenerate variants thereof.

Furthermore, the present invention extends to an isolated nucleic acid molecule hybridizable to an isolated nucleic acid molecule encoding a mutant K$^+$ channel protein under standard hybridization conditions.

Moreover, isolated nucleic acid molecules of the present invention, and described above, can be detectably labeled. Examples of detectable labels having applications in the present invention include, but are not limited to, radioactive isotopes, compounds which fluoresce, or enzymes.

The present invention further extends to an isolated nucleic acid molecule encoding a mutant K$^+$ channel protein, or degenerate variants thereof, comprising an amino acid sequence of SEQ ID NO:16, or conserved variants thereof.

In addition, the present invention extends to an isolated nucleic acid molecule encoding a polypeptide comprising an amino acid sequence of SEQ ID NO:16, or conserved variants thereof, wherein the isolated nucleic acid molecule is hybridizable under standard hybridization conditions to an isolated nucleic acid molecule encoding a K$^+$ channel protein, or degenerate variants thereof.

Furthermore, the present invention extends to a mutant cation channel protein comprising an amino acid sequence of SEQ ID NO:16, or conserved variants thereof.

In addition, the present invention extends to a cloning vector comprising an isolated nucleic acid molecule, or degenerate variants thereof, which encodes a mutant cation channel protein of the present invention, or conserved variants thereof, and an origin of replication. The present invention also extends to a cloning vector comprising an origin of replication and an isolated nucleic acid molecule hybridizable under standard hybridization conditions to an isolated nucleic acid molecule, or degenerate variants thereof, which encodes a mutant cation channel protein of the present invention.

Examples of cloning vectors having applications in the present invention include, but are not limited to, *E. coli*, bacteriophages, plasmids, and pUC plasmid derivatives. More specifically, examples of bacteriophages, plasmids, and pUC plasmid derivatives having applications herein comprise lambda derivatives, pBR322 derivatives, and pGEX vectors, or pmal-c, pFLAG, respectively.

Naturally, the present invention extends to an expression vector comprising an isolated nucleic acid molecule comprising a DNA sequence of SEQ ID NO:17, or degenerate variants thereof, operatively associated with a promoter. In another embodiment, an expression vector comprises an isolated nucleic acid molecule hybridizable under standard hybridization conditions to an isolated nucleic acid comprising a DNA sequence of SEQ ID NO:17, or degenerate variants thereof, operatively associated with a promoter.

Examples of promoters having applications in expression vectors of the present invention comprise immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor.

Furthermore, the present invention extends to a unicellular host transformed or transfected with an expression vector of the present invention. Such a unicellular host can be selected from the group consisting of E. coli, Pseudonomas, Bacillus, Strepomyces, yeast, CHO, R1.1, B-W, L-M, COS1, COS7, BSC1, BSC40, BMT10 and Sf9 cells.

Naturally, the present invention extends to a method of producing a mutant cation channel protein, comprising the steps of culturing a unicellular host transformed or transfected with an expression vector of the present invention under conditions that provide for expression of the isolated nucleic acid molecule of the expression vector and recovering the mutant cation channel protein from the unicellular host. Moreover, such a method can also be used wherein the expression vector comprises a an isolated nucleic acid molecule hybridizable under standard hybridization conditions to an isolated nucleic acid molecule comprising a DNA sequence of SEQ ID NO:17, or degenerative variants thereof, operatively associated with a promoter.

The present invention further extends to an antibody having a mutant cation channel protein of the present invention as an immunogen. More specifically, an antibody of the present invention can be a monoclonal antibody, a polyclonal antibody, or a chimeric antibody. Furthermore, an antibody of the present invention can be detectably labeled. Examples of detectable labels having applications in the present invention include, but are not limited to, an enzyme, a chemical which fluoresces, or a radioactive isotope.

Broadly, the present invention extends to a crystal of a cation channel protein having a central pore, which is found natively in a lipid bilayer membrane of an animal cell, such that the central pore communicates with extracellular matrix and cellular cytosol, wherein the crystal effectively diffracts x-rays to a resolution of greater than 3.2 angstroms.

Moreover, the present invention extends to a crystal of a cation channel protein as described above, wherein the cation channel protein comprises a first layer of aromatic amino acid residues positioned to extend into the lipid bilayer membrane proximate to the interface an extracellular matrix and lipid bilayer membrane, a second layer of aromatic amino acid residues positioned to extend into the lipid bilayer membrane proximate to the interface of cellular cytosol and said lipid bilayer membrane, a tetramer of four identical transmembrane subunits, and a central pore formed by the four identical transmembrane subunits.

Moreover, the present invention extends to a crystal of a cation channel protein described above, wherein each transmembrane subunit comprises an inner transmembrane alpha-helix which has a kink therein, an outer transmembrane alpha-helix, and a pore alpha-helix, wherein each subunit is inserted into the tetramer of the cation channel protein so that the outer transmembrane helix of each subunit contacts the first and second layers of aromatic amino acid residues described above, and abuts the lipid bilayer membrane. Moreover, the inner transmembrane helix of each subunit abuts the central pore of the cation channel protein, contacts the first and second layers of aromatic amino acid residues, is tilted by about 25° with respect to the normal of the lipid bilayer membrane, and is packed against inner transmembrane alpha helices of other transmembrane subunits as the second layer of aromatic amino acid residues forming a bundle of helices at the second layer. The pore alpha-helix of each subunit is located at the first layer of said aromatic amino acid residues, and positioned between inner transmembrane alpha-helices of adjacent subunits, and are directed, in an amino to carboxyl sense, towards the center of the central pore.

Furthermore, the present invention extends to a crystal described above, comprising a cation channel protein having a central pore, which comprises a pore region located at the first layer of aromatic amino acid residues, and connected to the inner and outer transmembrane alpha-helices of said subunits. More particularly, the pore region comprises about 25–45 amino acid residues, a turret connected to the pore alpha-helix and the outer alpha-helix, wherein turret is located at the interface of said extracellular matrix and the lipid bilayer membrane. The pore region further comprises an ion selectivity filter connected to the pore alpha-helix and the inner transmembrane alpha-helix of each subunit. The ion selectivity filter extends into the central pore of the cation channel protein, and comprises a signature amino acid residue sequence having main chain atoms which create a stack of sequential oxygen atoms along the selectivity filter that extend into the central pore, and amino acid residues having side chains that interact with the pore helix. It is the signature sequence which enables a cation channel protein to discriminate among the cation intended to permeate the protein, and other cations, so that only the cation intended to permeate the channel protein is permitted to permeate.

The central pore further comprises a tunnel into the lipid bilayer membrane which communicates with the cellular cytosol, and a cavity located within the lipid bilayer membrane between the pore region and the tunnel, and connected to the them, such that the central pore crosses the membrane.

Furthermore, the structure of all ion channel proteins share common features, which are set forth in the crystal of a cation channel protein described above. Consequently, the present invention extends to a crystal of a cation channel protein having a central pore and structure, as described above, wherein the cation is selected from the group consisting of: $Na^-$, $K^+$, and $Ca^{2+}$. Hence, the present invention extends to crystals of potassium channel proteins, sodium channel proteins, and calcium ion channels, to name only a few. In a preferred embodiment, the crystal of a cation channel protein comprises a crystal of a potassium ion channel protein.

In addition, a crystal of a cation channel protein of a present invention comprises the amino acid sequence of any presently known, or subsequently discovered cation protein channel. Consequently, the present invention extends to a crystal of a cation channel protein having a central pore, which is found natively in a lipid bilayer membrane of an animal cell, such that the central pore communicates with extracellular matrix and cellular cytosol, wherein the crystal comprises an amino acid sequence of:

residues 23 to 119 of SEQ ID NO:1 (*Streptomyces lividans*);
residues 61 to 119 of SEQ ID NO:2 (*E. coli*);
residues 61 to 119 of SEQ ID NO:3 (*Clostridium acetrobutylicum*);
residues 61 to 119 of SEQ ID NO:4 (*Drosophila melanogaster*);
residues 61 to 119 of SEQ ID NO:5 (*Homo sapiens*);
residues 61 to 119 of SEQ ID NO:6 (*Homo sapiens*);
residues 61 to 119 of SEQ ID NO:7 (*Paramecium tetraaurelia*);

residues 61 to 119 of SEQ ID NO:8 (*C. elegans*);
residues 61 to 119 of SEQ ID NO:9 (*Mus musculus*);
residues 61 to 119 of SEQ ID NO:10 (*Homo sapiens*);
residues 61 to 119 of SEQ ID NO:11 (*Arabidopsis thaliana*);
residues 61 to 119 of SEQ ID NO:12 (*Homo sapiens*);
residues 61 to 119 of SEQ ID NO:13 (*Rattus novegicus*); or
residues 61 to 119 of SEQ ID NO:14 (*Homo sapiens*); or conserved variants thereof.

In a preferred embodiment, a crystal of the present invention having a central pore, which is found natively in a lipid bilayer membrane of an animal cell, such that the central pore communicates with extracellular matrix and cellular cytosol, comprises an amino sequence of amino acid residues 23 to 119 of SEQ ID NO:1, has a space grouping of C2, a unit cell of dimensions of a=128.8 Å, b=68.9 Å, c=112.0 Å, and β=124.6°.

Furthermore, the present invention extends to a crystal of a cation channel protein having a central pore, which is found natively in a lipid bilayer membrane of an animal cell, such that the central pore communicates with extracellular matrix and cellular cytosol, wherein the channel protein comprises a signature sequence comprising:

Thr-Val-Gly-Tyr-Gly-Asp            (SEQ ID NO:15).

In another embodiment, the present invention extends to a method for growing a crystal of a cation channel protein having a central pore, which is found natively in a lipid bilayer membrane of an animal cell, such that the central pore communicates with extracellular matrix and cellular cytosol, by sitting-drop vapor diffusion. Such a method of the present invention comprises the steps of providing the cation channel protein, removing a predetermined number of carboxy terminal amino acid residues from the cation channel protein to form a truncated cation channel protein, dissolving the truncated cation channel protein in a protein solubilizing solution, such that the concentration of dissolved truncated channel protein is about 5 to about 10 mg/ml, and mixing equal volumes of protein solubilizing solution with reservoir mixture at 20° C. Preferably, the reservoir mixture comprises 200 mM CaCl$_2$, 100 mM Hepes, 48% PEG 400, pH 7.5, and the protein solution comprises (150 mM KCl, 150 mM Tris, 2 mM DTT, pH 7.5).

Moreover, the present invention extends to a method of growing a crystal of a cation channel protein as described above, wherein a crystal can be grown comprising any kind of cation channel protein. In particular, the present invention can be used to grow crystals of potassium channel proteins, sodium channel proteins, or calcium channel proteins, to name only a few.

Furthermore, the present invention extends to a method of growing a crystal of a cation channel protein, as described herein, wherein the crystal comprises an amino acid sequence of:
residues 23 to 119 of SEQ ID NO:1 (*Streptomyces lividans*);
residues 61 to 119 of SEQ ID NO:2 (*E. coli*);
residues 61 to 119 of SEQ ID NO:3 (*Clostridium acetrobutylicum*);
residues 61 to 119 of SEQ ID NO:4 (*Drosophila melanogaster*);
residues 61 to 119 of SEQ ID NO:5 (*Homo sapiens*);
residues 61 to 119 of SEQ ID NO:6 (*Homo sapiens*);
residues 61 to 119 of SEQ ID NO:7 (*Paramecium tetraaurelia*);
residues 61 to 119 of SEQ ID NO:8 (*C. elegans*);
residues 61 to 119 of SEQ ID NO:9 (*Mus musculus*);
residues 61 to 119 of SEQ ID NO:10 (*Homo sapiens*);
residues 61 to 119 of SEQ ID NO:11 (*Arabidopsis thaliana*);
residues 61 to 119 of SEQ ID NO:12 (*Homo sapiens*);
residues 61 to 119 of SEQ ID NO:13 (*Rattus novegicus*); or
residues 61 to 119 of SEQ ID NO:14 (*Homo sapiens*); or conserved variants thereof.

Numerous methods can be used to provide a cation channel protein, for use in growing a crystal. For example, traditional purification techniques such as gel filtration, HPLC, or immunoprecipitation can be used to purify cation channel proteins from the membranes of numerous cells. In another method, recombinant DNA technology can be used, wherein a nucleic acid molecule encoding the particular cation channel protein can be inserted into an expression vector, which is then used to transfer a unicellular host. After transfection, the host can be induced to express the nucleic acid molecule, and the particular cation channel protein can be harvested from the membrane of the unicellular host.

Moreover, numerous methods are available for removing a predetermined number of carboxy terminal amino acid residues from the cation channel protein to form a truncated cation channel protein. For example, chemical techniques can be used to cleave a peptide bond between two particular amino acid residues in the carboxy terminus of the cation channel protein. In another embodiment, the cation channel protein can be contacted with a proteolytic enzyme, so that the predetermined number of residues from the carboxy terminus are enzymatically removed from the carboxy terminus of the cation channel protein, forming a truncated cation channel protein. In a preferred embodiment, the cation channel protein comprises a potassium channel protein having an amino acid sequence of SEQ ID NO:1, which is contacted with chymotripsin so that residues 1–22 are removed, forming a truncated potassium channel protein comprising an amino acid sequence of residues 23–119 of SEQ ID NO:1.

This invention further provides for a prescreening method for identifying potential modulators of potassium ion channel function comprising the steps of: (i) binding a soluble potassium ion channel protein to a solid support where the ion channel has the scaffold of a two-transmembrane-domain-type potassium ion channel and has a tetrameric confirmation; (ii) contacting the soluble potassium ion channel protein in step i with a compound in an aqueous solution; and, (iii) determining the binding of the compound to the soluble potassium ion channel protein.

In addition, this invention provides for a method of screening for compounds which selectively bind to a potassium ion channel protein comprising: (i) complexing a functional two-transmembrane-domain-type potassium ion channel protein to a solid support; (ii) contacting the complexed protein/solid support with an aqueous solution said solution containing a compound that is being screened for the ability to selectively bind to the ion channel protein; and, (iii) determining whether the compound selectively binds to the ion channel protein with the provisoes that the potassium ion channel protein is in the form of a tetrameric protein; and, when the protein is mutated to correspond to the agitoxin2 docking site of a Shaker K$^+$ channel protein by substituting amino acid residues permitting the mutated protein to bind agitoxin2, the protein will bind agitoxin 2 while bound to the solid support, said substituting of residues being within the 36 amino acid domain defined by −25 to +5 of the selectivity filter where the 0 residue is either the phenylalanine or the tyrosine of the filter's signature sequence selected from the group consisting of glycine-phenylalanine-glycine or glycine-tyrosine-glycine.

In a particular embodiment of the method for screening for compounds as described above, a prokaryote two-transmembrane-domain-type ion channel protein is used, such as from *Steptomyces lividans* especially, the KcsA channel. The channels can be either wild-type or mutated from a wild-type protein. One mutation is confined to the 36 amino acid domain defined by −25 to +5 of the selectivity filter where the 0 residue is either the phenylalanine or the tyrosine of the filter's signature sequence selected from the group consisting of glycine-phenylalanine-glycine or glycine-tyrosine-glycine. The method of this invention includes the use of channel mutations where the protein alteration involves the deletion of a subsequence of the native amino acid sequence and replacement of that native sequence with a subsequence from the corresponding domain of a second and different ion channel protein. The second ion channel protein can be from either a prokaryote or an eukaryote cell.

The methods described above may be conducted using an aqueous solution comprises a nonionic detergent.

In addition to the methods of this invention, the invention further comprises a column having the channel proteins of this invention bound thereto. The proteins are as described herein.

The invention also provides for a non-natural and functional two-transmembrane-domain-type potassium ion channel protein wherein the non-natural protein is mutated in its amino acid sequence from a corresponding natural protein whereby the mutation does not prevent the non-natural protein from binding agitoxin2 when the non-natural protein is further mutated to correspond to the agitoxin2 docking site of a Shaker K$^+$ channel protein said docking site created by substituting amino acid residues selected from within the 36 amino acid domain defined by −25 to +5 of the Shaker K$^+$ selectivity filter where the 0 residue is either the phenylalanine or the tyrosine of the filter's signature sequence selected from the group consisting of glycine-phenylalanine-glycine or glycine-tyrosine-glycine. It is preferred that the non-natural protein so modified will binds to a channel blocking protein toxin with at least a 10 fold increase in affinity over the native ion channel. The non-natural proteins include those mutations described above for use on a solid support to identify modulators of potassium ion function.

The invention further provides for a means to assess the adequacy of the structural conformation of a two-transmembrane-domain-type potassium ion channel protein for high through put assays comprising the steps of: (i) complexing a two-transmembrane-domain-type potassium ion channel protein having a tetrameric form to a non-lipid solid support under aqueous conditions; (ii) contacting the complexed two-transmembrane-domain-type potassium ion channel protein with a substance known to bind to the two-transmembrane-domain-type potassium ion channel protein when bound to lipid membrane wherein the substance also modulates potassium ion flow in that channel protein; and, (iii) detecting the binding of the substance to the complexed two-transmembrane-domain-type potassium ion channel protein. The channel proteins can be wildtype proteins or modified as described above. Optionally the contacting is done in the presence of a non-ionic detergent and the substance for binding is either a channel blocker or other modulator including a toxin.

What's more, the present invention extends to columns having applications in the methods of the invention. In particular, the present invention extends to a column comprising a solid support having bound thereto an ion channel having the scaffold of a two-transmembrane-domain-type potassium ion channel and having a tetrameric confirmation.

Furthermore, the present invention extends to a column as described above, wherein the ion channel is a non-natural and functional two-transmembrane-domain-type potassium ion channel protein wherein the non-natural protein is mutated in its amino acid sequence from a corresponding natural protein. Such a mutation does not prevent the non-natural protein from binding a toxin, such as agitoxin2 when the non-natural protein is further mutated to corresponding to the agitoxin2 docking site of a Shaker K$^+$ channel protein. Numerous means are available to the skilled artisan to create the docking. A particular means to create the docking site comprises substituting amino acid residues selected from within the 36 amino acid domain defined by −25 to +5 of the Shaker K$^+$ selectivity filter where the 0 residue is either the phenylalanine or the tyrosine of the filter's signature sequence selected from the group consisting of glycine-phenylalanine-glycine or glycine-tyrosine-glycine.

Accordingly, it is a principal object of the present invention to provide a crystal comprising a cation channel protein.

It is another object of the present invention to provide a method for growing a crystal comprising a cation channel protein.

It is yet another object of the present invention to utilize information on the structure of a cation channel protein obtained from a crystal of the present invention, in an assay system for screening potential drugs or agents that may interact with a cation channel protein. Interaction of the potential drug or agent with a cation channel protein includes binding to a cation channel protein, or modulating the function of a cation channel protein, wherein modulation involves increasing the function of a cation channel protein to allow more specific cations to cross a cell membrane, or decrease the function of a cation channel protein to limit or prevent specific cations from permeating through the protein and crossing the cell membrane. Such drugs or therapeutic agents may have broad applications in treating a variety of abnormal conditions, such as cardiac arrhythmia, diabetes mellitus, seizure disorder, asthma or hypertension, to name only a few.

It is yet another object of the present invention to provide mutant form of a cation channel protein, preferably a potassium channel protein from *Streptomyces lividans,* which binds to Agitoxin2, a toxin found in scorpion venom, in a manner very similar to that in which eukaryotic potassium channel proteins bind to Agitoxin2. Consequently, a mutant cation channel protein of the present invention mimics a functional eukaryotic potassium channel protein, and can serve as a model therefor in screening potential drugs or agents that may interact with a eukaryotic potassium channel protein.

It is still yet another object of the present invention to provide a method of preparing functional cation channel proteins for use in screen systems for assaying potential drugs or therapeutic agents which may have applications in treating conditions related to the function of cation channel proteins in vivo.

It is yet another object of the present invention to provide mutated prokaryotic cation channel proteins which mimic eukaryotic cation channel proteins. With these mutated prokaryotic cation channel proteins, drugs or other can be screened for potential interaction with cation channel proteins in vivo, and hence, potential use as therapeutic agents in treating conditions related to the function of cation channel proteins in vivo, such as cardiac arrhythmia, diabetes millitus, seizure disorder, asthma or hypertension, to name only a few.

These and other aspects of the present invention will be better appreciated by reference to the following drawings and Detailed Description.

Agitoxin2 mutants. The curves correspond to equation Remaining Bound Fraction=$\{1+\text{Kdhot}/[\text{Thot}]\}*\{1+(\text{Kdhot}/[\text{Thot}])*(1+[\text{Tcold}]/\text{Kdcold})\}^{-1}$ with labeled toxin concentration Thot=0.06 µM, wild type toxin Kdhot=0.62 µM, and competing toxin dissociation constant Kdcold=0.62 µM (wind type), 81 µM (K27A), and 27 µM (N30A). (C) CPK model of Agitoxin2 viewing the interaction surface. Side chains of functionally important amino acids are shown in red (4 of Example II). This figure was prepared using the program GRASP (19 of Example II).

Figure 12A:
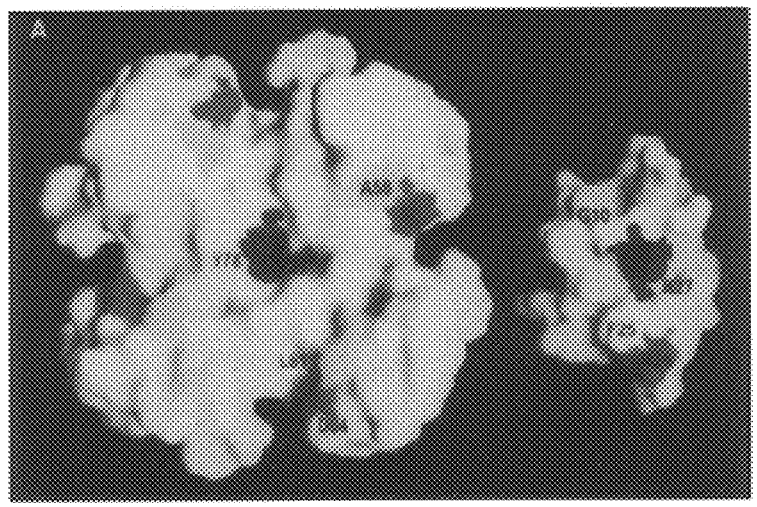

FIG. 12. Docking of Agitoxin2 onto the kesa K+ channel. (A) Molecular surface of the pore entryway of the kesa K+ channel (left) and Agitoxin2 (right). The colors indicate locations of interacting residues on the toxin and channel surfaces as determined by thermodynamic mutant cycle analysis of the Shaker K+ channel-Agitoxin2 interaction (4,8 of Example II). The three pore mutations of the kesa K+ channel used in this study (Q58A. T61S, R64D) were introduced into the channel model using the program O (19 of Example II). Indicated residues on the channel surface correspond to the positions of the Shaker K+ channel equivalent residues (See FIG. 9) which couple to the indicated Agitoxin2 residues. (B) The pattern of colors in (A) suggests the docking orientation shown by the main worm representation of Agitoxin2 placed manually onto the pore entryway. The side chain colors match the colored patches in (A). Gly10 is shown as a green band on the worm. The mutant cycle coupling between residues at Shaker 425 (mutant kesa 58) and residue 10 of Agitoxin2 comes about through substitution of a bulky scale chain residue at either position (4,7 of Example II). Pictures were made using the program GRASP (19 of Example II).

DETAILED DESCRIPTION OF THE INVENTION

The present invention is based on the discovery of a crystal of a cation channel protein, in particular a potassium channel protein from *Streptomyces lividans*, and a method of forming such crystals. Moreover, the present invention is based on the recognition that, based on the structure of the crystalline cation channel protein, potential drugs and therapeutic agents which can bind to cation channel protein can be screened for their use in treating conditions related to function of cation channel proteins, particularly potassium channel proteins, in vivo.

Furthermore, the present invention is based upon the discovery that cation channel proteins from prokaryotic organisms, such as a potassium channel protein from *Streptomyces lividans*, have much similarity and conservation with eukaryotic potassium channel proteins. In particular, a mutated prokaryotic potassium channel protein binds to a particular scorpion toxin in much the same way a eukaryotic potassium channel protein binds to the same toxin.

For purposes of this Application, the term "positioned to extend into the lipid bilayer membrane proximate to the interface . . . " indicates the aromatic side groups of amino acid residues interject into the lipid bilayer membrane from about 0 Å to about 5 Å from the interface of the lipid bilayer with either the extracellular matrix of the cellular cytosol, i.e., the point at which the lipid bilayer membrane meets either the extracellular matrix of the cellular cytosol.

Moreover, for purposes of this Application, the term "kink" indicates the inner transmembrane alph-helix comprises a slight bend in its structure. Moreover, the angle of the tilt of the inner transmembrane helix "normal of the lipid bilayer" indicates the amount of tilt in the inner membrane helix relative to a line perpendicular to the lipid bilayer membrane at a point at which the inner transmembrane alpha-helix would have intersected the lipid bilayer membrane, had the inner transmembrane alpha-helix extended thereto.

Moreover, for purpose of this Application the "specific ion" refers to the ion spaces intended to permeate a particular cation channel protein. For example, if the $K^+$ is the specific ion for a potassium channel protein, $Na^+$ is the specific ion for a sodium channel protein, and $Ca^{2+}$ is the specific ion for calcium channel protein.

Furthermore, an α-helix in a protein is found when a stretch of consecutive residues all have a phi,psi angle pair of approximately −60° and −50°, corresponding to the allowed region of a Ramachandran plot (Branden, C. And Tooze, J. *Introduction to Protein Structure,* Garland Publishing, Inc. New York and London, 1991 p.12 (this reference is incorporated by reference herein in its entirety).

Moreover, the term "bundle" of α-helices, as used herein, refers to the packing at least two α-helices closely together by intercalating side chains of residues of helices in the interation area among them.

The term "stack of sequential oxygen rings" as used herein refers to oxygen atoms of side chains of amino acid residues, such as carbonyl groups, lining a selectivity filter of a cation channel protein which interact with the specific ion in order to permit it to enter the central pore of a cation channel protein, and cross a lipid bilayer membrane.

Further, the term "abut" as used herein indicates an α-helix is adjacent to an the lipid bilayer of a lipid bilayer membrane.

The term describing a protein found "natively in a lipid bilayer membrane" refers to a membrane bound protein, such as a cation channel protein which is in its biologically active conformation, and located in the cellular lipid bilayer membrane.

Further, the term "communicates" refers to connections between individual parts of a central pore of a cation channel portion so that the specific cation is can pass through all individual parts of the central pore, and cross a cellular lipid bilayer membrane via the cation channel protein.

Moreover, the term "agent" as used throughout the instant Application refers to any potential ligand of a cation channel protein, wherein such potential ligands include, but are not limited to, small molecules, both synthetic and naturally occurring, biodegradable cofactors, proteins, synthetic peptides, or polymers, both synthetic and naturally occurring, including DNA.

As used herein, the term "Agitoxin2" refers to a neurotoxin from Leiurus Quinquestriatus Hebraeus which is a scorpion. The amino acid sequence has been identified and the gene has been cloned and expressed. The amino acid sequence is known and available under Accession No. 1065324 in the GenPept Data Base.

Also, as used herein, the phrase "Agitoxin2 docking site" refers to the amino acids which physically interact with Agitoxin2 and are primarily responsible for conferring the ability of a channel protein to bind to Agitoxin2.

As used herein, the term "functional" refers to a channel protein which is in a tetrameric form and having a confirmation that is sufficiently reflective of the native protein in its natural environment so that when a compound binds to the functional channel protein that same compound would also bind to that protein in its natural environment. The test for determining if a channel protein is functional is provided below and relies upon the ability of the protein to bind Agitoxin2 when deliberately mutated to bind the toxin.

"Non-natural" refers to a potassium ion channel protein that has been modified or altered from a corresponding wild type protein. Typically the protein is altered in its primary amino acid sequence bus fusions and chimera to the N and C terminus are included are included as well as addition of non-protein components to available reactive sites.

As used herein, "natural" refers to a potassium ion channel protein which is found in nature. This is referred to as a wildtype.

The term "mutated" as used herein refers to a potassium ion channel protein that has been altered by deletion, substitution of addition of amino acids.

As used herein, the phrase "selectivity filter" refers to the domain of channel ion protein that is responsible for the ability of the protein to exclude one or a group of ions and to allow other ions to pass.

As used herein, the phrase "signature sequence" refers to a sequence of amino acids which define the protein as that protein or as belonging to a group or family of proteins. For specific proteins the signature sequence may be very conserved and be a unique identifier. For signature sequences that define a family, the sequence would be relatively hypervariable but conserved across the family.

Also, as used herein, "solid supports" refer to any non-soluble matrix upon which the potassium ion channel proteins of this invention may be attached.

As used herein, the phrase "structural conformation" refers to a physical relationship between amino acids within a protein. It is a relative state which alters with salt concentration, temperature and hydrophobic nature of the solvent being used. Structural confirmation is best defined by function.

The phrase "tetrameric protein" used herein refers to a protein having quaternary structure comprising 4 subunits which may be the same or different.

As used herein, the phrase "two-transmembrane-domain type potassium ion channel protein" refers to potassium channel monomer having two regions of hydrophobicity with sufficient length to form transmembrane segments. Between these two segments must be found the potassium channel signature sequence. When using the tyrosine or phenylalanine residue of the signature sequence as a zero reference point, the first transmembrane segment would begin within approximately −61 residues of the reference point and the second transmembrane would end within approximately ±42 amino acids of the reference point. To identify the two transmembrane domains one can construct a a Kyte-Dolittle hydropathy plot of the amino acids.

As used herein, the phrase "wild-type" protein refers to a protein such as a potassium ion channel protein which is presented with a primary amino acid sequence that is found in nature.

Isolation of a Functional Cation Channel Protein for Use in Assays to Screen Potential Drugs and Therapeutic Agents This method of the present invention overcomes limitations of using cation channel proteins in the development of drugs or therapeutic agents to treat conditions related to the function of cation channel proteins, and particularly potassium cation channel proteins in vivo, such as cardiac arrhythmia, diabetes mellitus, seizure disorder, asthma or hypertension, to name only a few.

In particular, since cells need very few potassium channels in order to function, it is difficult to isolate functional potassium channels in great quantities. Morever, recombinant techniques to have a cell produce excess potassium channel proteins has met with only limited success. As a result, very few drugs or agents are currently available which act on potassium channel proteins.

However, Applicant has discovered a method to isolate cation channel proteins, particularly potassium cation channel proteins, which can then to be used in efficient assays to screen potential drugs and agents for interaction with such proteins. In particular, disclosed herein is a method of using a functional cation channel protein in an assay for screening for potential drugs or agents that may bind to a cation channel protein comprising, wherein the assay comprises the steps of providing a functional cation channel protein, conjugating the functional cation channel protein to a solid phase resin, contacting the potential drug or agent to the functional cation channel protein conjugated to the solid phase resin, removing the functional cation channel protein from the solid phase resin, and determining whether the potential drug or agent is bonded to the cation channel protein.

Since cation channel proteins are trans membrane bound proteins, care should be taken in their isolation. In particular, to prevent denaturation and a loss of functional activity, they require a hydrophobic environment. In a preferred embodiment, a functional cation channel protein is provided by expressing an isolated nucleic acid molecule encoding the cation channel protein in a unicellular host such that the cation channel protein is present in the cell membrane of the unicellular host, lysing the unicellular host in a stabilizing solutions so that the cation channel protein is solubilized in the solution, and extracting the cation channel protein from the solubilizing solution with a detergent.

Many solubilizing solutions are present known to one of ordinary skill in art, which can solubilize a cation channel protein, and prevent its denaturation or proteolytic digestion. All such solutions are encompassed by the present invention. In a preferred embodiment, the solubilizing solution comprises Tris buffer, 100 mM KCl, 10 mM $MgSO_4$, 25 mg DNAse 1, 250 mM sucrose, pepstrain, leupeptin, and PMSF at PH 7.5.

Moreover, many detergents are available to the skilled artisan for extracting solubilized caton channel protein from a solubilizing solution of the present invention. Examples of detergents having applications herein include SDS, Triton 100, glycerol, decylmaltoside, Tween-20, or Tween-80, to name only a few. In a few preferred embodiment, a 40 mM decylmaltoside is used to extract the cation channel protein from a solubilizing solution of the present invention.

Furthermore, Applicant has discovered that cation channel proteins, particularly potassium cation channel proteins, can be conjugated chemically to a solid phase resin. As a result, the channel proteins are immobilized and readily available in assays for screening drugs or agents that may bind to a cation channel protein. In a preferred embodiment, a cation channel protein is conjugated to a cobalt resin through a carboxyl terminal hexahistidine tag.

In a preferred embodiment, cation channel proteins are conjugated to a cobalt resin at a protein to resin ratio that allows for saturation of the resin with the cation channel protein. As a result, numerous cation channel proteins are immobilized and available for contact with a potential drug or therapeutic agent to be screened pursuant to the present invention.

Moreover, numerous screening methods are available and encompassed by the present invention. For example, the resin with the cation channel conjugated thereto can be incubated in a solution comprising the potential drug or therapeutic agent. In another embodiment, the resin can be used to line a column, to which the potential drug or agent is added. Preferably, a potassium ion channel protein from *Streptomyces lividans* comprising an amino acid sequence of SEQ ID NO:1, or conserved variants thereof, is mutated to mimic a eukaryotic potassium channel, such as a potassium channel protein of *Drosophila melanogaster* comprising an amino acid sequence of SEQ ID NO:4, or conserved variants. Consequently, the mutated potassium channel protein of *Streptomyces lividans* comprising an amino acid sequence of SEQ ID NO:16 is conjugated to a cobalt resin, which is then used to line a 1 ml column. A composition comprising the potential drug or agent to be screened for interaction with a eukaryotic cation channel protein is then poured into the column, so that the potential drug or agent can contact the mutated prokaryotic cation channel protein conjugated to the cobalt membrane.

After contact, the cation channel proteins are removed from the resin, and examined for interaction binding with the potential drug or agent. Numerous methods of cleaving a protein from a solid phase are available to the skilled artisan, and included in the present invention. In a preferred embodiment, the removing step comprises contacting the cation channel protein conjugated to the resin to an imidazole solution. The cation channel proteins can then be collected, and examined for interaction, i.e. binding, with the potential drug or therapeutic agent.

Furthermore, determining whether the drug or therapeutic agent is bound to the cation channel protein can be done with numerous methods. For example, molecular weight determinations can be amide with SDS-PAGE comparing the molecular weight of the cation channel protein not contacted with the drug, to the molecule weight of the cation channel protein contacted with the drug. Furthermore, other analytical methods, such as HPLC, mass spectrometry, or spectrophotometry, to name only a few, can be used to determine whether the drug or agent is bound to a cation channel protein previously conjugated to a solid phase resin.

Moreover, screening potential drugs or agents which may bind a cation channel protein may be performed on an individual basis, i.e. one potential drug or agent at a time, or the present invention can be used to screen whole libraries of compounds at one time, such as a mixture of compounds or a combinatorial library, for potential drugs or agents which potentially bind to a cation channel protein. For example, combinatorial libraires which can be screened with the present invention include, but are not limited to, a phage display library, in which numerous proteins and polypeptides are being express simultaneously, libraries comprising synthetic peptides.

Two-transmembrane-domain Type Potassium Ion Channel Proteins

As set forth above, two-transmembrane type potassium ion channel proteins are well known and structurally constitute one of the classes of potassium channels. They are found in a wide variety of organisms, both prokaryotic and eukaryotic where they serve the purpose of controlling the influx or efflux of potassium ions across cell membranes. Potassium channels as a class are tetrameric membrane proteins characterized by multiple transmembrane segments and a pore region through which potassium ions flow. These channels may be homotetrameric, that is, consisting of four identical monomers, or heterotetrameric, consisting of four monomers which are not necessarily identical. The individual monomers of the heterotetrameric forms are usually structurally related, and may or may not form a functional potassium channel when reconstructed as homotetramers of themselves. The pore region contains a signature sequence consisting of glycine-tyrosine-glycine or glycine-phenylalanine-glycine. Each monomer in the tetrameric structure contributes to the formation of the pore region, and each subunit contains a signature sequence.

To identify a putative protein as a two-transmembrane potassium channel monomer, a Kyte-Dolittle hydropathy plot of the amino acid may be constructed, and it should demonstrate two regions of hydrophobicity with sufficient length to form transmembrane segments. Between these segments must be found the potassium channel signature sequence. When using the tyrosine or phenylalanine residue of the signature sequence as a zero reference point, the first transmembrane segment would begin within approximately −61 residues of the reference point and the second transmembrane region would end within approximately +42 amino acids of the reference point.

Potassium channel monomer subunits may be obtained by a variety of methods, including cloning by nucleic acid hybridization, cloning by antibody selection of expressed proteins, and using the polymerase chain reaction (PCR) with homologous or degenerate primer sets. One of skill in the art would be able to readily obtain DNA sequence encoding such potassium channels given a known DNA sequence or an antibody against the channel itself.

Examples of proteins which have been cloned and identified as two-transmembrane potassium ion channels include IRK3 as described in Koyama H. et Al., Molecular cloning, functional expression and localization of a novel inward rectifier potassium channel in the rat brain. FEBS Lett 341:303-7 1994; IRK3 as described in Morishige et al., Molecular clonging and functional expression of a novel brain-specific inward rectifier potassium channel. FEBS Lett 346: 251-6, 1994; UKATP reported in Inagaki et al., Cloning and functional characterization of a novel ATP-sensitive potassium channel ubiquitously expressed in rat tissues, including pancreatic islets, pituitary, skeletal muscle, and heart. J Biol Chem 270:5691–4; and GIRK2 reported in Ferrer et al., Pancreatic islet cells express a family of inwardly rectifying K+ channel subunits which interact to form G-protein-activated channels. J Biol Chem 270:26086–91 1995.

Mutations of Two-transmembrane-domain Type Potassium Ion Channel Proteins

The present invention further extends to introducing Agitoxin2 docking sites into two-transmembrane-domain type potassium ion channel protein. Any two transmembrane cation channel protein presently known, or subsequently discovered, can routinely be modified to bind agitoxin2 using the protocols described infra. As explained herein, scorpion toxins, such as agitoxin2, bind to an ion channel by making contact with all four subunits where they come together to form the pore. Hence, such toxins will only bind to the channel if the subunits have been properly assembled. As a result, the binding of toxin, such as agitoxin2, to a non-natural two transmembrane cation channel protein can be used to confirm the template channel integrity or function, i.e., to conform the two-transmembrane cation channel protein has been properly modified to mimic a functional eukaryotic two-transmembrane cation channel protein.

The general method for creating an agitoxin (or related scorpion toxin) binding site on the template channel is now described. Particular examples of pore region sequences (toxin binding sequences) of four two-transmembrane cation channel proteins having applications in the present invention are described below:

Shaker aeagsensffksipdafwwavvtmttvgygdmtpvgfwgk (SEQ ID NO:20)

Romk1 anhtpcveningmtsaflfsletqvtigygfrcvteqcat (SEQ ID NO:21)

Mjan esvilmtvegwdfftafytavvtistvgyggdytpqttflgkis (SEQ ID NO:22)

KcsA vlaerpgaqlitypralwwsvetattvgygdlypvtlwgr (SEQ ID NO:23)

Shaker is a six membrane spanning K channel from *Drosophila melanogaster*, ROMK1 is a two membrane-spanning K channel from rat renal outer medulla (kidney). Mjan is a two membrane-spanning K channel from *Methanococcus jannaschii*, and KcsA is a two membrane-spanning K channel from the bacterium *Streptomyces lividans*.

As explained herein, cation channel proteins have a high degree of sequence conservation, particularly in the region of the selectivity filter. Hence, gyg sequence should be used as a reference to align the sequences. The underlined amino acids on the Shaker channel sequence are known to be important for binding of agitoxin, as described infra. In particular, described herein is the mutating of several of the underlined amino acids, using standard techniques. As a result of these mutations, the KcsA K channel because sensitive to agitoxin binding. Similarly, other channels can be subjected to the same analysis. Therefore, using the teachings set forth infra. Mjan or Romk1 channels can readily be modified by those of ordinary skill. Numerous techniques are readily available to the skilled artisan to convert the appropriate (underlined) amino acids of the pore regions of the two-transmembrane cation channel proteins described above the amino acid residues found in the corresponding position of the Shaker K channel. A particular technique which can be in this modification process is directed mutagensis.

Also, the present invention involves introducing mutations into the two-transmembrane-domain type potassium ion channel protein which allow it to mimic other potassium ion channel proteins. In particular, the present invention contemplates the use of two-transmembrane proteins as a scaffold for studying or identifying modulators of potassium ion channel function. The proteins can be modified in a variety of different ways to mimic or simulate properties of related potassium ion channels including conferring properties found in six membrane domain type ion channels. Accordingly, one can create channel proteins that have been minimally altered from their corresponding wild type for convenience of purification, i.e. removing protease cleavage sites in noncritical domains, or attaching binding domains to facilitate chromatographic purifications such as FLAG and polyHis. Because the overall structure of potassium ion proteins is conserved, modifications can be introduced that can transfer properties of one channel protein to the two-transmembrane proteins that is being used as a scaffold. Among these modifications are venom docking sites as exemplified herein as well as binding sites for modulators such as to the transmembrane domains and alterations to the ion filter region.

Recombinant genetics has a variety of techniques for introducing and for determining the domains and in many cases the specific amino acids which are responsible for the physical properties of channel proteins. In brief, these methods consists of manipulating the amino acid sequence of a protein in order to identify which part of the protein is involved in the structure or function of the molecule and then transferring that domain and its properties to proteins that do not naturally have that property. These methods have already been widely applied to the study of ion channels. The study of ion channels lends itself very well to such methods, because these proteins exist in a number of functional families within which are numerous structurally related to yet biophysically and pharmacologically distinct subfamily members. For example, the superfamily of potassium channels all share the pore signature sequence gly-tyr-gly or gly-phe-gly, and are tetrameric; subfamily monomers may have two transmembrane segments of 6 transmembrane segments, and may be gated by membrane potential, intracellular calcium concentration, intracellular cyclic nucleotides, membrane deformation, and pH; they may be inwardly rectifying, outwardly rectifying, or nonrectifying; and their activation and inactivation kinetics, and conductances may vary tremendously.

As exemplified in this application, a number of scorpion and bee venom toxins can bind with high affinity to one subfamily member while being inactive on a closely related subfamily members. It is therefore not surprising that amino acid sequence mutations which confer the properties of one ion channel upon another are a tool which has been commonly employed by ion channel researches and this invention takes advantage of this plieomorphic property in the super family of potassium channels.

Mutations may be introduced using a number of approaches, each with its own particular strengths. Often a combination of these may be used to generate a channel with altered properties. Examples of these approaches are deletions of amino acids, domain replacement of one channel with that of a different channel (chimeras), replacement of amino acids with different amino acid in a nontargeted or semi-targeted way (e.g. alanine-scanning mutagenesis) and replacement of targeted amino acids with different amino acids (site-directed mutagenesis). Although each method may be applied independently, oftentimes several or all of these may be employed to arrive at mutant channel with the desired characteristics. Examples of changed characteristics include channel gating, voltage response, rectification, ion preference, and the binding of small organic molecules and peptides to the channel.

Mutagenesis is especially powerful when an ion channel with novel toxin or small organic molecule-binding characteristics is required. Using this approach, channels which do not show significant binding of a particular toxin or small organic molecule may be engineered to bind strongly to these molecules. Conversely, channels which strongly bind a particular toxin or small organic molecule may be engineered to lose that property.

Examples of the use of the chimeric and site-directed approach are many. In Ishii, T. M., Maylie, J. and Adelman, J. P. (1997) J. Biol. Chem. 272: 23195–200, the authors were able to confer apamin sensitivity on a channel which did not possess this property. Similar studies have been performed on the Kv1.3 and Kv2.1 potassium channels by Gross et al. (1994), Neuron 13: 961–6. In their study, they transferred scorpion toxin sensitivity from the highly sensitive Kv1.3 potassium channel to the insensitive Kv2.1 potassium channel by transferring the stretch of amino acids between transmembrane domains 5 and 6. Conversely, alanine-scanning mutagenesis was used by Hanner et al. (1998), J Biol Chem 273: 16289–96, to impair charybdotoxin binding to the max-K channel, and direct point mutations were employed by Wang and Wang (1998), Proc Natl Acad Sci U S A 95:2653–8, to remove batrachotoxin sensitivity from sodium channels.

Mutagenesis may also be employed to alter the biophysical properties of ion channels, in effect causing one channel to have characteristics similar to those of another. For example, voltage-gated potassium channels of the Shaker subfamily open in response to changes in membrane potential. Members of this subfamily of potassium channels have the intrinsic property of opening a different membrane potentials depending on the particular family member, and have the characteristics of delayed rectification. Limam et al., (1991) Nature, 353:752–6, were able to demonstrate that mutations in the S4 voltage sensor domain of Shaker changed the opening potential; by mutating several amino acid residues in the S4 voltage sensor domain of Shaker, Miller and Aldrich (1996), Neuron 16:853–8, were able to convert this channel from a delayed rectifier into a voltage-gated inward rectifier, Chimeric constructs may use related domains from different channel types. The rat CNG olfactory channel is a member of the voltage-gated subfamily of potassium channels, but is itself voltage-independent and is not entirely selective for potassium ions as compared with the eag channel. Tang and Papazian (1997), J Gen Physiol, 109:301–11, were able to convert the human eag potassium channel from a voltage sensitive to a voltage-independent channel by substituting the S3–S4 domain of the rat cyclic-nucleotide gated (CNG) olfactory channel.

It is therefore clear that mutagenesis may be readily used to confer the pharmacologically and biophysical properties of one channel upon another, and that this methodology applies to not only potassium, but sodium and calcium channels.

Determining if the two-transmembrane-domain type potassium ion channel protein has maintained function using Agitoxin2 binding. Beyond the ability of the channel proteins of this invention to pass ions under ex vivo conditions of using liposomes, their functional can measured by the ability to be modified to accept or recognize agitoxin2. To accomplish this one follows the mutagenesis methods described above both generically for mutation of any channel protein and for the introduction of an angitoxin2 docking site into any two transmembrance-type domain potassium ion channel protein.

Once mutated, the proteins are tested by any number of binding assay formats including homogeneous assays where both agitoxin2 and the channel protein are free in solution and heterogeneous assay formats where one of the binding members is bound to a solid support. Either member can be labelled using the labels described herein. The preferred method for assaying for agitoxin2 binding uses the cobalt resin and procedures described in Example II.

Binding the Two-Transmembrane-Domain Type Potassium Ion Channel Protein to Solid Supports The potassium channels of the invention can be bound to a variety of solid supports. Solid supports of this invention include membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. A preferred solid support uses a cobalt or nickel column which binds with specificity to a histadine tag engineered onto the channel proteins.

Adhesion of the channel proteins of the solid support can be direct (i.e. the protein contacts the solid support) or indirect (a particular compound or compounds are bound to the support and the target protein binds to this compound rather than the solid support). One can immobilize channel proteins either covalently (e.g., utilizing single reactive thiol groups of cysteine residues (see, e.g., Colliuod et al. *Bioconjugate Chem.* 4:528–536 (1993)) or non-covalently but specifically (e.g., via immobilized antibodies (Schuhmann et al. *Adv. Mater.* 3:388–391 (1991); Lu et al. *Anal. Chem.* 67:83–87 (1995), the biotin/strepavidin system (Iwane et al. *Biophys. Biochem. Res. Comm.* 230:76–80 (1997) or metal chelating Langmuir-Blodgett films (Ng et al. *Langmuir* 11:4048–55 (1995); Schmitt et al. *Angew. Chem. Int. Ed. Engl.* 35:317–20 (1996); Frey et al. *Proc. Natl. Acad. Sci. USA* 93:4937–41 (1996); Kubalek et al. *J. Struct. Biol.* 113:117–123 (1994)) and metal-chelating self-assembled monolayers (Sigal et al. *Anal. Chem.* 68:490–497 (1996)) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochoride (DMP); and dimethyl suberimidate dihydrochloride (DMS).

Heterobifunctional reagents include commercially available active halogen-NHS active esters coupling agents such as N-succinimidyl bromoacetate and N-succinimidyl(4-iodoacetyl)aminobenzoate (SIAB) and the sulfosuccinimidyl derivatives such as sulfosuccinimidly (4-iodoacetyl)aminobenzoate (sulfo-SIAB) (Pierce). Another group of coupling agents is the heterobifunctional and thiol cleavable agents such as N-succinimidyl-3-(2-pyridyldithio)propionate (SPDP) (Pierce).

Antibodies are also available for binding channel proteins to a solid support. This can be done directly by binding channel protein specific antibodies to the column and allowing channel proteins to bind or it can be done by creating chimeras constructed from the channel protein linked to an appropriate immunoglobulin constant domain sequence. They are termed immunoadhesins and they are known in the art. Immunoadhesins reported in the literature include Gascoigne et al., *Proc. Natl. Acad. Sci. USA* 84,. 2936–2940 (1987), Capon et al., *Nature* 377, 525–531 (1989); and Traunecker et al., *Nature* 33, 68–70 (1989).

By manipulating the solid support and the mode of attachment of the target molecule to the support, it is possible to control the orientation of the target molecule. Thus, for example, where it is desirable to attach a target molecule to a surface in a manner that leaves the molecule tail free to interact with other molecules, a tag (e.g. FLAG, myc. GST, polyHis. etc.) may be added to the target molecule at a particular position in the target sequence.

It is possible to reconstitute of channels in lipid, membranes or liposomes. For example the following references teach how to reconstitute the channel proteins of this invention in membranes. The very channels of this invention, SliK, the K+ channel encoded by the Streptomyces KcsA gene, was expressed, purified, and reconstituted in liposomes. See, Heginbotham L et al. *J Gen Physiol* 1998 Jun;111(6):741–9 and in Cuello LG, et al., *Biochemistry* 1998 Mar 10;37(10):3229–36.In Shin, JH et al., *FEBS Lett* 1997 Oct 6;415(3):299–302 where the authors demonstrated that nitric oxide could activate a calcium-activated potassium channel from rat using the planar lipid bilayer technique. Santacruz-Toloza L. et al., *Biochemistry* 1994 Feb 15;33(6):1259–9.

Assays

Once bound there are a variety of assay formats that can be used to screen for modulators of the channel proteins. Various molecules that interact with a potassium channel can be identified by 1) attaching the potassium channel ("the target") to a solid support, 2) contacting a second molecule with the support coated with the potassium channel, and 3) detecting the binding of the second molecule to the potassium channel. Molecules that interact or bind with the target are then eluted, with or without the target, thereby isolating molecules that interact with the target.

For a general description of different formats for binding assays, see BASIC AND CLINICAL IMMUNOLOGY, 7$^{th}$ Ed. (D. Stiles and A Terr. ed.)(1991); ENZYME IMMUNOASSAY. E. T. Maggio, ed., CRC Press, Boca Raton, Fla. (1980); and "Practice and Theory of Enzyme Immunoassays" in P. Tijssen, LABORATORY TECHNIQUES IN BIOCHEMISTRY AND MOLECULAR BIOLOGY, Elsevier Science Publishres, B. V. Amsterdam (1985), each of which is incorporated by reference.

In competitive binding assays, the test compound competes with a second compound for specific binding sites on a target molecule attached to the solid support. Binding is determined by assessing the amount of second compound associated with the target molecule. The amount of second compound associated with the target molecule is inversely proportional to the ability of a test compound to compete in the binding assay.

The amount of inhibition or stimulation of binding of a labeled target by the test compound depends on the binding assay conditions and on the concentrations of binding agent, labeled analyte and test compounds used. Under specified assay conditions, a compound is said to be capable of inhibiting the binding of a second compound to a target compound if the amount of bound second compound is decreased by 50% or preferably 90% or more compared to a control sample.

Alternatively, various known or unknown compounds, including proteins, carbohydrates, and the like, can be assayed for their ability to bind to the channels of this invention. In one embodiment, samples from various tissues are contacted with the target to isolate molecules that interact with the target. In another embodiment, small molecule libraries and high throughput screening methods are used to identify compounds that bind to the target.

Labels for Use in Assays

The amount of binding of the second compound to a target channel protein can be assessed by directly labeling the second compound with a detectable moiety, or by detecting the binding of a labeled ligand that specifically binds to the second compound. A wide variety of labels can be used. The detectable labels of the invention can be primary labels (where the label comprises an element that is detected or that produces a directly detectable signal) or secondary labels (where the detected label binds to a primary label, e.g., as is common in immunological labeling). An introduction to labels, labeling procedures and detection of labels is found in Polak and Van Noorden (1997) *Introduction to Immunochemistry*, $2^{nd}$ ed., Springer Verlag, N.Y. and in Haugland (1996) *Handbook of Fluorescent Probes and Research Chemicals*, a combined catalog and handbook published by Molecular Probes, Inc., Eugene, Oreg. Useful primary and secondary labels or the present invention can include spectral labels such as fluorescein isothiocyanate (FITC) and Oregon Green™, rhodamine and derivatives (e.g. Texas red, tetrarhodimine isothiocyanate (TRITC), etc.), digoxigenin, biotin, phycoerythrin , AMCA, CyDyes™, and the like), radiolabels (e.g., $^3$H, $^{125}$I, $^{35}$S, $^{14}$C or $^{32}$P, enzymes (e.g. horseradish peroxidase, alkaline phosphotase, etc.), spectral colorimetric labels such as colloidal gold and colored glass or plastic (e.g. polystyrene, polypropylene, latex, etc.) beads. The choice of label depends on sensitivity required, ease of conjugation with the compound, stability requirements, and available instrumentation.

In general, a detector that monitors a particular probe or probe combination is used to detect the recognition reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill.

High-Throughput Screening of Candidate Agents that Modulate Potassium Channel Proteins Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Combinatorial Chemical Libraries

Combinatorial chemical libraries are a preferred means to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 12331250).

Preparation and screening of combinatorial chemical libraries are well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random biooligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 69096913), vinylogous polypeptides (Hagihara et al. (1992) *J. Amer. Chem. Soc.* 114: 6568), nonpeptidal peptidomimetics with a Beta D Glucose scaffolding (Hirschmann et al., (1992) *J. Amer. Chem. Soc.* 114: 92179218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology*, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd. Moscow, RU, 3D Pharmaceuticals, Exton, Pa., Martek Biosciences, Columbia, Md., etc.).

High Throughput Assays of Chemical Libraries

Any of the assays for compounds capable of modulating potassium ion channel proteins described herein are amenable to high throughput screening. High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Assays for Modulation of Potassium Flow

The activity of functional potassium channels of this invention can be assessed using a variety of in vitro and in vivo assays, e.g., measuring voltage, current, measuring membrane potential, measuring ion flux, e.g., potassium or rubidium, measuring potassium concentration, measuring second messengers and transcription levels, and using e.g., voltage-sensitive dyes, radioactive tracers, and patch-clamp electrophysiology. In particular such assays can be used to test for modulators both inhibitors and activators of channels.

Modulators of the potassium channels are tested using biologically active, functional two-transmembrane domain type potassium ion channels, either recombinant or naturally occurring. In recombinantly based assays, the subunits are typically expressed and modulation is tested using one of the in vitro or in vivo assays described below.

In brief, samples or assays that are treated with a potential channel inhibitors or activators are compared to control samples without the test compound, to examine the extent of modulation. Control samples e.g, those untreated with activators or inhibitors are assigned a relative potassium channel activity value of 100. Inhibition is present when potassium channel activity value relative to the control is about 90%, preferably 50%, more preferably 25%. Activation of channels is achieved when the select potassium channel activity value relative to the control is 110%, more preferably 150%, more preferable 200% higher.

Changes in ion flux may be assessed by determining changes in polarization (i.e., electrical potential) of the cell or membrane expressing the potassium channels of this invention. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins can be performed by application of the compounds to a bath solution in contact with and comprising cells having an channel of the present invention (see e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $[Ca^{2+}]$.

Prokaryotic Cation Channel Protein Mutated to Mimic a Functional Eukaryotic Cation Channel Protein Furthermore, as explained above, the present invention extends to prokaryotic cation channel proteins mutated to mimic a functional eukaryotic cation channel protein. These mutated cation channel proteins have broad applications in assays for screening potential drugs or therapeutic agents which potentially can interact with eukaryotic cation channel proteins, and be used to treat numerous conditions related to the function of cation channel proteins in vivo, such as cardiac arrhythmia, diabetes mellitus, seizure disorder, asthma or hypertension, to name only a few.

Presently available recombinant DNA techniques, such as site directed mutagenesis for example, can be used to readily mutate one or a number of codons of an isolated nucleic acid molecule encoding A prokaryotic cation channel protein which can then be expressed to produce a mutated prokaryotic cation channel protein which mimics a eukaryotic cation channel protein.

Furthermore, prokaryotic cation channel proteins having applications in this aspect of the present invention comprise prokaryotic potassium channel proteins, prokaryotic sodium channel proteins, or prokaryotic calcium channel proteins. Such prokaryotic cation channel proteins can be obtained from varying prokaryotic organisms, such as *E. coli, Streptomyces lividans, Clostridium acetobutylicum,* or *Staphylococcus aureus,* to name only a few. More specifically, a prokaryotic potassium channel protein comprising an amino acid sequence of SEQ ID NOs:1, 2, 3, or 7, or conserved variants thereof, can be mutated to mimic the physiological functions and chemical properties of numerous eukaryotic cation channel proteins. In a preferred embodiment, a potassium channel protein from *Streptomyces lividans* is mutated to mimic the physiological functions and chemical properties of a eukaryotic cation channel protein, such as eukaryotic potassium channel protein, a eukaryotic sodium channel protein, or a eukaryotic calcium channel protein. Consequently, a potential drug or agent which interacts with a mutated prokaryotic channel protein of the present invention, such as binding thereto for example, should undergo the same or similar interactions with a eukaryotic cation channel protein the prokaryotic cation channel protein was mutated to mimic. Hence, a mutated prokaryotic cation channel protein of the present invention can serve as a model for a specific eukaryotic cation channel protein in screening potential drugs or therapeutic agents for interaction therewith.

Moreover, pursuant to the present invention, and using recombinant DNA techniques, a prokaryotic cation channel protein can be mutated to mimic eukaryotic cation channel proteins from numerous eukaryotic organisms, such as, for example, insects or mammals. More specifically, a prokaryotic cation channel protein can be mutated to mimic eukaryotic cation channel proteins from a wide variety of eukaryotic organisms, such as *Drosophila melanogaster, Homo sapiens, C. elegans, Mus musculus, Arabidopsis thaliana*, or *Rattus novegicus*, to name only a few. Such eukaryotic cation channel proteins comprise an amino acid sequence comprising SEQ ID NOs: 4, 5, 6, 8, 9, 10, 11, 12, 13, or 14, or conserved variants thereof.

In a preferred embodiment of the present invention, the prokaryotic cation channel protein comprises a potassium channel protein from *Streptomyces lividans* comprising an amino acid sequence of SEQ ID NO:1, or conserved variants thereof, which is mutated to comprise an amino acid sequence of SEQ ID NO:16, or conserved variants thereof, in order to mimic the physiological functions and chemical properties of a eukaryotic cation channel protein comprising an amino acid sequence of SEQ ID NO:4. Moreover, such a mutated prokaryotic cation channel protein of the present invention is encoded by an isolated nucleic acid molecule comprising a DNA sequence of SEQ ID NO:17, or degenerate variants thereof.

Mutant Cation Channel Protein

Moreover, the present invention is directed to a mutant cation channel protein. More specifically, the present invention comprises a mutant potassium channel protein comprising an amino acid sequence of SEQ ID NO:16, or conserved variants thereof.

The nomenclature used to define the polypeptides is that specified by Schroder & Lubke, "The Peptides", Academic Press (1965), wherein in accordance with conventional representation the amino group at the N-terminal appears to the left and the carboxyl group at the C-terminal to the right. $NH_2$ refers to the amide group present at the carboxy terminus when written at the right of a polypeptide sequence.

Accordingly, conserved variants of an isolated mutant cation channel protein of the present invention displaying substantially equivalent activity to an isolated cation channel protein of the present invention, are likewise contemplated for use in the present invention. These modifications can be obtained through peptide synthesis utilizing the appropriate starting material.

In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Hence, an amino acid in the mutant cation channel protein of the present invention can be changed in a non-conservative manner (i.e., by changing an amino acid belonging to a grouping of amino acids having a particular size or characteristic to an amino acid belonging to another grouping) or in a conservative manner (i.e., by changing an amino acid belonging to a grouping of amino acids having a particular size or characteristic to an amino acid belonging to the same grouping). Such a conservative change generally leads to less change in the structure and function of the resulting polypeptide. The present invention should be considered to include analogs whose sequences contain conservative changes which do not significantly alter the activity or binding characteristics of the resulting polypeptide.

The following is one example of various groupings of amino acids:

Amino Acids With Nonpolar R Groups

Alanine
Valine
Leucine
Isoleucine
Proline
Phenylalanine
Tryptophan
Methionine

Amino Acids With Uncharged Polar R Groups

Glycine
Serine

Threonine
Cysteine
Tyrosine
Asparagine
Glutamine

Amino Acids With Charged Polar R Groups
(Negatively Charged at pH 6.0)

Aspartic acid
Glutamic acid

Basic Amino Acids (Positively Charged at pH 6.0)

Lysine
Arginine
Histidine (at pH 6.0)

Another grouping may be those amino acids with aromatic groups:

Phenylalanine
Tryptophan
Tyrosine

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Gln for Arg or Lys; and

His for Lys or Arg.

Amino acid substitutions may also be introduced to substitute an amino acid with a particularly preferable property. For example, a Cys may be introduced a potential site for disulfide bridges with another Cys, or with a carrier of the present invention. A His may be introduced as a particularly "catalytic" site (i.e., His can act as an acid or base and is the most common amino acid in biochemical catalysis). Pro may be introduced because of its particularly planar structure, which induces β-turns in the polypeptide's structure. Alternately, D-amino acids can be substituted for the L-amino acids at one or more positions.

Antibodies to an Isolated Mutant Cation Channel Protein of the Invention

As explained above, the present invention further extends to antibodies of a cation channel protein of the present invention, or conserved variants thereof. Such antibodies include but are not limited to polyclonal, monoclonal, chimeric, single chain, Fab fragments, and an Fab expression library. The anti-mutant channel cation protein antibodies of the invention may be cross reactive, e.g., they may recognize cation channel proteins from different species, and even different types of cation channel proteins, i.e. potassium, sodium, calcium channel proteins, or their numerous variants which are gated with different mechanisms (i.e. voltage-gated, mechanical gated, ligand binding gated, etc.). Polyclonal antibodies have greater likelihood of cross reactivity.

Various procedures known in the art may be used for the production of polyclonal antibodies to an isolated mutant cation channel protein, or conserved variants thereof, of the present invention. For the production of antibody, various host animals can be immunized by injection with a mutant cation channel protein, or conserved variants thereof, including but not limited to rabbits, mice, rats, sheep, goats, etc. Furthermore, a mutant cation channel protein, or conserved variants thereof, of the present invention, may be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a mutant cation channel protein of the present invention, or conserved variants thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an isolated mutant cation channel protein of the present invention, or conserved variants thereof, together with a fragment of a human antibody molecule of appropriate biological activity can be used; such antibodies are within the scope of this invention.

According to the invention, techniques described for the production of single chain antibodies [U.S. Pat. Nos. 5,476, 786 and 5,132,405 to Huston; U.S. Pat. No. 4,946,778] can be adapted to produce single chain antibodies specific for an isolated mutant cation channel protein of the invention or conserved variants thereof. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an isolated mutant cation channel protein of the present invention, or conserved variants thereof.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an isolated mutant cation channel protein of the present invention, or conserved variants thereof, one may assay generated hybridomas for a product which binds to a fragment of an isolated mutant cation channel protein, or conserved variants thereof, containing such epitope.

The foregoing antibodies can be used in methods known in the art relating to the localization and activity of an isolated mutant cation channel protein, or conserved variants thereof, e.g., for Western blotting, imaging such a cation channel protein in situ, measuring levels thereof in appropriate physiological samples, etc. using any of the detection techniques mentioned above or known in the art.

In a specific embodiment, antibodies that agonize or antagonize the activity of an isolated mutant cation channel protein of the present invention, or conserved variants thereof, can be generated. Such antibodies can be tested using the assays described infra for identifying ligands.

Detectably Labeled Antibodies of an Isolated Mutant Cation Channel Protein of the Present Invention, or Conserved Variants Thereof Moreover, the present invention extends to antibodies described above, detectably labeled. Suitable detectable labels include enzymes, radioactive isotopes, fluorophores (e.g., fluorescene isothiocyanate (FITC), phycoerythrin (PE), Texas red (TR), rhodamine, free or chelated lanthanide series salts, especially Eu$^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70, 419–439, 1980 and in U.S. Pat. No. 4,857,453.

Suitable enzymes includes, but are not limited to, alkaline phosphatase and horseradish peroxidase.

Other labels for use in the invention include magnetic beads or magnetic resonance imaging labels.

As explained above, the present invention contemplates an isolated nucleic molecule, or degenerate variants thereof, which encode a mutant cation channel protein, or conserved variants thereof. Accordingly, with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotype change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SCC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell,* 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

Moreover, due to degenerate nature of codons in the genetic code, a mutant cation channel protein of the present invention can be encoded by numerous isolated nucleic acid molecules. "Degenerate nature" refers to the use of different three-letter codons to specify a particular amino acid pursuant to the genetic code. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Furthermore, the present invention extends to an isolated nucleic acid molecule, or degenerate variants thereof encoding a mutant cation channel protein, detectably labeled, and a detectably labeled isolated nucleic acid molecule hybridizable under standard hybridization conditions to an isolated nucleic acid molecule, or degenerate variants thereof, encoding a cation channel protein of the present invention. Suitable detectable labels include enzymes, radioactive isotopes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70, 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

Cloning Vectors

The present invention also extends to cloning vectors comprising an isolated nucleic acid molecule of the present invention, or degenerate variants thereof, and an origin of replication. For purposes of this Application, an "origin of replication refers to those DNA sequences that participate in DNA synthesis.

As explained above, in an embodiment of the present invention, an isolated nucleic acid molecule, or degenerate variants thereof, encoding a mutant cation channel protein of the present invention, along with isolated nucleic acid molecules hybridizable under standard hybridization conditions to an isolated nucleic acid, or degenerate variants thereof, which encodes a mutant cation channel protein of the present invention, can be inserted into an appropriate cloning vector in order to produce multiple copies of the isolated nucleic acid. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating an isolated nucleic acid molecule of the present invention or degenerate variants thereof, or an isolated nucleic acid hybridizable thereto under standard hybridization conditions, into a cloning vector which has complementary cohesive termini. However, if the complementary restriction sites used to fragment the isolated nucleic acid or degenerate variants thereof, or an isolated nucleic acid hybridizable thereto under standard hybridization conditions, are not present in the cloning vector, the ends of the isolated nucleic acid molecule or degenerate variants thereof, or an isolated nucleic acid molecule hybridizable under standard hybridization conditions thereto may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Such recombinant molecules can then be introduced into host cells via transformation, transfection, infection, electroporation, etc., so that many copies of an isolated nucleic acid molecule of the present invention, or degenerate variants thereof, or an an isolated nucleic acid molecule hybridizable thereto under standard hybridization conditions, can be generated. Preferably, the cloned isolated nucleic acid molecule is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast $2\mu$ plasmid.

In an alternative method, an isolated nucleic acid molecule of the present invention, or degenerate variants thereof, or an isolated nucleic acid molecule hybridizable thereto under standard hybridization conditions may be identified and isolated after insertion into a suitable cloning vector in a "shot gun" approach. Enrichment for an isolated nucleic acid molecule, for example; by size fractionation, can be done before insertion into the cloning vector.

Expression Vectors

As stated above, the present invention extends to an isolated nucleic acid molecule encoding a mutant cation channel protein of the present invention, degenerate variants thereof, or an isolated nucleic acid hybridizable thereto under standard hybridization conditions.

Isolated nucleic acid molecules of the present invention can be inserted into an appropriate expression vector, i.e., a vector which contains the necessary elements for the transcription and translation of the inserted protein-coding sequence. Such elements are termed herein a "promoter." Thus, an isolated nucleic acid molecule, or degenerate variants thereof, which encodes a mutant cation channel protein of the present, along with isolated nucleic acid molecules hybridizable thereto under standard hybridization conditions is operatively associated with a promoter in an expression vector of the invention. A DNA sequence is "operatively associated" to an expression control sequence, such as a promoter, when the expression control sequence controls and regulates the transcription and translation of that DNA sequence. The term "operatively associated" includes having an appropriate start signal (e.g. ATG) in front of the DNA sequence to be expressed and maintaining the correct reading frame to permit expression of the DNA sequence under the control of the expression control sequence and production of the desired product encoded by the DNA sequence. If an isolated nucleic acid molecule of the present invention does not contain an appropriate start signal, such a start signal can be inserted into the expression vector in front of (5' of) the isolated nucleic acid molecule.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the wild type variant of a mutant cation channel protein of the present invention, and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Moreover, an isolated nucleic acid molecule of the present invention may be expressed chromosomally, after integration of the coding sequence by recombination. In this regard, any of a number of amplification systems may be used to achieve high levels of stable gene expression (See Sambrook et al., 1989, supra).

A unicellular host containing a recombinant vector comprising an isolated nucleic acid molecule, or degenerate variants thereof, which encodes a mutant cation channel protein of the present invention, or an isolated nucleic acid molecule hybridizable under standard hybridization conditions to an isolated nucleic acid molecule, or degenerate variants thereof, which encodes a mutant cation channel protein of the present invention, is cultured in an appropriate cell culture medium under conditions that provide for expression of the isolated nucleic acid molecule by the cell.

Any of the methods previously described for the insertion of DNA fragments into a cloning vector may be used to construct expression vectors comprising an isolated nucleic acid molecule of the present invention, and appropriate transcriptional/translational control signals and the protein coding sequences. These methods may include in vitro recombinant DNA and synthetic techniques and in vivo recombination (genetic recombination).

Expression of an isolated nucleic acid molecule of the present invention, degenerate variants thereof, or an isolated nucleic acid molecule hybridizable thereto under standard hybridization conditions, along with a an isolated mutant cation channel protein encoded by isolated nucleic acid molecules of the present invention, degenerate variants thereof, or an isolated nucleic acid molecule hybridizable thereto under standard hybridization conditions, may be controlled by any promoter/enhancer element known in the art, but these regulatory elements must be functional in the host selected for expression. Promoters which may be used to control expression include, but are not limited to, the SV40 early promoter region (Benoist and Chambon; 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A.

78:1441–1445), the regulatory sequences of the metallothionein gene (Brinster et al., 1982, Nature 296:39–42): prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:79–94; promoter elements from yeast or other fungi such as the Gal 4 promoter, the ADC (alcohol dehydrogenase) promoter. PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984. Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors comprising an isolated nucleic acid molecule, or degenerate variants thereof, encoding a mutant cation channel protein of the present invention, or an expression vector comprising an isolated nucleic acid molecule hybridizable under standard hybridization conditions to an isolated nucleic acid molecule of the present invention, can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if an isolated nucleic of the present invention, or degenerate variants thereof, which encode a mutant cation channel protein of the present invention or conserved variants thereof, or an isolated nucleic acid molecule hybridizable thereto under standard hybridization conditions, is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant, provided that the expressed protein assumes a functionally active conformation.

Production of a Mutant Cation Channel Protein of the Present Invention

Moreover, the present invention extends to a method of producing a mutant cation channel protein comprising an amino acid sequence of SEQ ID NO:16, or conserved variants thereof. More specifically, a method of the present invention comprises the steps of culturing a unicellular host either transformed or transfected with an expression vector of the present invention explained above, under conditions that provide for expression of the mutant cation channel protein, and recovering the mutant cation channel protein from the transformed or transfected unicellular host. As explained above, the conditions which provide for expression of a mutant channel protein of the present invention are dependent upon the expression vector and promoter used to transform or transfect a unicellular host of the invention. Since the conditions needed relative to the promoter used are within the knowledge of one of ordinary skill in this art, conditions for specific promoters are not repeated here.

Moreover, collection of a cation channel protein of the present invention produced pursuant to the method stated above, is also within the knowledge of a skilled artisan.

Crystal of a Cation Channel Protein

As explained above, the present invention extends to a crystal of a cation channel protein having a central pore, which is found natively in a lipid bilayer membrane of an animal cell, such that the central pore communicates with extracellular matrix and cellular cytosol, wherein the crystal effectively diffracts x-rays to a resolution of greater than 3.2 angstroms.

Moreover, the present invention extends to a crystal of a cation channel protein as described above, wherein the cation channel protein comprises a first layer of aromatic amino acid residues positioned to extend into the lipid bilayer membrane proximate to the interface an extracellular matrix and lipid bilayer membrane, a second layer of aromatic amino acid residues positioned to extend into the lipid bilayer membrane proximate to the interface of cellular cytosol and said lipid bilayer membrane, a tetramer of four identical transmembrane subunits, and a central pore formed by the four identical transmembrane subunits.

Furthermore, each transmembrane subunit comprises an inner transmembrane alpha-helix which has a kink therein, an outer transmembrane alpha-helix, and a pore alpha-helix, wherein each subunit is inserted into the tetramer of the cation channel protein so that the outer transmembrane helix of each subunit contacts the first and second layers of aromatic amino acid residues described above, and abuts the lipid bilayer membrane. Moreover, the inner transmembrane helix of each subunit abuts the central pore of the cation channel protein, contacts the first and second layers of aromatic amino acid residues, is tilted by about 25° with respect to the normal of the lipid bilayer membrane, and is packed against inner transmembrane alpha helices of other transmembrane subunits at the second layer of aromatic amino acid residues forming a bundle at the second layer. The pore alpha-helix of each subunit is located at the first layer of said aromatic amino acid residues, and positioned between inner transmembrane alpha-helices of adjacent subunits, and are directed, in an amino to carboxyl sense, towards a point near the center of the central pore.

It has been further determined, based on examination of a crystal of the present invention, that the central pore of a cation channel protein, comprises a pore region located at the first layer of aromatic amino acid residues, and connected to the inner and outer transmembrane alpha-helices of said subunits. More particularly, the pore region comprises about 25–45 amino acid residues, a turret connected to the pore alpha-helix and the outer alpha-helix, wherein the turret is located at the interface of said extracellular matrix and the lipid bilayer membrane. The pore region further comprises an ion selectivity filter connected to the pore alpha-helix and the inner transmembrane alpha-helix of each subunit. The ion selectivity filter extends into the central pore of the cation channel protein, and comprises a signature amino acid residue sequence having main chain atoms which create a stack of sequential oxygen atoms along the selectivity filter that extend into the central pore, and amino acid residues having side chains that interact with the pore helix. It is the signature sequence which enables a cation channel protein to discriminate among the cation intended to permeate the protein, and other cations, so that only the cation intended to permeate the channel protein is permitted to permeate.

The central pore further comprises a tunnel into the lipid bilayer membrane which communicates with the cellular cytosol, and a cavity located within the lipid bilayer membrane between the pore region and the tunnel, and connected to the them, such that the central pore crosses the membrane.

Furthermore, the structure of all ion channel proteins share common features, which are set forth in the crystal of a cation channel protein described above. Consequently, the present invention extends to a crystal of a cation channel protein having a central pore, which is described above, wherein the cation is selected from the group consisting of: $Na^+$, $K^+$, and $Ca^{2+}$. Hence, the present invention extends to crystals of potassium channel proteins, sodium channel proteins, and calcium ion channels, to name only a few. In a preferred embodiment, the crystal of a cation channel protein comprises a crystal of a potassium ion channel protein.

In addition, a crystal of an ion channel protein of a present invention can comprise an amino acid sequence of any presently known, or subsequently discovered cation protein channel. Consequently, the present invention extends to a crystal of a cation channel protein having a central pore, which is found natively in a lipid bilayer membrane of an animal cell, such that the central pore communicates with extracellular matrix and cellular cytosol, wherein the crystal comprises an amino acid sequence of:

residues 23 to 119 of SEQ ID NO:1 (*Streptomyces lividans*);

residues 61 to 119 of SEQ ID NO:2 (*E. coli*);

residues 61 to 119 of SEQ ID NO:3 (*Clostridium acetobutylicum*);

residues 61 to 119 of SEQ ID NO:4 (*Drosophila melanogaster*);

residues 61 to 119 of SEQ ID NO:5 (*Homo sapiens*);

residues 61 to 119 of SEQ ID NO:6 (*Homo sapiens*);

residues 61 to 119 of SEQ ID NO:7 (*Paramecium tetraaurelia*);

residues 61 to 119 of SEQ ID NO:8 (*C. elegans*);

residues 61 to 119 of SEQ ID NO:9 (*Mus musculus*);

residues 61 to 119 of SEQ ID NO:10 (*Homo sapiens*);

residues 61 to 119 of SEQ ID NO:11 (*Arabidopsis thaliana*);

residues 61 to 119 of SEQ ID NO:12 (*Homo sapiens*);

residues 61 to 119 of SEQ ID NO:13 (*Rattus novegicus*); or residues 61 to 119 of SEQ ID NO:14 (*Homo sapiens*);

or conserved variants thereof.

In a preferred embodiment, a crystal of the present invention having a central pore, which is found natively in a lipid bilayer membrane of an animal cell, such that the central pore communicates with extracellular matrix and cellular cytosol, comprises an amino sequence of amino acid residues 23 to 119 of SEQ ID NO:1, has a space grouping of C2, and a unit cell of dimensions of a=128.8 Å, b=68.9 Å, c=112.0 Å, and β=124.6°. Moreover, preferably, the present invention extends to a crystal as described above, wherein the cation $K^+$.

Furthermore, the present invention extends to a crystal of a cation channel protein having a central pore, which is found natively in a lipid bilayer membrane of an animal cell, such that the central pore communicates with extracellular matrix and cellular cytosol, wherein the channel protein comprises a signature sequence comprising:

Thr-Val-Gly-Tyr-Gly-Asp         (SEQ ID NO:15).

Method for Growing a Crystal of the Present Invention

The present invention further extends to a method for growing a crystal of a cation channel protein having a central pore, which is found natively in a lipid bilayer membrane of an animal cell, such that the central pore communicates with extracellular matrix and cellular cytosol, by sitting-drop vapor diffusion. Such a method of the present invention comprises the steps of providing the cation channel protein, removing a predetermined number of carboxy terminal amino acid residues from the cation channel protein to form a truncated cation channel protein, dissolving the truncated cation channel protein in a protein solution, such that the concentration of dissolved truncated channel protein is about 5 to about 10 mg/ml, and mixing equal volumes of protein solution with reservoir mixture at 20° C. Preferably, the reservoir mixture comprises 200 mM $CaCl_2$, 100 mM Hepes, 48% PEG 400, pH 7.5, and the protein solution comprises (150 mM KCl, 50 mM Tris, 2 mM DTT, pH 7.5).

Moreover, the present invention extends to a method of growing a crystal of a cation channel protein as described above, wherein a crystal can be grown comprising any type of cation channel protein. In particular, the present invention can be used to grow crystals of potassium channel proteins, sodium channel proteins, or calcium channel proteins, to name only a few.

Furthermore, the present invention extends to a method of growing a crystal of a cation channel protein, as described herein, wherein the crystal comprises an amino acid sequence of:

residues 23 to 119 of SEQ ID NO:1 (*Streptomyces lividans*);

residues 61 to 119 of SEQ ID NO:2 (*E. coli*);

residues 61 to 119 of SEQ ID NO:3 (*Clostridium acetobutylicum*);

residues 61 to 119 of SEQ ID NO:4 (*Drosophila melanogaster*);

residues 61 to 119 of SEQ ID NO:5 (*Homo sapiens*);

residues 61 to 119 of SEQ ID NO:6 (*Homo sapiens*);

residues 61 to 119 of SEQ ID NO:7 (*Paramecium tetraaurelia*);

residues 61 to 119 of SEQ ID NO:8 (*C. elegans*);

residues 61 to 119 of SEQ ID NO:9 (*Mus musculus*);

residues 61 to 119 of SEQ ID NO:10 (*Homo sapiens*);

residues 61 to 119 of SEQ ID NO:11 (*Arabidopsis thaliana*);

residues 61 to 119 of SEQ ID NO:12 (*Homo sapiens*);

residues 61 to 119 of SEQ ID NO:13 (*Rattus novegicus*); or residues 61 to 119 of SEQ ID NO:14 (*Homo sapiens*);

or conserved variants thereof.

Use of Crystal of a Cation Channel Protein in Assay Systems for Screening Drugs and Agents In another embodiment, the present invention extends to a method of using a crystal of a cation channel protein, as described herein, in an assay system for screening drugs and other agents for their ability to modulate the function of a cation channel protein, comprising the steps of initially selecting a potential drug or agent by performing rational drug design with the three-dimensional structure determined for a crystal of the present invention, wherein the selecting is performed in conjunction with computer modeling. After potential drugs or agents have been selected, a cation channel protein is contacted with the potential drug or agent. If the drug or therapeutic agent has potential use for modulating the function of a cation channel protein, a change in the function of the cation channel after contact with the agent, relative to the function of a similar cation channel protein not contacted with the agent, or the function of the same cation channel protein prior to contact with the agent. Hence, the change in function is indicative of the ability of the drug or agent to modulate the function of a cation channel protein.

Furthermore, the present invention extends to a method of using a crystal of a cation channel protein as described herein, in an assay system for screening drugs and other agents for their ability to modulate the function of a cation channel protein, wherein the crystal comprises a Na$^+$ channel protein, a K$^+$ channel protein, or a Ca$^{2+}$ channel protein.

The present invention further extends to a method of using a crystal of a cation channel protein in an assay for screening drugs or other agents for their ability to modulate the function of a cation channel protein, wherein the crystal of the cation channel protein comprises an amino acid sequence of:

residues 23 to 119 of SEQ ID NO:1 (*Streptomyces lividans*);

residues 61 to 119 of SEQ ID NO:2 (*E. coli*);

residues 61 to 119 of SEQ ID NO:3 (*Clostridium acetobutylicum*);

residues 61 to 119 of SEQ ID NO:4 (*Drosophila melanogaster*);

residues 61 to 119 of SEQ ID NO:5 (*Homo sapiens*);

residues 61 to 119 of SEQ ID NO:6 (*Homo sapiens*);

residues 61 to 119 of SEQ ID NO:7 (*Paramecium tetraaurelia*);

residues 61 to 119 of SEQ ID NO:8 (*C. elegans*);

residues 61 to 119 of SEQ ID NO:9 (*Mus musculus*);

residues 61 to 119 of SEQ ID NO:10 (*Homo sapiens*);

residues 61 to 119 of SEQ ID NO:11 (*Arabidopsis thaliana*);

residues 61 to 119 of SEQ ID NO:12 (*Homo sapiens*);

residues 61 to 119 of SEQ ID NO:13 (*Rattus novegicus*); or residues 61 to 119 of SEQ ID NO:14 (*Homo sapiens*);

or conserved variants thereof.

In a preferred embodiment of a method of using a crystal of a cation channel protein in an assay for screening drugs or other agents for their ability to modulate the function of a cation channel protein, the crystal comprises a potassium channel protein, comprising amino acid residues 23 to 119 of SEQ ID NO:1, a space grouping of C2, and a unit cell of dimensions of a=128.8 Å, b=68.9 Å, c=112.0 Å, and β=124.6°.

Moreover, it is important to note that a drug's or agent's ability to modulate the function of a cation channel protein includes, but is not limited to, increasing or decreasing the cation channel protein's permeability to the specific cation relative the permeability of the same or a similar not contacted with the drug or agent, or the same cation channel protein prior to contact with the drug or agent.

In a further embodiment, the present invention extends to a method of using a crystal of a cation channel protein, as set forth herein, in an assay system for screening drugs and other agents for their ability to treat conditions related to the function of cation channel proteins in vivo, and particularly in abnormal cellular control processes related to the functioning of cation channel protein. Such a method comprises the initial step of selecting a potential drug or other agent by performing rational drug design with the three-dimensional structure determined for a crystal of the invention, wherein the selecting is performed in conjunction with computer modeling. After potential drugs or therapeutic agents are selected, a cation channel protein is contacted with the potential drug or agent. If an interaction of the potential drug or other agent with the cation channel is detected, it is indicative of the potential use of the drug or agent to treat conditions related the function of cation channel proteins in vivo. Examples of such conditions include, but are not limited to, cardiac arrhythmia, diabetes mellitus, seizure disorder, asthma or hypertension, to name only a few.

Furthermore, a crystal of a cation channel protein used in the method for screening drugs or agents for their ability to interact with a cation channel comprises an Na$^+$ channel protein, K$^+$ channel protein, or Ca$^{2+}$ channel protein. Hence, the method of the present invention can be used to screen drugs or agents capable of treating conditions related to the function of such channels.

Moreover, the present invention extends to a crystal used in the method for screening drugs or agents for their ability to interact with a cation channel protein comprising an amino acid sequence of:

residues 23 to 119 of SEQ ID NO:1 (*Streptomyces lividans*);

residues 61 to 119 of SEQ ID NO:2 (*E. coli*);

residues 61 to 119 of SEQ ID NO:3 (*Clostridium acetobutylicum*);

residues 61 to 119 of SEQ ID NO:4 (*Drosophila melanogaster*);

residues 61 to 119 of SEQ ID NO:5 (*Homo sapiens*);

residues 61 to 119 of SEQ ID NO:6 (*Homo sapiens*);

residues 61 to 119 of SEQ ID NO:7 (*Paramecium tetraaurelia*);

residues 61 to 119 of SEQ ID NO:8 (*C. elegans*);

residues 61 to 119 of SEQ ID NO:9 (*Mus musculus*);

residues 61 to 119 of SEQ ID NO:10 (*Homo sapiens*);

residues 61 to 119 of SEQ ID NO:11 (*Arabidopsis thaliana*);

residues 61 to 119 of SEQ ID NO:12 (*Homo sapiens*);

residues 61 to 119 of SEQ ID NO:13 (*Rattus novegicus*); or residues 61 to 119 of SEQ ID NO:14 (*Homo sapiens*); or conserved variants thereof.

In a preferred embodiment, a crystal used in a method for screening drugs or agents for their ability to interact with a cation channel, comprises amino acid residues 23 to 119 of SEQ ID NO:1, has a space grouping of C2, and a unit cell of dimensions of a=128.8 Å, b=68.9 Å, c=112.0 Å, and β=124.6°.

In yet another embodiment, the present invention extends to a method of using a crystal of a cation channel protein described herein, in an assay system for screening drugs and other agents for their ability to permeate through a cation channel protein, comprising an initial step of selecting a potential drug or other agent by performing rational drug design with the three-dimensional structure determined for the crystal, wherein the selecting of the potential drug or agent is performed in conjunction with computer modeling. After a potential drug or agent has been selected, a cation channel protein can be prepared for use in the assay. For example, preparing the cation channel protein can include isolating the cation channel protein from the membrane of a cell, and then inserting the cation channel protein into a membrane having a first and second side which is impermeable to the potential drug or agent. As a result, the cation channel protein traverses the membrane, such that the extracellular portion of the cation channel protein is located on the first side of the membrane, and the intracellular portion of the cation channel protein is located on the second side of the membrane. The extracellular portion of the cation channel membrane can then be contacted with the potential drug or agent. The presence of the drug or agent in the second side of the membrane is indicative of the drug's or agent's potential to permeate the cation channel protein, and the drug or agent is selected based on its ability to permeate the cation channel protein.

In addition, a crystal used in a method for screening drugs or agents for their ability to permeate a cation channel can comprise a $Na^+$ channel protein, a $K^+$ protein channel, or a $Ca^{2+}$ protein channel.

Furthermore, the present invention extends to the use of a crystal in an assay system for screening drugs and other agents for their ability to permeate through a cation channel protein, wherein the crystal comprises an amino acid sequence of:

residues 23 to 119 of SEQ ID NO:1 (*Streptomyces lividans*);

residues 61 to 119 of SEQ ID NO:2 (*E. coli*);

residues 61 to 119 of SEQ ID NO:3 (*Clostridium acetobutylicum*);

residues 61 to 119 of SEQ ID NO:4 (*Drosophila melanogaster*);

residues 61 to 119 of SEQ ID NO:5 (*Homo sapiens*);

residues 61 to 119 of SEQ ID NO:6 (*Homo sapiens*);

residues 61 to 119 of SEQ ID NO:7 (*Paramecium tetraaurelia*);

residues 61 to 119 of SEQ ID NO:8 (*C. elegans*);

residues 61 to 119 of SEQ ID NO:9 (*Mus musculus*);

residues 61 to 119 of SEQ ID NO:10 (*Homo sapiens*);

residues 61 to 119 of SEQ ID NO:11 (*Arabidopsis thaliana*);

residues 61 to 119 of SEQ ID NO:12 (*Homo sapiens*);

residues 61 to 119 of SEQ ID NO:13 (*Rattus novegicus*); or residues 61 to 119 of SEQ ID NO:14 (*Homo sapiens*); or conserved variants thereof.

In a preferred embodiment, the crystal used in an assay system of the present invention for screening drugs and other agents for their ability to permeate through a cation channel protein comprises amino acid residues 23 to 119 of SEQ ID NO:1, has a space grouping of C2, and a unit cell of dimensions of a=128.8 Å, b=68.9 Å, c=112.0 Å, and β=124.6°.

In the assay systems disclosed herein, Once the three-dimensional structure of a crystal comprising a cation channel protein is determined, a potentia drugs and therapeutic agents which may interact with a carrier channel protein, i.e. bind or modulate the function thereof, or perhaps be able to permeate through such a protein can be examined through the use of computer modeling using a docking program such as GRAM, DOCK, or AUTODOCK [Dunbrack et al., 1997, supra]. This procedure can include computer fitting of potential rugs or agents to a cation channel protein to ascertain how well the shape and the chemical structure of the potential drug or agent will complement or interact with a cation channel protein. [Bugg et al., *Scientific American*, Dec.:92–98 (1993); West et al., *TIPS*, 16:67–74 (1995)]. Computer programs can also be employed to estimate the attraction, repulsion, and steric hindrance of a potential drug or agent to a cation channel protein. Generally the tighter the fit, the lower the steric hindrances, and the greater the attractive forces, the more potent the potential drug or agent, since these properties are consistent with a tighter binding, and are clearly indicative of an interaction with a cation channel protein. Furthermore, the more specificity in the design of a potential drug the more likely that the drug will not interact as well with other proteins. This will minimize potential side-effects due to unwanted interactions with other proteins.

Furthermore, computer modeling programs based on the structure of a cation channel protein in a crystal of the present invention, can be used to modify potential drugs or agents in order to identify potentially more promising drugs. Such analysis has been shown to be effective in the development of HIV protease inhibitors [Lam et al., *Science* 263:380–384 (1994): Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)]. Alternatively a potential drug or agent can be obtained by initially screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)]. A peptide selected in this manner would then be systematically modified by computer modeling programs in odrer to enhance its potential interaction with a cation channel protein.

Moreover, through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential drug or agent is identified, it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, alternatively the potential drug or agent may be synthesized de novo. The de novo synthesis of one or even a relatively small group of specific compounds is reasonable in the art of drug design. The potential drug or agent can then be placed into an assay of the present invention to determine whether it binds with a cation channel protein.

When suitable potential drugs or agents are identified, a supplemental crystal is grown which comprises a cation channel protein. Preferably the crystal effectively diffracts X-rays for the determination of the atomic coordinates of the protein-ligand complex to a resolution of greater than 5.0 Angstroms, more preferably greater than 3.0 Angstroms, and even more preferably greater than 2.0 Angstroms. The three-dimensional structure of the supplemental crystal is determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR and AMORE [J. Navaza, *Acta Crystallographics ASO*, 157–163 (1994)]. Once the position and orientation are known an electron density map can be calculated using the search model to provide X-ray phases. Thereafter, the electron density is inspected for structural differences and the search model is modified to conform to the new structure.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

Potassium Channel Structure: Molecular Basis of $K^+$ Conduction and Selectivity The $K^+$ channel from *Streptomyces lividans* is an integral protein with sequence similarity to all known $K^+$ channels, particularly in the pore region. X-ray analysis with data to 3.2 (reveals that four identical subunits create an inverted tepee, or cone, cradling the selectivity filter of the pore in its outer end. The narrow selectivity filter is only 12 Å long, while the remainder of the pore is wider and lined with hydrophobic amino acids. A large, water-filled cavity and helix dipoles are positioned so as to overcome electrostatic destabilization of an ion in the pore at the center of the bilayer. Main-chain carbonyl oxygen atoms from the $K^+$ channel signature sequence line the selectivity filter, which is held open by structural constraints to coordinate $K^+$ ions but not smaller $Na^+$ ions. The selectivity filter contains two $K^+$ ions about 7.5 Å apart. This configuration promotes ion conduction by exploiting electrostatic repulsive forces to overcome attractive forces between $K^+$ ions and the selectivity filter. The architecture of the pore establishes the physical principles underlying selective $K^+$ conduction.

More particularly, potassium ions diffuse rapidly across cell membranes through proteins called $K^+$ channels, which underlie many fundamental biological processes including electrical signaling in the nervous system. Potassium channels use diverse mechanisms of gating (the processes by which the pore opens and closes), but they all exhibit very similar ion permeability characteristics (1). All $K^+$ channels show a selectivity sequence of $K^+ \approx Rb^+ > Cs^+$, while permeability for the smallest alkali metal ions $Na^+$ and $Li^+$ is immeasurably low. Potassium is at least ten thousand times more permeant than $Na^+$, a feature that is essential to the function of $K^+$ channels. Potassium channels also share a constellation of permeability characteristics that is indicative of a multi-ion conduction mechanism. The flux of ions in one direction shows high order coupling to flux in the opposite direction, and ionic mixtures result in anomalous conduction behavior (2). Because of these properties, $K^+$ channels are classified as "long pore channels", invoking the notion that multiple ions queue inside a long, narrow pore in single-file fashion. In addition, the pores of all $K^+$ channels can be blocked by tetraethylammonium ions (3).

Molecular cloning and mutagenesis experiments have reinforced the conclusion that all $K^+$ channels have essentially the same pore constitution. Without exception, they contain a critical amino acid sequence that has been termed the $K^+$ channel signature sequence. Mutation of these amino acids disrupts the channel's ability to discriminate between $K^+$ and $Na^+$ ions (4).

Biophysicists have been tantalized for the past quarter century about chemical basis of the impressive fidelity with which the channel distinguishes between $K^+$ and $Na^+$ ions, which are featureless spheres of Pauling radius 1.33 Å and 0.95 Å and the ability of $K^+$ channels to be concurrently so highly selective and exhibit a throughput rate approaching the diffusion limit. The $10^4$ margin by which $K^+$ is selected over $Na^+$ implies strong energetic interactions between $K^+$ ions and the pore. And yet strong energetic interactions seem incongruent with throughput rates up to $10^8$ ions per second.

Potassium Channel Architecture

Figure 1:
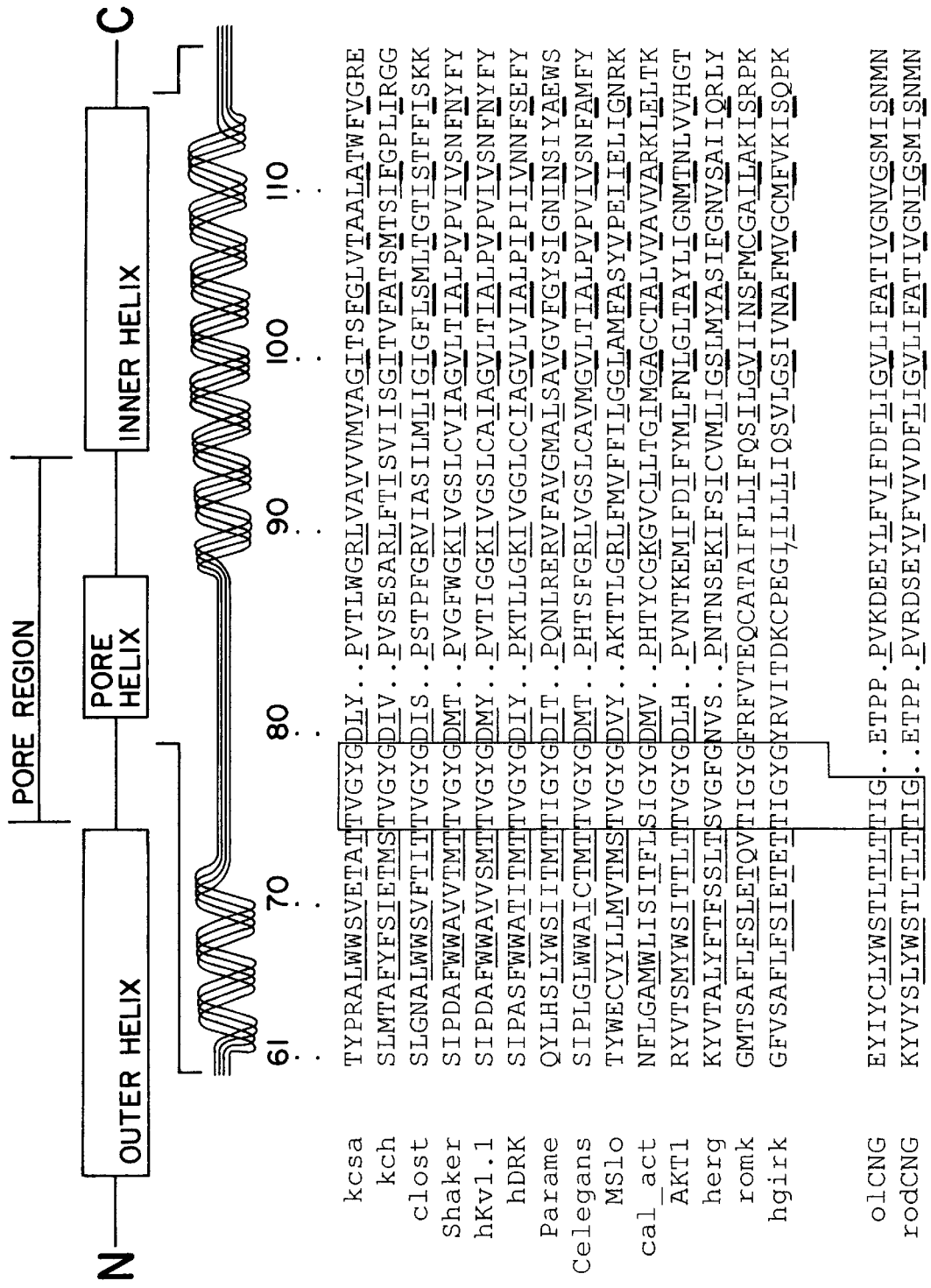
FIG. 1. Sequence alignment of selected $K^+$ channels and cyclic nucleotide-gated channels. The number and secondary structural elements for the Streptomyces lividans $K^+$ channel (kcsa) is given above by the sequences. Selectivity filter, red; lining of the cavity and inner pore, blue; residues in which the nature of the side chain is preserved (>50% similarity), grey. The sequences are: kcsa, Streptomyces lividans accession number (acc) 2127577 (SEQ ID NO:25); kch, Escherichia coli acc 902457 (SEQ ID NO:26); clost, Clostridium acetobutylicum (Genome Therapeutics Corp.) (SEQ ID NO:3); Shaker, Drosophila melanogaster acc 85110 (SEQ ID NO:27); hKv1.1., Homo sapiens acc 1168947 (SEQ ID NO:28); hDRK, Homo sapiens acc 345875 (SEQ ID NO:29); Parame, Paramecium tetraurelia acc 643475 (SEQ ID NO:30); Celegans, Caenorhabiditis elegans acc 2218158 (SEQ ID NO:31); mSlo, Mus musculus acc 539800 (SEQ ID NO:32); cal_act, Homo sapiens acc 2832249 (SEQ ID NO:33); AKT1, Arabidopsis thaliana acc 2129673 (SEQ ID NO:34); herg, Homo sapiens acc 213593 (SEQ ID NO:35); romk, Rattus norvegicus acc 547736 (SEQ ID NO:36); hgirk, Homo sapiens acc 1042217 (SEQ ID NO:37); o1CNG, Homo sapiens acc 2493743 (SEQ ID NO:38); rodCNG, Homo sapiens acc 539557 (SEQ ID NO:39). The last two sequences, separate from the rest, are from cyclic nucleotide-gated channels, which are not $K^+$ selective.

Amino acid sequences show the relationship of the channel from *Streptomyces lividans* (kcsa $K^+$ channel) (5) to other channels in biology, including vertebrate and invertebrate voltage-dependent $K^+$ channels, vertebrate inward rectifier and $Ca^{2+}$-activated $K^+$ channels, $K^+$ channels from plants and bacteria, and cyclic nucleotide-gated cation channels (FIG. 1). On the basis of hydrophobicity analysis, there are two closely related varieties of $K^+$ channels, those containing two membrane-spanning segments per subunit and those containing six. In all cases, the functional $K^+$ channel protein is a tetramer (6), typically of four identical subunits (7). Subunits of the two membrane-spanning variety appear to be shortened versions of their larger counterparts, as if they simply lack the first four membrane-spanning segments. Though the kcsa $K^+$ channel belongs to the two membrane-spanning set of $K^+$ channels, its amino acid sequence is actually closer to those of eukaryotic six membrane-spanning $K^+$ channels. In particular, its sequence in the pore region, located between the membrane-spanning stretches and containing the $K^+$ channel signature sequence, is nearly identical to that found in the Drosophila (Shaker) and vertebrate voltage-gated $K^+$ channels (FIG. 1). Moreover, through a study of the kcsa $K^+$ channel interaction with eukaryotic $K^+$ channel toxins, as described infra. it has been confirmed that the kcsa $K^+$ pore structure is indeed very similar to that of eukaryotic $K^+$ channels, and that its structure is maintained when it is removed from the membrane using detergent (8).

Figure 2A:
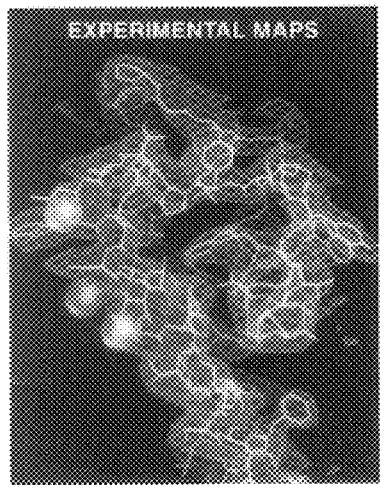
FIG. 2 Experimental electron density map. Stereo views of the experimental electron-display map contoured at 1 σ covering nearly an entire subunit (removed from the tetramer) of the final model. The map was calculated at 3.2 Å resolution with the following Fourier coefficients: native-sharpened amplitudes and MIR solvent flattened averaged phases. (A-B) Foreground: map showing inner helix, loop structures and selectivity filter; background: the pore helix and outer helix. CPK spheres show positions of mercury atoms used as residue markers (from the top, marked residues are Leu86. Leu90 and Val93). (C-D) Alternative view. Foreground: pore helix and part of outer helix; background: selectivity filter and turret. CPK sphere marks position of Ala42. (E-F) Close up view of electron density.
Figure 2B:
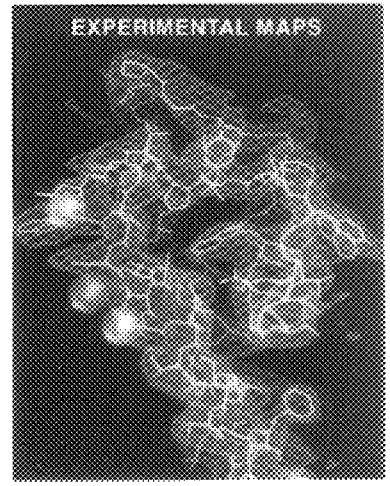
Figure 2C:
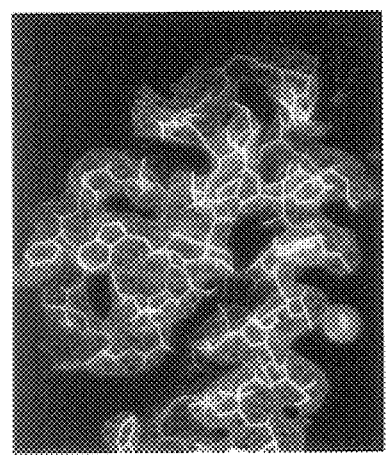
Figure 2D:
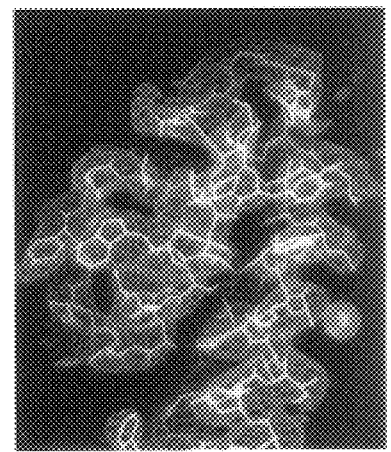
Figure 2E:
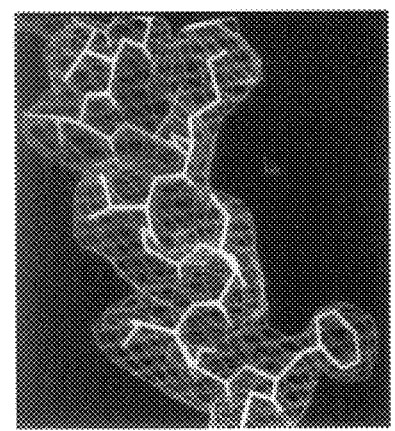
Figure 2F:
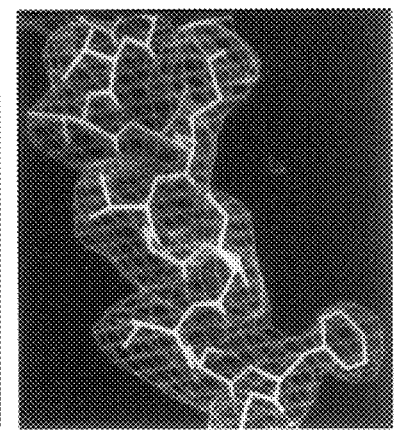
Figure 3A:
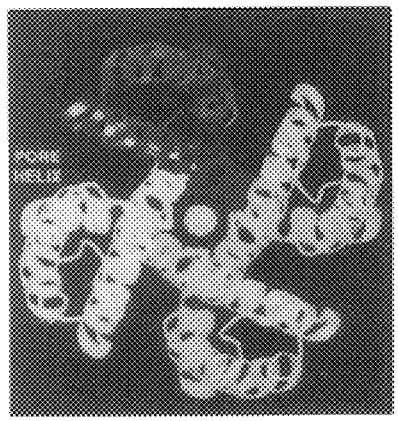
FIG. 3. Views of the tetramer. (A-B) Stereo view of ribbon representation illustrating the three-dimensional fold of the kesa viewed from the extracellular side. The four subunits are distinguished by color. (C-D) Stereo view from another perspective, perpendicular to that in (A-B). (E) Ribbon representation of the tetramer as an integral-membrane protein. Aromatic amino acids present on the membrane-facing surface are displayed in black. (F-G) Inverted tepee architecture of the tetramer. These diagrams were prepared with MOLSCRIPT and RASTER-3D (33 of Example I).
Figure 3B:
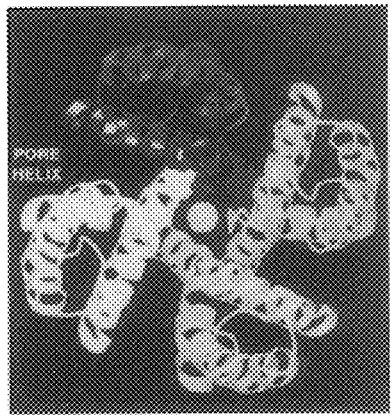
Figure 3C:
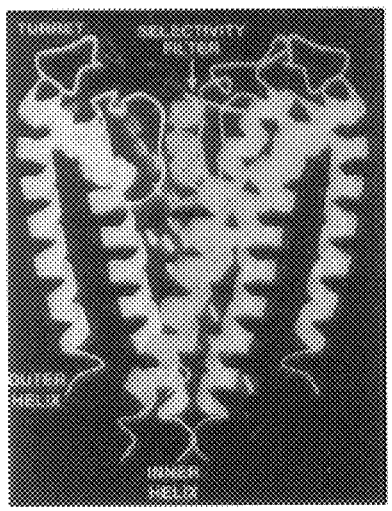
Figure 3D:
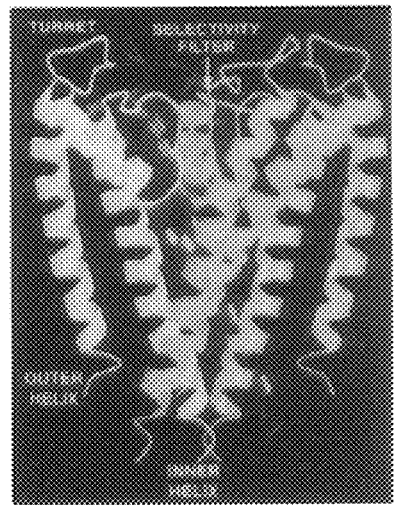
Figure 3F:
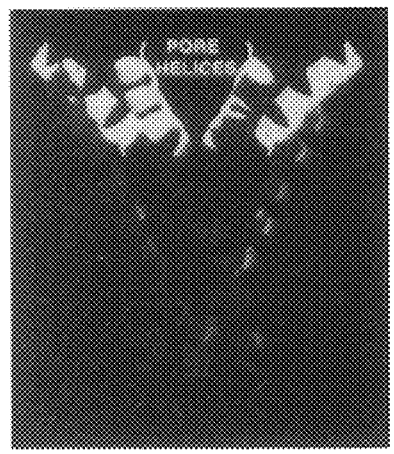
Figure 3G:
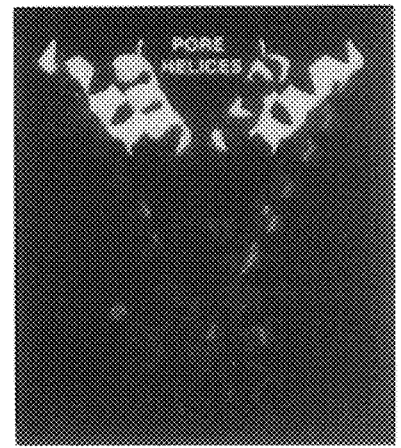
Figure 3E:
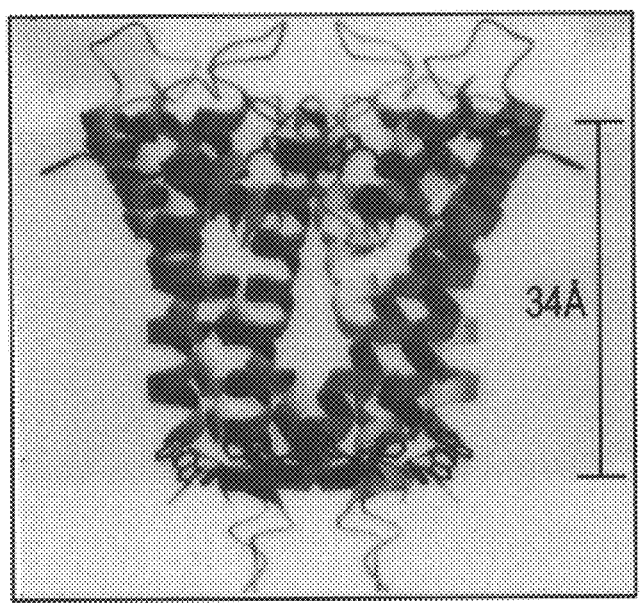

Furthermore, the kcsa K$^+$ channel structure from residue position 23 to 119 of SEQ ID NO:1 has been determined with X-ray crystallography (Table 1). The cytoplasmic carboxyl terminus (residues 126 to 158 of SEQ ID NO:1) were removed in the preparation and the remaining residues were disordered. The kcsa K$^+$ channel crystals are radiation sensitive and the diffraction pattern is anisotropic, with reflections observed along the best and worst directions at 2.5 Å and 3.5 Å Bragg spacings, respectively. By careful data selection, anisotropy correction, introduction of heavy atom sites by site-directed mutagenesis, averaging and solvent flattening, an interpretable electron density map has been calculated (FIGS. 2, A–C). This map was without main chain breaks and showed strong side chain density (FIG. 2C). The model was refined with data to 3.2 Å (the data set was 93% complete to 3.2 Å with 67% completeness between 3.3 Å and 3.2 Å), maintaining highly restrained stereochemistry and keeping tight noncrystallographic symmetry restraints. The refinement was monitored by minimizing the value R-free (29.0%) and its separation from R-crystallographic (28.0%). The presence of four molecules (subunits) in the asymmetric unit of the crystal provides a very significant enhancement of the accuracy of the crystallographic analysis; firstly, by enabling averaging of the electron density over four crystallographically independent regions of the MIR map, and secondly, by providing a powerful set of constraints on the atomic model during refinement (9).

The K$^+$ channel is a tetramer with four-fold symmetry about a central pore (FIGS. 3, A and B). Like several other membrane proteins it has two layers of aromatic amino acids positioned to extend into the lipid bilayer, presumably near the membrane-water interfaces (FIG. 3C) (10). Each subunit has two transmembrane α-helices connected by the roughly 30 amino acid pore-region consisting of the turret, pore helix, and selectivity filter (FIGS. 3 A and B). A subunit is inserted into the tetramer such that one transmembrane helix (inner helix) faces the central pore while the other (outer helix) faces the lipid membrane. The inner helices are tilted with respect to the membrane normal by about 25° and are slightly kinked as shown, so that the subunits open like the petals of a flower facing the outside of the cell. The open petals house the structure formed by the pore region near the extracellular surface of the membrane. This region contains the K$^+$ channel signature sequence, which forms the selectivity filter (4). The essential features of subunit packing can be appreciated by viewing the relation between the four inner helices and the four pore helices (FIG. 3D). The four inner helices against each other as a bundle near the intracellular aspect of the membrane, giving the appearance of an inverted tepee. The pore helices are slotted in between the poles of the tepee and are directed, with an amino to carboxyl sense, towards a point near the center of the channel (FIGS. 3, A,B, and D). This pore helix arrangement is significant in that is provides many of the intersubunit contacts that hold the tetramer together and, as discussed below, is also critical in the operation of the ion conduction pore.

Sequence conservation among K$^+$ channels (including ones with two and six membrane-spanning segments), as well as cyclic nucleotide-gated cation channels, is strongest for the amino acids corresponding to the pore region and the inner helix. Even Na$^+$ and Ca$^{2+}$ channels show distant relatedness over these segments (not shown). It has been concluded that the tepee architecture of the K$^+$ channel pore is a general feature of all of cation channel proteins, and that they all will have four inner helices arranged like the poles of a tepee, four pore helices, and a selectivity filter—tuned to select the appropriate cation—located close to the extracellular surface.

Figure 4:
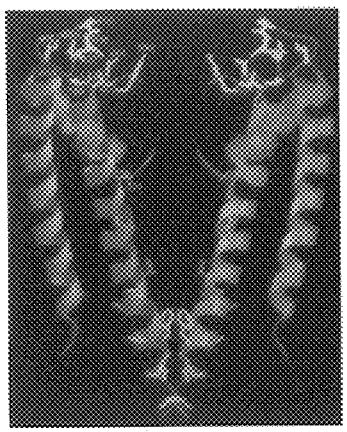
FIG. 4. Mutagenesis studies on Shaker: Mapping the kcsa structure. Mutations in the voltage-gated Shaker $K^+$ channel that affect function are mapped on the equivalent positions in kesa based on the sequence alignment. Two subunits of kesa are shown. Mutation of any of the white side chains significantly alters the affinity of agitoxin2 or charybdotoxin for the Shaker $K^+$ channel (12 of Example I). Changing the yellow side ch native-sharpened amplitudes and MIR-solvent-flattened-averaged phases. The selectivity filter of three subunits is shown as a stick representation with several signature sequence residues labeled. The Rb+ difference map (yellow) is also shown. (C-D) Stereo view of the selectivity filter in a similar orientation to (A-B) with the chain closest to the viewer removed. The three chains represented are comprised of the signature sequence amino acids Thr, Val, Gly, Tyr, Gly (SEQ ID NO:24) running from bottom to top, as labeled in single letter code. The Val and Tyr side chains are directed away from the ion conduction pathway, which is lined by the main chain carbonyl oxygen atoms. Two K+ ions (green) are located at opposite ends of the selectivity filter, roughly 7.5 Å apart, with a single water molecule (red) in between. The inner ion is depicted as in rapid equilibrium between adjacent coordination sites. The filter is surrounded by inner and pore helices (white). Although not shown, the model accounts for hydrogen bonding of all amide nitrogen atoms in the selectivity filter except for that of Gly77. (E) A section of the model perpendicular to the pore at the level of the selectivity filter and viewed from the cytoplasm. The view highlights the network of aromatic amino acids surrounding the selectivity filter. Tyrosine 78 from the selectivity filter Y(78) interacts through hydrogen bonding and van der Waals contacts with two Trp residents (W67, W68) from the pore helix.

Surprisingly, this structure of the kcsa K$^+$ channel is in excellent agreement with extensive functional and mutagenesis studies on Shaker and other eukaryotic K$^+$ channels (FIG. 4). The pore-region of K$^+$ channels was first discovered with pore-blocking scorpion toxins (11). These inhibitors interact with amino acids (white) comprising the broad extracellular-facing entryway to the pore (12). The impermeant organic cation tetraethylammonium (TEA) blocks K$^+$ channels from both sides of the membrane at distinct sites (13). Amino acids interacting with externally and internally applied TEA are located just external to (yellow) and internal to (mustard) the structure formed by the signature sequence amino acids (14, 15). Alteration of the signature sequence amino acids (red main chain atoms) disrupts K$^+$ selectivity (4). Amino acids close to the intracellular opening on the Shaker K$^+$ channel map to the inner helix on the kcsa K$^+$ channel (16). Interestingly, exposure to the cytoplasm of the region above the inner helix bundle (pink side chains) requires an open voltage-dependent gate, whereas the region at or below the bundle (green side chains) is exposed whether or not the gate was open. The correlation between the transition zone for gate dependent exposure to the cytoplasm in the Shaker K$^+$ channel and the inner helix bundle in this structure has implications for mechanisms of gating in K$^+$ channels.

General Properties of the Ion Conduction Pore

Figure 5A:
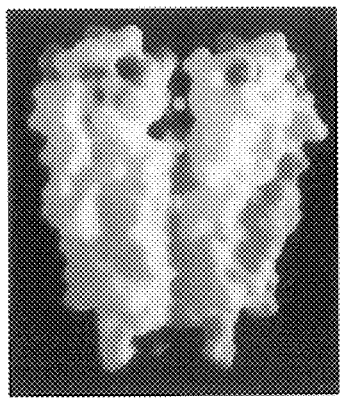
Figure 5B:
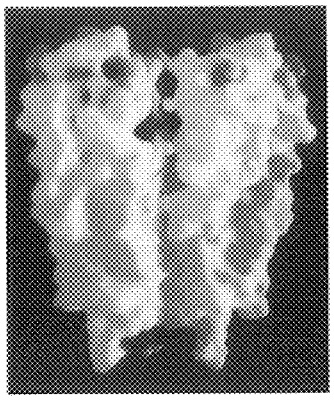
Figure 5C:
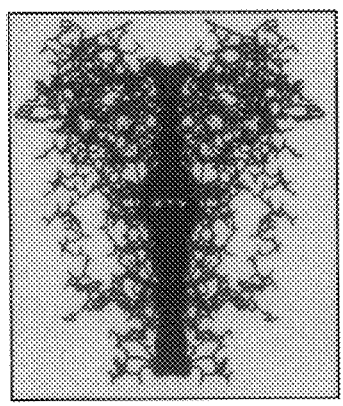
Figure 5D:
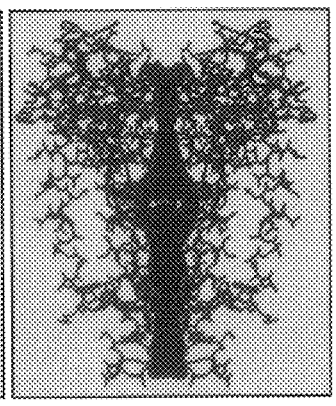

Both the intracellular and extracellular entryways are charged negative by acidic amino acids (FIG. 5A, red), an effect that would raise the local concentration of cations while lowering the concentration of anions. The overall length of the pore is about 45 Å and its diameter varies along its distance (FIG. 5B). From inside the cell (bottom) the pore begins as a tunnel about 18 Å in length (the internal pore) and then opens into a wide cavity (about 10 Å across) near the middle of the membrane. A K$^+$ ion could move throughout the internal pore and cavity and still remain mostly hydrated. In contrast, the selectivity filter separating the cavity from the extracellular solution is so narrow that a K$^+$ ion would have to shed its hydrating waters to enter. The chemical composition of the wall lining the internal pore and cavity is predominantly hydrophobic (FIG. 5A, yellow). The selectivity filter, on the other hand, is lined exclusively by polar main chain atoms belonging to the signature sequence amino acids. The distinct mechanisms operating in the cavity and internal pore versus the selectivity filter are discussed below.

As explained above, potassium channel proteins exclude the smaller alkali metal cations Li$^+$ (radius 0.60 Å) and Na$^+$ (0.95 Å) but allow permeation of the larger members of the series Rb$^+$ (1.48 Å) and Cs$^+$ (1.69 Å). In fact Rb$^+$ is nearly the perfect K$^+$ (1.33 Å) analog as its size and permeability characteristics are very similar to those of K$^+$. Because they are more electron dense than K$^+$, Rb$^+$ and Cs$^+$ allow visualization of the locations of permeant ions in the pore. By difference electron density maps calculated with data from crystals transferred into Rb$^+$-containing (FIG. 6A) or Cs$^+$-containing (FIG. 6B) solutions, multiple ions are well-defined in the pore. The selectivity filter contains two ions (inner and outer ions) located at opposite ends, about 7.5 Å apart (center to center). In the Rb$^+$ difference map, there actually are two partially separated peaks at the inner aspect of the selectivity filter. These peaks are too close to each other (2.6 Å) to represent two simultaneously occupied ion binding sites. Although Applicant ise under no obligation to explain such peaks, and is not to be bound by any explanations, Applicant merely postulates these peaks may represent a single ion (on average) in rapid equilibrium between adjacent sites. The single inner ion peak in the $Cs^+$ difference map undoubtedly reflects the lower resolution at which the map was calculated (to 5 Å or $Cs^+$ versus 4.0 Å for $Rb^+$) since the $Rb^+$ difference map, when calculated at the same lower resolution, also shows only a single peak at the $Cs^+$ position. The $Rb^+$ positions correspond to strong peaks (presumably $K^+$ ions) in a high contour native electron density map (not shown). Thus, the selectivity filter may contain two $K^+$ ions. A third weaker peak is located below the selectivity filter at the center of the large cavity in the $Rb^+$ difference map (FIG. 6A, lower peak) and in the $Cs^+$ difference map at lower contour (not shown). Electron density at the cavity center is prominent in MIR maps even prior to averaging (FIG. 6C, lower diffuse peak). The difference electron density maps show this to be related to the presence of one or more poorly localized cations situated at least 4 Å away from the closest protein groups.

The Cavity and Internal Pore

Figure 6:
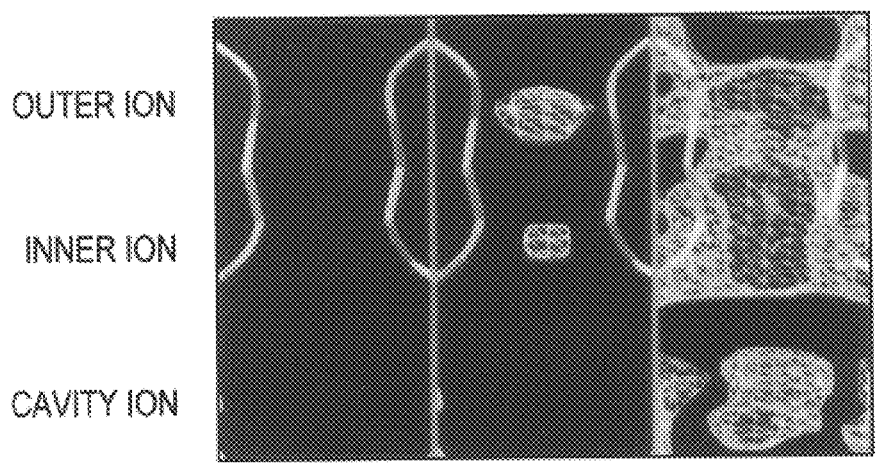
Figure 7:
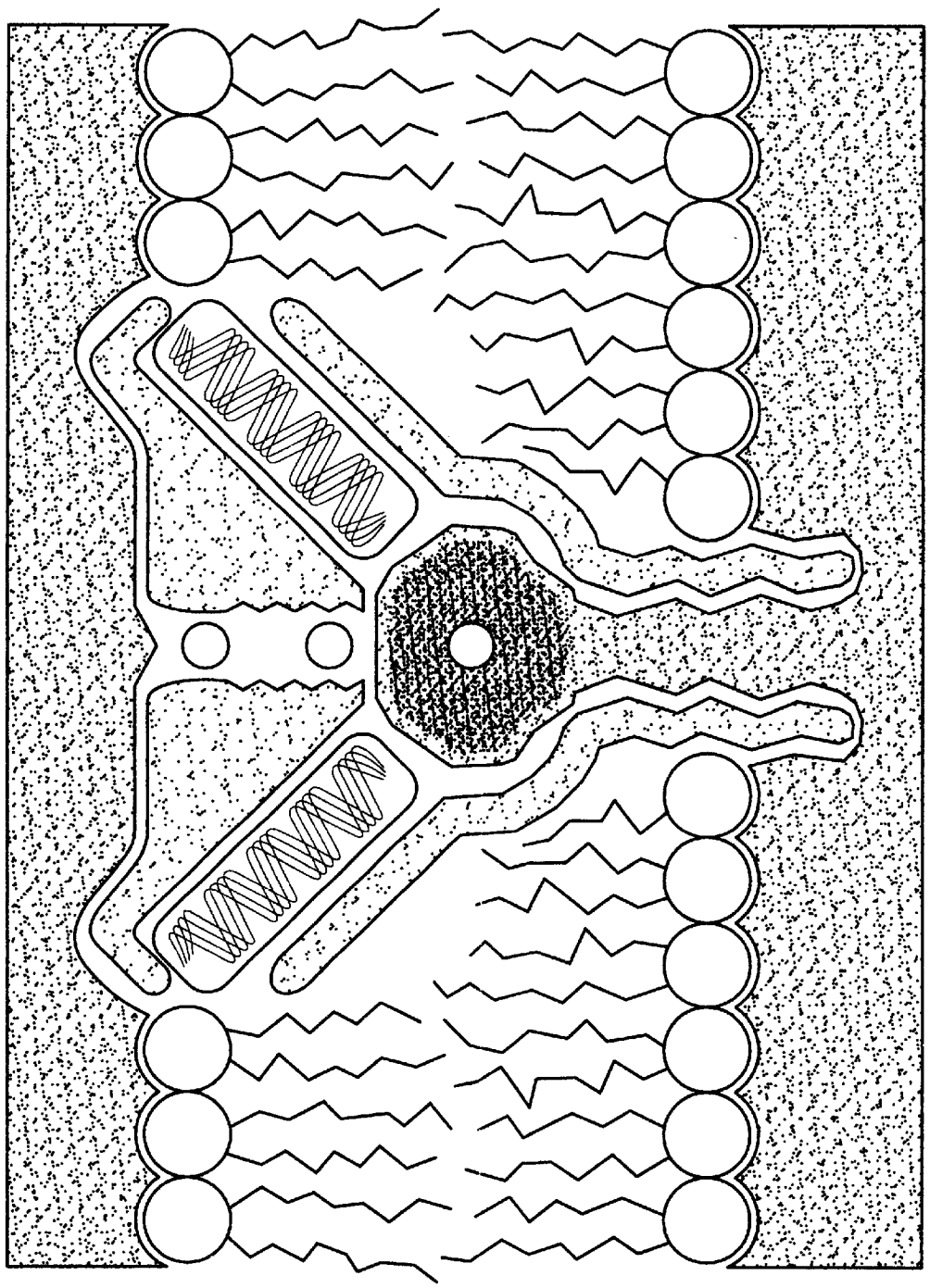

FIGS. 5B and 6 indicate that surprisingly, a 10 Å diameter cavity is in the center of the channel protein with an ion in it. Electrostatic calculations indicate that when an ion is moved along a narrow pore through a membrane it must cross an energy barrier that is maximum at the membrane center (17). The electrostatic field emanating from a cation polarizes its environment, bringing the negative ends of dipoles closer to it and thereby stabilizing it. At the bilayer center, the polarizability of the surrounding medium is minimal and therefore the energy of the cation is highest. Thus, simple electrostatic considerations allow an understanding of the functional significance of the cavity and its strategic location. The cavity will serve to overcome the electrostatic destabilization resulting from the low dielectric bilayer by simply surrounding an ion with polarizable water. A second feature of the $K^+$ channel structure will also stabilize a cation at the bilayer center. The four pore helices point directly at the center of the cavity (FIGS. 3, A, B and D). The amino to carboxyl orientation of these helices will impose a negative electrostatic (cation attractive) potential via the helix dipole effect (18). The ends of the helices are rather far (about 8 Å) from the cavity center, but all four contribute to the effect. Therefore, two properties of the structure, the aqueous cavity and the oriented helices, help to solve a very fundamental physical problem in biology—how to lower the electrostatic barrier facing a cation crossing a lipid bilayer. Thus, the diffuse electron density in the cavity center most likely reflects not an ion binding site, but rather a hydrated cation cloud (FIG. 7).

In summary, the inner pore and cavity lower electrostatic barriers without creating deep energy wells. The structural and chemical design of this part of the pore ensure a low resistance pathway from the cytoplasm to the selectivity filter, facilitating a high throughput. Functional experiments on $K^+$ channels support this conclusion. When TEA from the cytoplasm migrates to its binding site at the top of the cavity, >50% of the physical distance across the membrane (FIG. 4 and FIG. 5), it traverses only about 20% of the transmembrane voltage difference (15). Thus, 80% of the transmembrane voltage is imposed across the relatively short selectivity filter. The rate limiting steps for a $K^+$ ion traversing the channel are thereby limited to this short distance. In effect, the $K^+$ channel has thinned the relevant transmembrane diffusion distance to a mere 12 Å.

The Selectivity Filter

Construction of the atomic model for the $K^+$ channel selectivity filter was based on the experimental electron density map which showed a continuous ridge of electron density attributable to the main chain, as well as strong valine and tyrosine side chain density directed away from the pore (FIG. 8A). $K^+$ ion positions defined by difference Fourier analysis (FIG. 6 and FIG. 8A. yellow density) along with knowledge of alkali metal cation coordination in small molecules were also used in the construction. The side chain locations preclude their direct participation in ion coordination, leaving this function to the main chain atoms. The precise orientation of individual carbonyl oxygens can not be discerned at the resolution of this X-ray analysis. Although Applicant is under no obligation to explain the orientation of individual carbonyl atoms, and are not to be bound by such explanations. Applicant merely proposes they are directed inward to account for $K^+$ ion coordination (FIG. 8B). A single water molecule (the only one modeled in the structure) located between the two $K^+$ ions in the selectivity filter was justified by the presence of a strong electron density peak in the experimental map which was never associated with an ion peak in the difference Fourier maps (19).

The structure of the selectivity filter exhibits two essential features. First, the use of main chain atoms creates a stack of sequential oxygen rings and thus affords numerous closely spaced sites of suitable dimensions for coordinating a dehydrated $K^+$ ion. The $K^+$ ion thus has only a very small distance to diffuse from one site to the next within the selectivity filter. The second important structural feature of the selectivity filter is the protein packing around it. The Val and Tyr side chains from the V-G-Y-G (SEQ ID NO: 40) sequence point away from the pore and make specific interactions with amino acids from the tilted pore helix. In collusion with the pore helix Trp residues, the four Tyr side chains form a massive sheet of aromatic amino acids, twelve in total, that is positioned like a cuff around the selectivity filter (FIG. 8C). The hydrogen bonding, for example between the Tyr hydroxyls and Trp nitrogens, and the extensive van der Waals contacts within the sheet, offer the immediate impression that this structure behaves like a layer of springs stretched radially outward to hold the pore open at its proper diameter.

Applicant postulates, although under no obligation to do so, and not to be bound thereby, that when an ion enters the selectivity filter it evidently dehydrates (nearly completely). To compensate for the energetic cost of dehydration, the carbonyl oxygen atoms must take the place of the water oxygen atoms. That is, they must come in very close contact with the ion and act like surrogate water (20, 21). The structure reveals that the selectivity filter is being held open as if to prevent it from accommodating a $Na^+$ ion with its smaller radius.

Therefore, Applicant postulates that a $K^+$ ion fits in the filter just right, so that the energetic costs and gains are well balanced. Sodium on the other hand is too small. The structure of the selectivity filter with its molecular springs holding it open prevents the carbonyl oxygen atoms from approaching close enough to compensate for the cost of dehydration of a $Na^+$ ion.

This analysis shows that the selectivity filter contains two $K^+$ ions in the presence of about 150 mM $K^+$ (FIG. 6 and FIG. 8). The ions are located at opposite ends of the selectivity filter, separated by about 7.5 Å. That is roughly the average distance between $K^+$ ions in a 4 Molar KCl solution, and in the selectivity filter there are no intervening Cl⁻ anions to balance the charge. Although under no obligation to explain such results, and without intending to be bound by any explanation, Applicant postulates, that the selectivity filter attracts and concentrates $K^+$ ions. The structure implies that a single $K^+$ ion would be held very tightly, but that the presence of two $K^+$ ions results in mutual repulsion, hence their locations near opposite ends of the selectivity filter. Thus, when a second ion enters, the attractive force between a $K^+$ ion and the selectivity filter becomes perfectly balanced by the repulsive force between ions, and this is what allows conduction to occur. This picture accounts for both a strong interaction between $K^+$ ions and the selectivity filter and a high throughput mediated by electrostatic repulsion. On the basis of functional measurements, the same concept of destabilization by multiple ion occupancy has been proposed for $Ca^{2+}$ channels (22) and for $K^+$ channels (23) and perhaps is a general property of all selective ion channels.

Experimental Procedures

Cloning and Expression of the kcsa gene

The kcsa gene was subcloned into pQE60 (Qiagen) vector and expressed in E. coli XL-1 Blue cells upon induction with 1-β-D-thiogalactopyranoside. The carboxy-terminal histidine tagged protein was extracted by homogenization and solubilization in 40 mM decylmaltoside (Antrace). The kcsa $K^+$ channel was purified on a cobalt affinity column. Thirty-five carboxyl terminal amino acids were cleaved by chymotripsin proteolysis. The truncated channel was purified to homogeneity by gel filtration and the detergent exchanged in a final dialysis step against 5 mM N,N,-dimethyldodecylamine-N-oxide (LDAO). Crystals were grown at 20° C. by using the sitting drop method by mixing equal volumes of a solubilizing solution with reservoir mixture. Through the entire preparation, the channel protein was maintained in solutions containing 150 mM KCl. For definition of $K^+$ sites, crystals were transferred into solutions where 150 mM KCl was replaced by 150 mM RbCl or 150 mM CsCl.

X-ray Crystallography

Crystals (space group C2: a=128.8 Å, b=68.9 Å, c=112.0 Å, β=124.6° were flash-frozen by transferring directly from the crystal mother liquor to a stream of boiled-off nitrogen (24). Since crystals of the mutant L90C diffracted significantly better than wild type protein crystals, the former were used for native data collection. Data were collected from multiple crystals and six sets were selected and merged to form the native data set used for structure determination. Mercury derivatives were obtained by direct addition of methyl mercury to the crystallization solution of cysteine mutant crystals. MALDI-TOF mass spectrometry confirmed 60–90% derivatization of crystals prior to data collection. All data were collected at Cornell High Energy Synchrotron Source (CHESS), station A1, using the Princeton 2K CCD (25). Data were processed with DENZO and SCALEPACK (26) and the CCP4 package (27). Heavy atom positions were determined with SHELX-97 (28) and cross-difference Fourier analysis. These positions confirmed the four-fold non-crystallographic symmetry observed in the self-rotation Patterson function and allowed the determination of initial orientation matrices. An initial model (90% complete) was built into a solvent flattened (64% solvent content), four-fold averaged electron density map using the program O (29). The tracing of the model was facilitated by the use of the mercury atom positions as residue markers. L86C was used solely for this purpose. After torsional refinement (with strict four-fold noncrystallographic symmetry constraints) using XPLOR 3.851 (30), this model was used in the anisotropic scaling (sharpening (31)) of the native data with XPLOR. The structure factor sigma values were also rescaled appropriately and the corrected data were used for all subsequent procedure. Four-fold averaging, solvent flattening and phase extension were applied in DM (32), resulting in a marked improvement of the electron density that allowed correction of the model and the building of additional residues. Refinement consisted of rounds of positional (in the initial tages phase information was also included as a restraint) and grouped B-factor refinement in XPLOR. Four-fold noncrystallographic symmetry was highly restrained with the force constant for positional restraints set as 1000 kcal/mol/Å². The diffuse ion cloud described in the text was initially modeled as one or more $K^+$ ions and several water molecules, however the results were unsatisfactory. Therefore, this and other strong unmodeled density present in solvent flattened maps (no averaging included) was Fourier back-transformed, scaled and included in the refinement procedure, as partial structure factors. The final model includes amino acids 23 to 119 of each chain. The following residues were truncated: Arg27 to Cβ, Ile60 to Cγ, Arg64 to Cβ, Glu71 to Cβ and Arg117 to Nε. The stereochemistry is strongly restrained, with no outliers on the Ramachandran plot. The high B-factor values reflect the intensity decay of the data beyond 4 Å.

Summary

Without intending to be bound by such proposals, and with no obligation to explain these results, Applicant proposes the following principles underlying the structure and operation of $K^+$ channels. (i) The pore structure defines an inverted tepee architecture with the selectivity filter held at its wide end. This architecture also describes the pore of cyclic nucleotide-gated channels and probably $Na^+$ and $Ca^{2+}$ channels as well. (ii) The narrow selectivity filter is only 12 Å long, while surprisingly, the remainder of the pore is wider and has a relatively inert hydrophobic lining. These structural and chemical properties favor a high $K^+$ throughput by minimizing the distance over which $K^+$ interacts strongly with the channel. (iii) A large water-filled cavity and helix dipoles help to overcome the high electrostatic energy barrier facing a cation in the low dielectric membrane center. (iv) The $K^+$ selectivity filter is lined by carbonyl oxygen atoms providing multiple closely spaced sites. The filter is constrained in an optimal geometry so that a dehydrated $K^+$ ion fits with proper coordination while the $Na^+$ ion is too small. (v) Two $K^+$ ions at close proximity in the selectivity filter repel each other. The repulsion overcomes the otherwise strong interaction between ion and protein and allows rapid conduction in the setting of high selectivity.

TABLE 1

Summary of data collection and refinement statistics.

Data Collection and Phasing:

| Dataset | Resolution (Å) | Redudancy | Completeness Overall/outer | Rmerge # | Phasing Power ¶ | R-Cullis + |
|---|---|---|---|---|---|---|
| L90C-a | 15.0–3.7 | 3.5 | 91.3/93.3% | 0.071 | 1.61 | 0.70 |
| L90C-b | 15.0–3.7 | 7.0 | 91.5/94.1% | 0.083 | 1.87 | 0.50 |
| V93C | 15.0–3.7 | 4.1 | 98.3/99.1% | 0.075 | 1.35 | 0.63 |
| A32C | 15.0–4.0 | 2.3 | 84.1/83.8% | 0.076 | 1.45 | 0.66 |
| A29C | 15.0–5.0 | 2.7 | 73.9/74.0% | 0.063 | 1.03 | 0.85 |
| A42C | 15.0–6.5 | 2.0 | 90.7/90.3% | 0.057 | 0.97 | 0.81 |
| L86C | 30.0–6.0 | 2.3 | 58.7/58.9% | 0.057 | — | — |

| | | | | I/σI | % of measured data with I/σI > 2 |
|---|---|---|---|---|---|
| Native | 30.0–3.2 | 6.1 | 93.3% | 0.086 | 15.8 | 79 |
| Outer Shell | 3.3–3.2 | 2.3 | 66.6% | 0.286 | 3.9 | 50 |

Anisotropic correction:

| | Average F.O.M* (30.0–3.2 Å) | Average F.O.M* (3.4–3.2 Å) |
|---|---|---|
| Before Sharpening ∂ | 0.76 | 0.55 |
| After sharpening ∂ | 0.83 | 0.64 |

| Refinement: | | Root-mean-square deviation of | |
|---|---|---|---|
| Resolution | 10.0–3.2 Å | bond angles: | 1.096° |
| R-cryst. &: | 28.0% | bond lengths | 0.005 Å |
| R-free &: | 29.0% | ncs related atoms: | 0.006 Å |
| No. of reflections with $\|F\|/\sigma\|F\| > 2$: | 12054 | related atoms: | 10 Å² |
| No. of protein atoms: | 710 per subunit | B-factor for non-bonded atoms: | 36 Å² |
| No. of ligand atoms: | 1 water, 3 K⁺ atoms | | |
| Mean B-factor for side-chain atoms: | 90 Å² | | |
| Mean B-factor for side-chain atoms: | 110 Å² | | |

Rmerge = ΣΣI − Ij / Σ1.:
¶Phasing power = < |Fh| > / < E >;
R-Cullis = Σ||Fph ± Fp| − |Fhc|/Σ|Fph ± Fp|, only for centric data: &
R-cryst. = Σ|Fp − Fp(calc)/Σ|Fp|, r-free the same for R-cryst., but calculated on 10% of data selected in thin resolution shells and excluded from refinement;
*F.O.M.: figure of merit:
σ in both cases four-fold averaging and solvent flattening were applied;
Ij is the observed intensity,
I is the average intensity,
Fh is the root-mean-square heavy-atom structure factor,
E is the lack of closure error,
Fph is the structure factor for the derivative,
Fp is the structure factor for the native,
Fhc is the calculated structure factor for the heavy-atom,
Fp(calc) is the calculated native structure value.

REFERENCES

The following references, along with other relevant information was cited in Example I, and set forth below. All references cited in Example I are hereby incorporated by reference in their entirety.

1. B. Hille, *Ionic Channels of Excitable Membranes, Second Edition* (Sinauer Associates, Inc. Mass. 1992)
2. A. L. Hodgkin and R. D. Keynes, *J. Physiol.* (Lond.) 128, 61 (1955); S. Hagiwara, S. Miyazaki, S. Krasne, S. Ciani, *J. Gen. Physiol.* 70, 269 (1977); B. Hille and W. Schwartz, ibid. 72, 409 (1978); J. Neyton and C. Miller, ibid. 92, 549 (1988).
3. C. M. Armstrong and L. Binstock, *J. Gen. Physiol.* 48, 859 (1965); C. M. Armstrong, ibid. 50, 491 (1966); C. M. Armstrong, ibid. 54, 553 (1969); C. M. Armstrong, ibid. 58, 413 (1971).
4. L. Heginbotham, T. Abramson, R. MacKinnon, *Science* 258, 1152 (1992); L. Heginbotham, Z. Lu, T. Abramson, R. MacKinnon, *J. Biophys.* 66, 1061 (1994).
5. H. Schempf et al., *EMBO J.* 14, 5170 (1995); L. Heginbothan, E. Odessey, C. Miller, *Biochemistry* 36, 10335 (1997); D. Marien Cortes and E. Perozo, ibid. 36, 10343 (1997).
6. R. MacKinnon, *Nature* 350, 232 (1991).
7. Certain K⁺ channels contain the equivalent of two subunits in a single open reading frame. These are thought to form the tetramer through the assembly of two dimer subunits (K. A. Ketchum et al., *Nature* 376, 690 (1995)).
8. R. MacKinnon et al., *Science* (1998).

9. G. J. Kleywegt and R. J. Read, Structure 5, 1557 (1998).
10. J. Deisenhofer et al., Nature 318, 618 (1985); S. W. Cowan et al., Nature 358, 727 (1992); A. Kreusch and G. E. Schulz, J. Mol. Biol. 243, 891 (1994).
11. R. MacKinnon and C. Miller, Science 245, 1382 (1989).
12. R. MacKinnon, L. Heginbotham, T. Abramson, Neuron 5, 767 (1990); M. Stocker and C. Miller, Proc. Natl. Acad. Sci. U.S.A. 91, 9509 (1994); S. A. N. Goldstein, D. J. Pheasant, C. Miller, Neuron 12, 1377 (1994); P. Hidalgo and R. MacKinnon, Science 268, 307 (1995); J. Aiyar et al., Neuron 15, 1169 (1995); D. Naranjo and C. Miller, Neuron 16, 123 (1996); R. Ranganathan, J. H. Lewis, R. MacKinnon, Neuron 16, 131 (1996); A. Gross and R. MacKinnon, Neuron 16, 399 (1996).
13. C. M. Armstrong and B. Hille, J. Gen. Physiol. 59, 388 (1972).
14. R. MacKinnon and G. Yellen, Science 250, 276 (1990).
15. G. Yellen, M. E. Jurman, T. Abramson, R. MacKinnon, ibid. 251, 939 (1991).
16. Y. Liu, M. Holmgren, M. E. Jurman, G. Yellen, Neuron 19, 175 (1997).
17. V. A. Parsegian, Annals NY Acad. Sciences 264, 161 (1975).
18. D. Salin, M. Bycroft, A. R. Fersht, Nature 335, 740 (1988); J. Aqvist, H. Luecke, F. A. Quiocho, A. Warshel, Proc. Natl. Acad. Sci. U.S.A. 88, 2026 (1991); D. J. Lockhart and P. S. Kim, Science 257, 947 (1992); D. J. Lockhart and P. S. Kim, Science 260, 198 (1993).
19. The temperature factors for Val76 and Gly77 main chain atoms (but not side chain atoms) refined to higher values than for neighboring atoms. This result is explicable based on the difference Fourier analysis showing alternative positions of the inner $K^+$ ion in the selectivity filter and therefore, by inference, alternative conformations of the coordinating main chain atoms, depending on the location of the $K^+$ ion.
20. F. Bezanilla and C. M. Armstrong, J. Gen. Physiol. 60, 588 (1972).
21. Hille, ibid. 61, 669 (1973).
22. W. Almers and E. W. McCleskey, J. Physiol. (Lond.) 353, 585 (1984); P. Hess and R. W. Tsien, Nature 309, 453 (1984).
23. J. Neyton and C. Miller, J. Gen. Physiol., 92, 569 (1988).
24. The kcsa gene was subcloned into pQE60 (Qiagen) vector and expressed in E. coli XL-1 Blue cells upon induction with 1-(-D-thiogalactopyranoside. The carboxyl-terminal histidine tagged protein was extracted by homogenization and solubilization in 40 mM decyl-maltoside (Anatrace). The kcsa channel was purified on a cobalt affinity column. Thirty-five carboxyl terminal amino acids were cleaved by chymotrypsin proteolysis. The truncated channel was purified to homogeneity by gel filtration and the detergent exchanged in a final dialysis step against 5 mM N,N-dimethyldodecylamine-N-oxide (LDAO). Crystals were grown at 20(C by using the sitting drop method by mixing equal volumes of protein solution (5–10 mg/ml. 150 mM KCl, 50 mM Tris pH 7.5, 2 mM DTT) with reservoir mixture (200 mM $CaCl_2$, 100 mM Hepes pH 7.5 and 48% PEG 400). Through the entire preparation the channel protein was maintained in solutions containing 150 mM KCl. For definition of $K^+$ sites, crystals were transferred into solutions where 150 mM KCl was replaced by 150 mM RbCl or 150 mM CsCl.
25. M. W. Tate et al., J. Appl. Cryst. 28, 196 (1995); D. J. Thiel, et al., Rev. Sci. Instrum. 67, 1 (1996).
26. Z. Otwinowski, in Data Collection and Processing, L. Sawyer and S. Bailey, Eds. (Science and Engineering Research Council Daresbury Laboratory, Daresbury, UK, 1993), pp. 56–62.
27. Collaborative Computational Project 4 (CCP4), Acta Cryst. D50, 760 (1994).
28. G. M. Sheldrick, Acta Cryst. 46, 467 (1990).
29. T. A. Jones, J. Y. Zou, J. Y. Cowan, M. Kjeldgaard, ibid. A47, 110 (1991).
30. A. T. Brunger, X-Plor (Version 3.851) Manual (New Haven, Conn.: The Howard Hughes Medical Institute and Department of Molecular Biophysics and Biochemistry, Yale University).
31. S. J. Gamblin, D. W. Rodgers, T. Stehle, Proceedings of the CCP4 Study weekend, Daresbury Laboratory, (1996) pp. 163–169.
32. K. Y. J. Zhang and P. Main, Acta Cryst. A46, 377.
33. P. J. Kraulis, J. Appl. Cryst. 24, 946 (1991).
34. O. S. Smart, J. G. Neduvelil, X. Wang, B. A. Wallace, M. P. Sansom, J. Mol. Graphics 14, 354 (1996).

EXAMPLE II

Structural Conservation in Prokaryotic and Eukaryotic $K^+$ Channels Revealed by Scorpion Toxins Scorpion toxins inhibit ion conduction through $K^+$ channels by occluding the pore at their extracellular opening. A single toxin protein binds very specifically to a single $K^+$ channel to cause inhibition. The toxins are 35 to 40 amino acids in length and have a characteristic fold that is held rigidly by three disulfide bridges (1). They are active site inhibitors, because when they bind to the channel they interact energetically with $K^+$ ions in the pore (2–4). The intimate interaction between these inhibitors and the pore of $K^+$ channels has been exploited to gain insights into the structure and function of $K^+$ channels.

Studies employing site-directed mutagenesis of the Shaker $K^+$ channel have mapped the scorpion toxin binding site to regions corresponding to the extracellular entryway of the kcsa $K^+$ channel (4–9). Although the $K^+$ channel selectivity filter amino acids are highly conserved, the residues lining the entryway are quite variable. As if to mirror the amino acid variation at the binding site, the toxins are also highly variable in their amino acid composition. A given scorpion venom is a veritable library of toxins, apparently ensuring that a scorpion will inhibit a large fraction of $K^-$ channel types in its victim. Studies on the specificity of toxin-channel interactions have led to the following understanding. The extracellular entryway to the $K^+$ channel is relatively conserved in its three-dimensional structure but the precise amino acid composition is not conserved. The scorpion toxins have a shape, dictated by their conserved fold, that enables them to fit snugly into the entryway, but the affinity of a given toxin-channel pair depends on the residue match (or mismatch) on both interaction surfaces.

A study of the interaction between the kcsa $K^+$ channel (5) and the scorpion toxin agitoxin2 has been undertaken (10). By producing, through mutagenesis, a competent toxin binding site, it is shown that the kcsa $K^+$ channel pore structure and extracellular entryway is very similar to that of eukaryotic voltage-gated $K^+$ channels such as the Shaker $K^+$ channel from Drosophila and the vertebrate voltage-gated $K^+$ channels, and that mutated potassium channel proteins of prokaryotic organisms mimic the physiological functions and chemical properties of eukaryotic cation binding proteins. By combining functional data collected on the toxin-channel interaction with the structures of both proteins Applicant proposes, without intending to be bound by such proposals, a highly-restrained model of the complex structure.

Experimental Procedures

Three mutations (Q58A, T61S, R64D) were introduced into the kcsa K$^+$ channel gene to modify its pore region sequence using PCR mutagenesis and confirmed by DNA sequencing. The gene also contained a mutation at the second residue (P2A) to introduce an ncoI restriction endonuclease site and it was lacking the last two carboxyl terminal residues (both Arg) to avoid proteolysis during the protein preparation. This gene was cloned into the pQE60 vector for expression with a carboxyl terminal thrombin and hexahistidine fusion. Channel protein was expressed in XL-1 Blue strain of *E. coli* (Stratagene) by induction with 1-β-D-thiogalactopyranoside at a concentration of 1.0 mM. Three hours following induction bacteria were sonicated in 50 mM Tris buffer (7.5), 100 mM KCl, 10 mM Mg$_2$SO$_4$, 25 mg DNAse 1, 250 mM sucrose, in addition to pepstatin, leupeptin, and PMSF. The channel was extracted in the same solution containing 40 mM decylmaltoside (Anatrace) at room temperature. Following centrifugation the supernatant was bound to cobalt resin (Talon) at a protein to resin ratio that will saturate the resin. The resin was washed, and detergent concentration was lowered to 10.0 mM. One mL columns were prepared. The control resin (no channel) was handled in the same manner. The resin preparation was the same for mass spectrometry and binding studies.

Forty mg of *Leiurus quinquestriatus hebraeus* venom (Alomone Labs) was suspended in buffet identical to that of the channel (10.0 mM decylmaltoside) and applied to the column. After washing, channel was eluted with 1.0 M imidazole in the same buffer.

Wild type and mutant agitoxin2 were prepared (10). Tritiated N-ethylmaleimide (NEN Life Sciences) was conjugated to agitoxin2 D20C (14). Binding was performed in a 300 μL volume containing 50 mM Tris (7.5), 100 mM KCl, 10 mM decylmaltoside, and 0.3 μL of cobalt resin saturated with the mutant kcsa K$^+$ channel for 30 minutes at room temperature. Following brief centrifugation the supernatant was removed, resin was applied to a filter, rinsed briefly with ice cold buffer, and then counted in a scintillation counter. All binding measurements were made with a paired control containing a saturating concentration (200 times K$_D$) of unlabeled wild type agitoxin2 to determine nonspecific binding. The competition assay was carried out under the same conditions. Labeled Agitoxin2 at 0.06 μM was always present and unlabeled toxin was added to compete with bound labeled toxin.

Discussion

Figure 9:
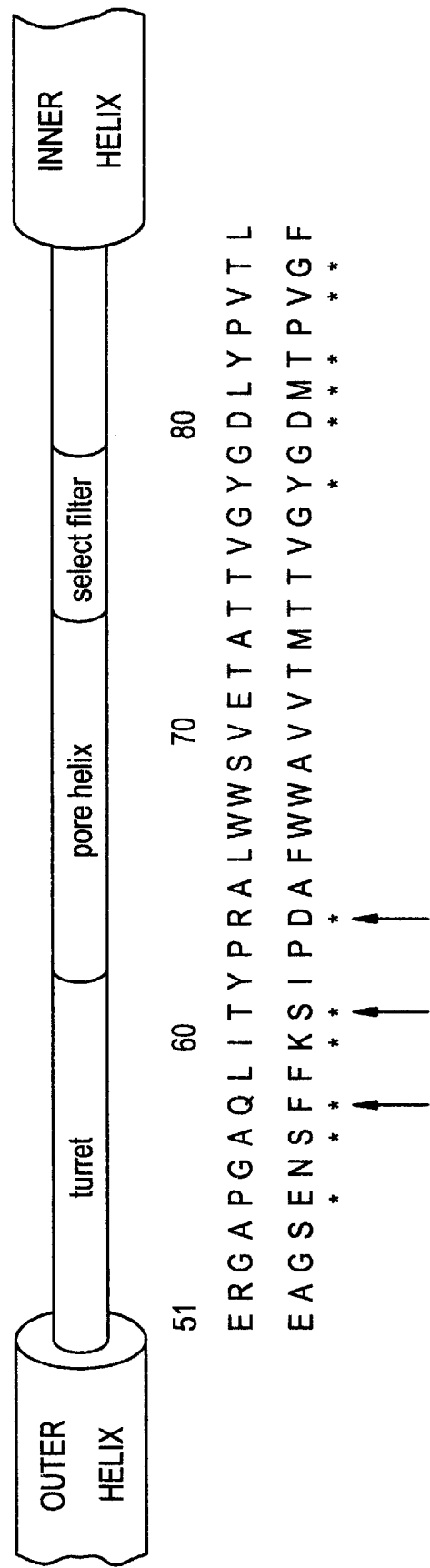
FIG. 9. Sequence alignment of residues 51 to 86 of kcsa K+ (SEQ ID NO:41) and *Shaker* K+(SEQ ID NO: 42) channel pore regions. The numbering for kcsa is given above the sequences. Structural elements are indicated (5 of Example II). Astericks mark several *Shaker* K+channel amino acid locations where mutations influence Agitoxin2 binding (4, 8, 9 of Example II). Arrows mark the three kcsa K+ channel amino acids mutated in this study. The sequences are: kcsa, *Streptomyces lividans* accession number (acc) and Shaker, *Drosophila melanogaster* acc 85110.
Figure 10D:
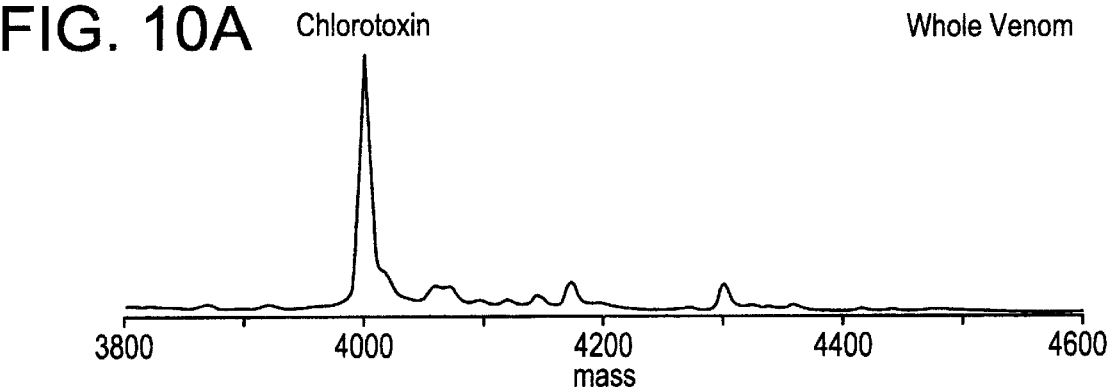
FIG. 10. Mass Spectra of scorpion toxins before and after channel column purification MALDI-TOF mass spectra of venom before purification (A) and after elution from a cobalt column in the absence (B) and presence (C) of attached mutant kcsa K+ channel. The accuracy of the mass measurements (±0.3 Da) permitted identification of most of the major peaks in the mass spectra searched from databases of known toxins of the *Leiurus quinquestratus hebraeus* scorpion (D). The kcsa-binding component labeled * could not be assigned to a known scorpion toxin. The component labeled X (4193.0 Da) binds nonspecifically to the column and was not identified. MALDI_MS was performed with the MALDI matrix 4-hydroxy-α-cyano-cinnamic acid (16 of Example II).
Figure 10D:
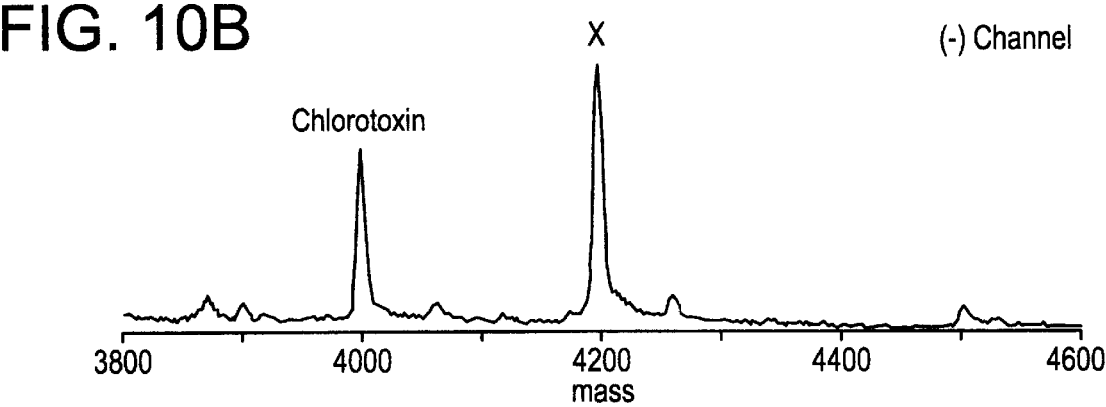
Figure 10D:
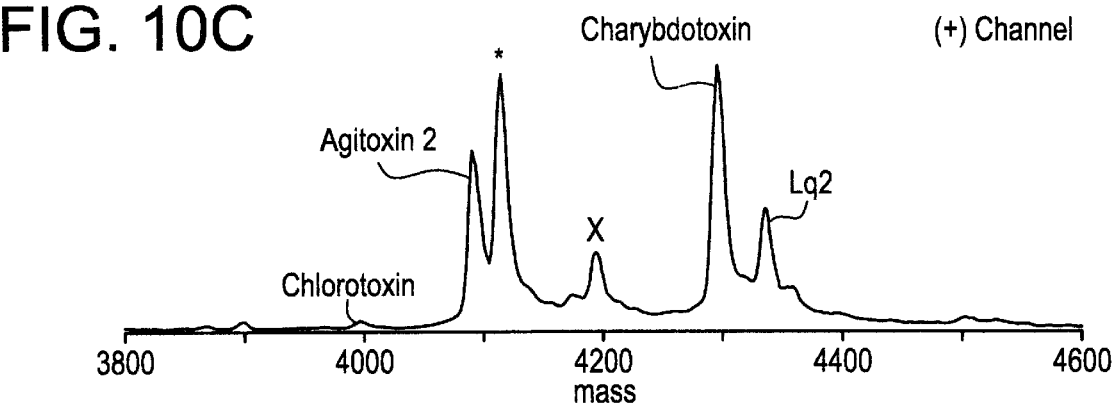
Figure 11A:
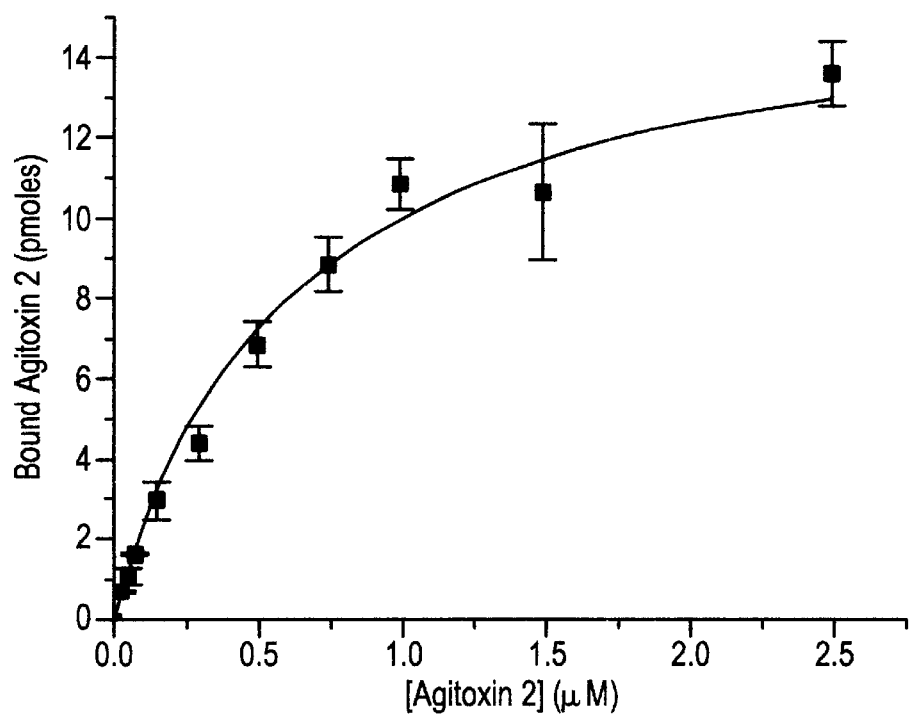
FIG. 11. Binding affinity of wild type and mutant Agitoxin2 to the mutant kcsa K+ channel. (A) Quantity of radiolabeled Agitoxin2 bound to 0.3 µl of cobalt resin saturated with the mutant kcsa K+ channel is shown as a function of the radiolabeled Agitoxin2 concentration (17 of Example II). Each point is the mean ±SEM of 4 measurements, except for the 0.03 µM and 1.5 µM concentrations which are the mean±range of mean of two measurements. The curve corresponds to equation Bond Agitoxin2A*$\{1+K_d/[\text{Agitoxin2}]\}^{-1}$, with equilibrium dissociation constant $K_d$=0.62 µM and resin capacity A=16 pMoles. (B) Remaining bound fraction of radiolabeled wild type toxin is graphed as a function of the concentration of unlabeled wild type toxin or mutant toxins K27A or N30A (17). Each point is mean±SEM of 4 measurements for wild type Agitoxin2 (squares) or mean±range of mean of 2 measurements for K27A (circles) and N30A (triangles)
Figure 11B:
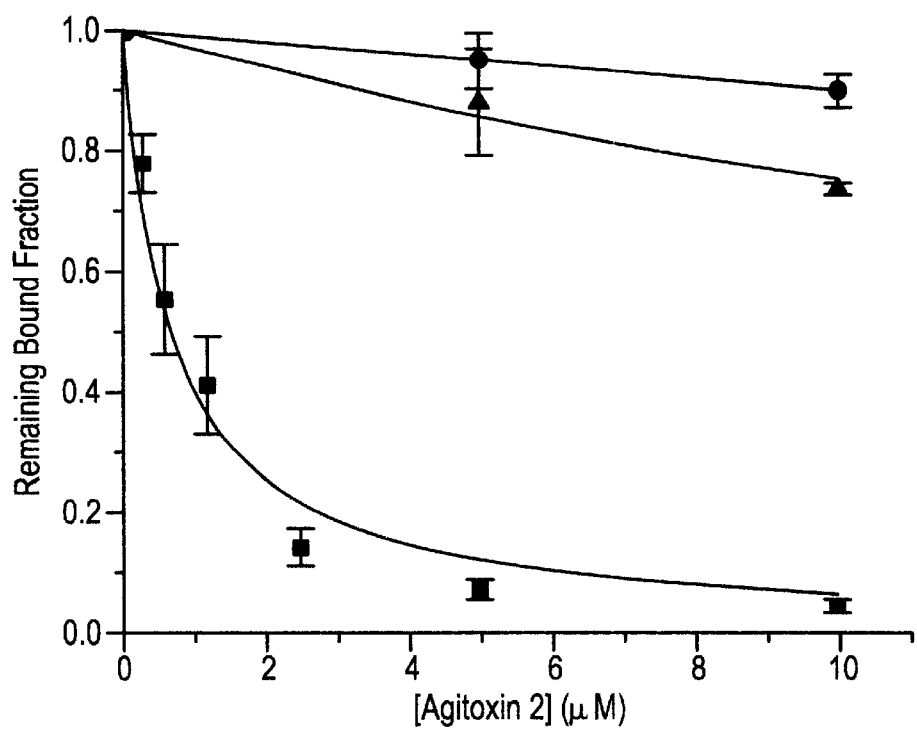
Figure 11C:
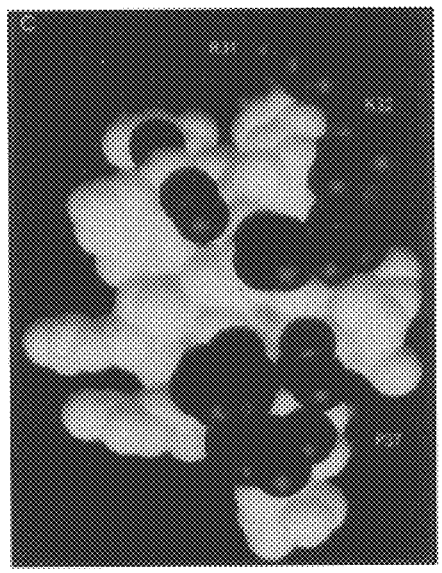
Figure 12B:
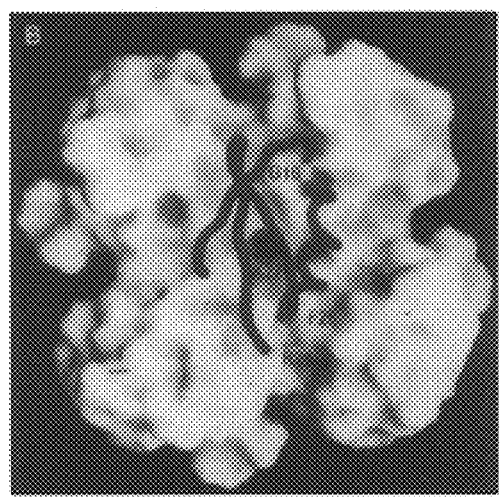

Guided by knowledge of the toxin receptor on the Shaker K$^+$ channel, set forth in SEQ ID NO:4, three point mutations were introduced into the kcsa K$^+$ channel (SEQ ID NO: 1) that should render it sensitive to scorpion toxins (FIG. 9). The amino acid sequence of the mutated kcsa K$^+$ is set forth in SEQ ID NO: 16. Amino acids 61 and 64 of SEQ ID NO: 1 were changed to their Shaker K$^+$ channel counterpart, and 58 was changed to alanine since a small side chain at this latter position favors binding (4, 7). The mutant kcsa $K^+$ channel protein was expressed in *Escherichia coli,* extracted from the membrane with the detergent decylmaltoside, and bound to cobalt resin through a carboxyl terminal hexahistidine tag (11). A 1 mL column, prepared with the $K^+$ channel-containing resin, was used to screen the venom of the Middle East scorpion *Leiurus quinquestriatus hebraeus,* the source of numerous well-characterized ion channel toxins. Forty milligrams of venom was added to the column and after washing, the $K^+$ channel protein was eluted with an imidazole solution (12). The eluate was analyzed with MALDI-TOF mass spectrometry, focusing on the low mass range appropriate for scorpion toxins (about 4000 Da). The $K^+$ channel column resulted in a dramatic enhancement of specific peaks (FIGS. 10A–C). Three of these peaks corresponded in mass to the known $K^+$ channel toxins agitoxin2, charybdotoxin, and Lq2, (FIGS. 10C and D). A fourth peak (FIG. 10C, asterisk) may represent a novel toxin, which is currently under study. However, Applicant is under no obligation to explain this peak, and is not bound by any theories set forth herein regarding this peak. The peak corresponding to chlorotoxin, a reported chloride channel inhibitor (13), did not bind and provides an indication of the degree to which the $K^+$ channel toxins are purified by the mutant kcsa $K^+$ channel column (FIGS. 10A and C).

Further quantitative analysis was carried out with agitoxin2. Radiolabeled agitoxin2 was prepared by producing the mutation D20C in the toxin (located far from its channel binding surface) and conjugating it with tritiated N-ethylmaleimide (14). A filter assay showed that labeled agitoxin2 binds to the mutant kcsa $K^+$ channel with an equilibrium dissociation constant, $K_D$, of about 0.6 mM (FIG. 11A). In contrast, no binding to the wild type channel could be detected (not shown). The total capacity of resin saturated with mutant channel protein, based on the specific activity of radiolabeled toxin and the known 1:1 stoichiometry (one toxin per tetrameric channel), is nearly 50 pmoles of channel per μL of resin. This value approximates the expected capacity of the resin and therefore implies that all of the channel in the preparation must have a correct conformation.

Amino acids in a well-defined region of agitoxin2 form its functional interaction surface, as determined by the effects of alanine substitution on binding to the Shaker $K^{30}$ channel [FIG. 11C (4, 8)]. Mutation of Lys 27 and Asn 30 had the largest destabilizing effects. It is noteworthy that Lys 27 is conserved in all members of this toxin family because its side chain apparently plugs the pore of $K^+$ channels (3). To confirm that agitoxin2 uses the same amino acids to interact with the mutant kcsa $K^+$ channel, the effects of the K27A and N30A toxin mutations with a competition binding assay were studied (FIG. 11B). These mutations decreased the affinity for the toxin significantly (130-fold and 45-fold, respectively), as anticipated from the Shaker $K^+$ channel studies. In contrast, the D20C mutation (predicted to be on the back side of the toxin), even with a bulky N-ethylmaleimide adduct, did not influence affinity (FIGS. 11A and B). These results indicate that agitoxin2 binds in the same manner to both the mutant prokaryotic kcsa $K^+$ channel protein and the eukaryotic Shaker $K^+$ channel protein. The affinity for the Shaker $K^-$ channel is considerably higher ($K_D$ $^-$1 nM), but only three amino acids have been mutated in the prokaryotic cation channel protein to mimic the site on the Shaker $K^+$ channel (FIG. 9).

These results demonstrate that the overall structure of the agitoxin2 receptor site is very similar on both the kcsa and Shaker $K^+$ channels. This conclusion justifies the use of energetic data borrowed from Shaker $K^+$ channel studies to assist in the docking of agitoxin2 onto the kcsa $K^+$ channel structure. Thermodynamic mutant cycle analysis has allowed the identification of numerous energetically coupled residue pairs on the interface [pairs of residues that are related by the fact that mutating one influences the effect (on equilibrium binding) of mutating the other (8)]. The four best defined of these residue pairs are displayed in matched colors on the kcsa $K^+$ channel and agitoxin2 surfaces (FIG. 12A). The three off-center residue pairs (blue, green, yellow)

have the strongest mutant cycle coupling energies [>3 kT (4, 8)]. The central residue pair (red) is coupled by 1.7 kT and independent information places Lys 27 (red residue on agitoxin2, FIG. 11A) over the pore (3, 4). Mere visual inspection suggests a unique orientation for the toxin on the channel (FIG. 12B). If the toxin is placed with its functionally defined interaction surface face-down in the groove formed by the turrets (5), with Lys 27 at the center, the colors match well in three dimensions. The toxin seems to fit perfectly into the vestibule of a $K^+$ channel. The four-fold symmetry of the $K^+$ channel provides four statistically distinguishable but energetically identical orientations available for a toxin to bind [(FIG. 12A) (15)].

In summary, through a combination of structural and functional data, it is shown that prokaryotic channel proteins can be mutated to mimic the physiological functions and chemical properties of eukaryotic channel proteins. Furthermore, disclosed herein is a view of a $K^+$ channel in complex with a neurotoxin from scorpion venom. The kcsa $K^+$ channel is structurally very similar to eukaryotic $K^+$ channels. This unexpected structural conservation, determined through application of techniques developed here, can be exploited to advance our understanding of $K^+$ channel pharmacology, and prepare mutant prokaryotic channel proteins that can be used to screen potential drugs or agents that may interact with eukaryotic cation channel proteins in vivo, and treat conditions related to the functions of proteins.

REFERENCES

The following references, along with other relevant information was cited in Example II, and set forth below. All references cited in Example II are hereby incorporated by reference in their entirety.

1. M. L. Garcia et al., *J. Bioenerg. Biomemb.* 23, 615 (1991); C. Miller, *Neuron* 15, 5 (1995).
2. R. MacKinnon and C. Miller, *J. Gen. Physiol.* 91, 335 (1988); K. M.
3. C. S. Park and C. Miller, *Neuron* 9, 307 (1992).
4. R. Ranganathan, J. H. Lewis, R. MacKinnon, *Neuron* 16, 131 (1996).
5. D. A. Doyle et al., *Science* xxxx (1998).
6. R. MacKinnon and C. Miller, *Science* 245, 1382 (1989); R. MacKinnon, L. Heginbotham, T. Abramson, *Neuron* 5, 767 (1990); M. Stocker and C. Miller, *Proc. Natl. Acad. Sci. USA* 91, 9509 (1994); D. Naranjo and C. Miller, *Neuron* 16, 123 (1996).
7. S. Goldstein, D. J. Pheasant, C. Miller, *Neuron* 12, 1377 (1994).
8. P. Hidalgo and R. MacKinnon, *Science* 268, 307 (1995).
9. A. Gross and R. MacKinnon, *Neuron* 16, 399 (1996).
10. M. L. Garcia et al., *Biochemistry* 33, 6834 (1994).
11. Three mutations (Q58A, T61S, R64D) were introduced into the kcsa $K^+$ channel gene to modify its pore region sequence using PCR mutagenesis and confirmed by DNA sequencing. The gene also contained a mutation at the second residue (P2A) to introduce an ncoI restriction endonuclease site and it was lacking the last two carboxyl terminal residues. This gene was cloned into the pQE60 vector for expression with a carboxyl terminal thrombin and hexahistidine fusion. Channel protein was expressed in XL-1 Blue strain of *E. coli* (Stratagene) by induction with 1-β-D-thiogalactopyranoside at a concentration of 1.0 mM. Three hours following induction bacteria were sonicated in 50 mM Tris buffer (7.5), 100 mM KCl, 10 mM $Mg_2SO_4$, 25 mg DNAse 1, 250 mM sucrose, in addition to pepstatin, leupeptin, and PMSF. The channel was extracted in the same solution containing 40 mM decylmaltoside (Anatrace) at room temperature. Following centrifugation the supernatant was bound to cobalt resin (Talon) at a protein to resin ratio that will saturate the resin. The resin was washed, and detergent concentration was lowered to 10.0 mM. One mL columns were prepared. The control resin (no channel) was handled in the same manner. The resin preparation was the same for mass spectrometry and binding studies.
12. Forty mg of *Leiurus quinquestriatus hebraeus* venom (Alomone Labs) was suspended in buffer identical to that of the channel (10.0 mM declymaltoside) and applied to the column. After washing, channel was eluted with 1.0 M imidazole in the same buffer.
13. J. A. Debin, J. E. Maggio, G. R. Strichartz, *Am. J. Physiol. Soc.* 264, C369 (1993); G. Lippens, J. Najib, S. J. Wodak, A. Tartar, *Biochemistry* 34, 13 (1995).
14. S. K. Aggarwal and R. MacKinnon, *Neuron* 16, 1169 (1996).
15. R. MacKinnon, *Nature* 350, 232 (1991).
16. S. L. Cohen and B. T. Chait, *Anal. Chem.* 68, 31 (1996).
17. Wild type and mutant agitoxin2 were prepared (10). Tritiated N-ethylmaleimide (NEN Life Sciences) was conjugated to agitoxin2 D20C (14). Binding was performed in a 300 μL volume containing 50 mM Tris (7.5), 100 mM KCl, 10 mM declymaltoside, and 0.3 μL of cobalt resin saturated with the mutant kcsa $K^+$ channel for 30 minutes at room temperature. Following brief centrifugation the supernatant was removed, resin was applied to a filter, rinsed briefly with ice cold buffer, and then counted in a scintillation counter. All binding measurements were made with a paired control containing a saturating concentration (200 times $K_d$) of unlabeled wild type agitoxin2 to determine nonspecific binding. The competition assay was carried out under the same conditions. Labeled Agitoxin2 at 0.06 μM was always present and unlabeled toxin was added to compete with bound labeled toxin.
18. A. M. Krezel et al., *Prot. Sci.* 4 1478 (1995).
19. A. Nicholls, K. A. Sharp, B. Honig, *Proteins* 11, 281 (1991).
20. T. A. Jones, J. Y. Zou, J. Y. Cowan, M. Kjeldgaard, *Acta Cryst*, A47, 110 (1991).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method of screening for compounds which selectively bind to a potassium ion channel protein comprising:
   (a) complexing a functional two-transmembrane-domain-type potassium ion channel protein to a solid support;
   (b) contacting the complexed protein/solid support with an aqueous solution said solution containing a compound that is being screened for the ability to selectively bind to the ion channel protein;
   (c) determining whether the compound selectively binds to the ion channel protein with the provisoes that the potassium ion channel protein is in the form of a tetrameric protein; and,
when the protein is mutated to correspond to the agitoxin2 docking site of a Shaker K$^+$ channel protein by substituting amino acid residues permitting the mutated protein to bind agitoxin 2, the protein will bind agitoxin 2 while bound to the solid support, said substituting of residues being within the 36 amino acid domain defined by −25 to +5 of the Shaker K$^+$ selectivity filter (SEQ ID No. 4) where the 0 residue is either the phenylalanine or the tyrosine of the filter's signature sequence selected from the group consisting of glycine-phenylalanine-glycine or glycine-tyrosine-glycine.

2. A method of claim 1 wherein the solid supports are selected from the group comprising: cobalt, insoluble polystyrene beads, PVDF, and polyethylene glycol.

3. The method of claim 1 wherein the two transmembrane-domain-type ion channel is from a prokaryote.

4. A method of claim 1, wherein the two-transmembrane-domain-type ion channel protein is from *Steptomyces lividans*.

5. A method of claim 1 wherein the two-transmembrane-domain-type ion channel protein is KcsA.

6. A method of claim 1 wherein the two-transmembrane-domain-type ion channel protein is mutated from a wild-type protein.

7. A method of claim 6 where the mutation is within the 36 amino acid domain defined by −25 to +5 of the selectivity filter where the 0 residue is either the phenylalanine or the tyrosine of the filter's signature sequence selected from the group consisting of glycine-phenylalanine-glycine or glycine-tyrosine-glycine.

8. A method of claim 6 wherein the mutation deletes a subsequence of the native amino acid sequence and replaces that the native with a subsequence from the corresponding domain of a second and different ion channel protein.

9. A method of claim 8 wherein the second ion channel protein is from a eukaryote.

10. A method claim 1 wherein the aqueous solution comprises a non-ionic detergent.

11. A method of assessing the adequacy of the structural conformation of a two-transmembrane-domain-type potassium ion channel protein for high through put assays comprising the steps of:
   (a) complexing a two-transmembrane-domain-type potassium ion channel protein having a tetrameric form to a non-lipid solid support under aqueous conditions;
   (b) contacting the complexed two-transmembrane-domain-type potassium ion channel protein with a substance known to bind to the two-transmembrane-domain-type potassium ion channel protein when bound to lipid membrane wherein the substance also modulates potassium ion flow in that channel protein; and,
   (c) detecting the binding of the substance to the complexed two-transmembrane-domain-type potassium ion channel protein.

12. A method of claim 11 wherein the two-transmembrane-domain-type potassium ion channel protein is mutated from a wild type two-transmembrane-domain-type potassium ion channel protein by substitution of amino acids.

13. A method of claim 11 wherein the contacting is done in the presence of a non-ionic detergent.

14. A method of claim 11 wherein the substance is a channel blocker.

15. A method of claim 11 wherein the substance is a toxin.

16. A prescreening method for identifying potential modulators for potassium ion channel function comprising:
   (a) binding a soluble potassium ion channel protein to a solid support where the ion channel has the scaffold of a two-transmembrane-domain-type potassium ion channel and has a tetrameric confirmation;
   (b) contacting the soluble potassium ion channel protein of step a with a compound in an aqueous solution; and,
   (c) determining the binding of the compound to the soluble potassium ion channel protein.

17. A method of claim 16 wherein the contacting takes place in the presence of a detergent.

18. A method of claim 16 wherein the ion channel can pass potassium ions when expressed in a cell.

19. A method of claim 16 which further comprises the contacting of the compound to cell expressing a two-transmembrane-domain-type potassium ion channel protein said cell cultured in an aqueous media containing potassium and determining modulation of potassium flow between the inside of the cell and the media.

* * * * *